(12) United States Patent
Okada et al.

(10) Patent No.: US 8,075,853 B2
(45) Date of Patent: Dec. 13, 2011

(54) MICROCHIP

(75) Inventors: Hidetaka Okada, Kyoto (JP); Yasuhisa Kageyama, Kyoto (JP); Shun Momose, Kyoto (JP); Youichi Aoki, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 207 days.

(21) Appl. No.: 12/270,942

(22) Filed: Nov. 14, 2008

(65) Prior Publication Data

US 2009/0142232 A1    Jun. 4, 2009

(30) Foreign Application Priority Data

| Nov. 16, 2007 | (JP) | 2007-298221 |
| Nov. 16, 2007 | (JP) | 2007-298222 |
| Dec. 26, 2007 | (JP) | 2007-334240 |
| Dec. 27, 2007 | (JP) | 2007-336853 |
| Dec. 28, 2007 | (JP) | 2007-339570 |
| May 13, 2008  | (JP) | 2008-126198 |
| Jun. 6, 2008  | (JP) | 2008-149220 |
| Nov. 11, 2008 | (JP) | 2008-288633 |

(51) Int. Cl.
*B01L 3/00* (2006.01)
*G01N 1/10* (2006.01)

(52) U.S. Cl. ........................ 422/502; 436/180
(58) Field of Classification Search .................. 422/502; 436/180
See application file for complete search history.

(56) References Cited

U.S. PATENT DOCUMENTS

| 4,788,154 A * | 11/1988 | Guigan ........................ 436/180 |
| 2007/0003433 A1 | 1/2007 | Horike et al. |
| 2008/0156079 A1 | 7/2008 | Momose et al. |
| 2008/0296734 A1 | 12/2008 | Momose |
| 2009/0084738 A1 | 4/2009 | Momose |
| 2009/0098658 A1 | 4/2009 | Momose et al. |
| 2009/0104077 A1 | 4/2009 | Momose |
| 2009/0111675 A1 | 4/2009 | Yokogawa et al. |
| 2009/0135407 A1 | 5/2009 | Kageyama et al. |
| 2009/0155125 A1 | 6/2009 | Michiue et al. |
| 2009/0232708 A1 | 9/2009 | Yokogawa et al. |

FOREIGN PATENT DOCUMENTS

| JP | 2006-300741 | 11/2006 |
| JP | 2007-017342 | 1/2007 |
| WO | WO 2005/033666 | 4/2005 |

OTHER PUBLICATIONS

U.S. Appl. No. 12/467,404, filed May 18, 2009.
U.S. Appl. No. 12/424,913, filed Apr. 16, 2009.

* cited by examiner

*Primary Examiner* — Lore Jarrett
(74) *Attorney, Agent, or Firm* — Fish & Richardson P.C.

(57) ABSTRACT

The present invention provides a microchip which is made by bonding a first substrate having a groove provided at the substrate surface and a second substrate together, and has a fluid circuit therein, the fluid circuit having a separation portion for separating a first component, and a groove which constitutes the separation portion including an approximately V-shaped region surrounded by prescribed flow channel walls. At a top of the separation portion, a flow rate limiting portion limiting a flow rate of a fluid is preferably provided.

9 Claims, 30 Drawing Sheets

FIG.4A
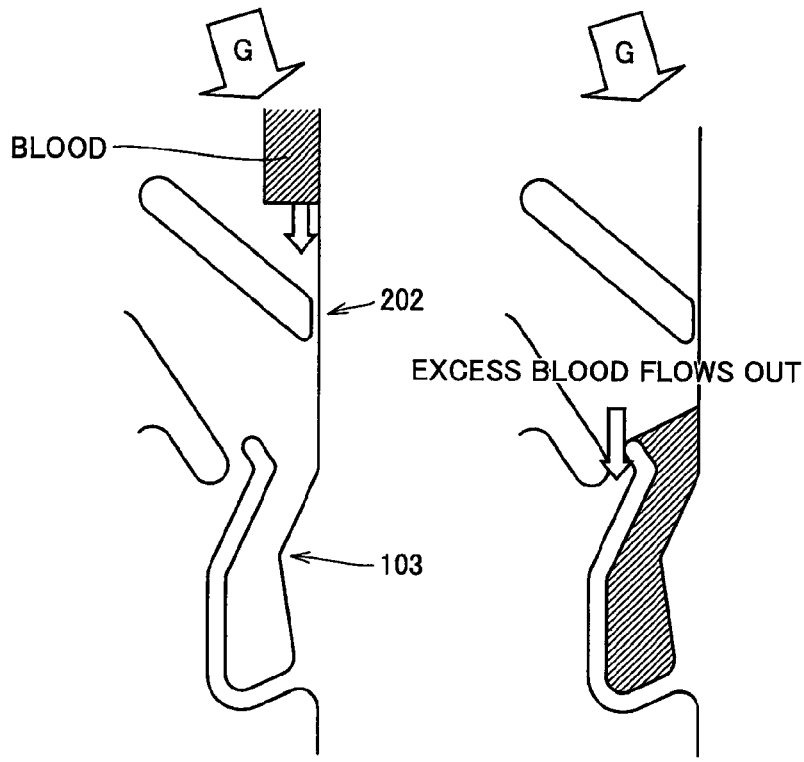
FIG.4B
BLOOD
202
103
EXCESS BLOOD FLOWS OUT
FIG.4C
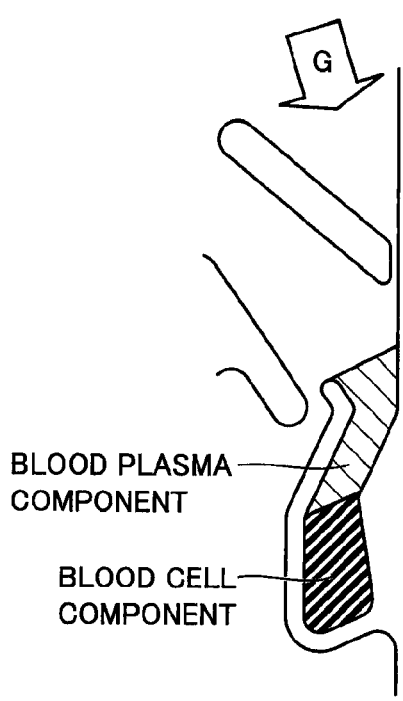
BLOOD PLASMA COMPONENT
BLOOD CELL COMPONENT
FIG.4D
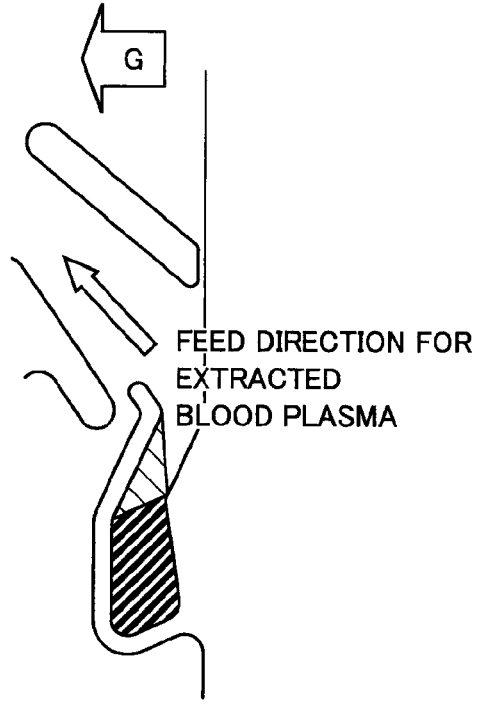
FEED DIRECTION FOR EXTRACTED BLOOD PLASMA

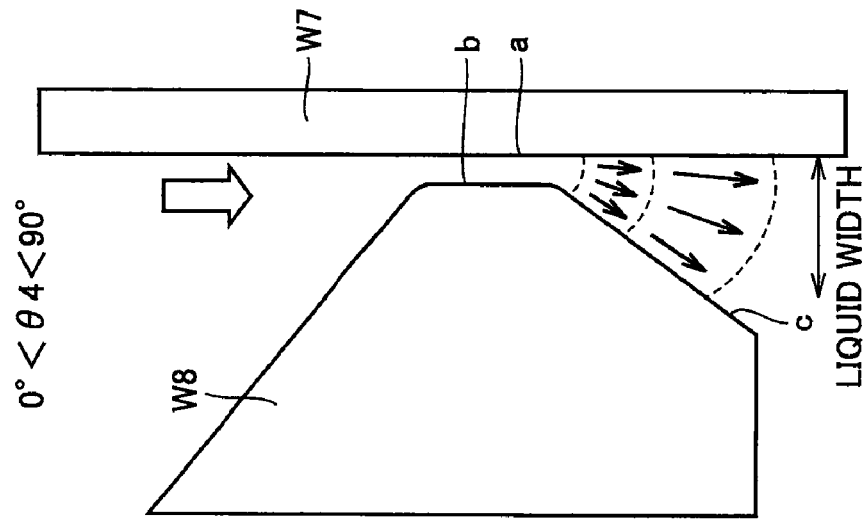
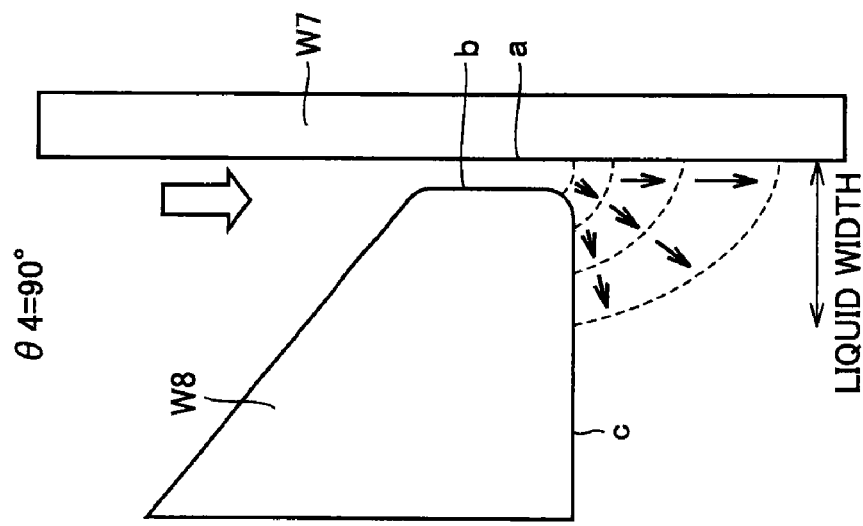
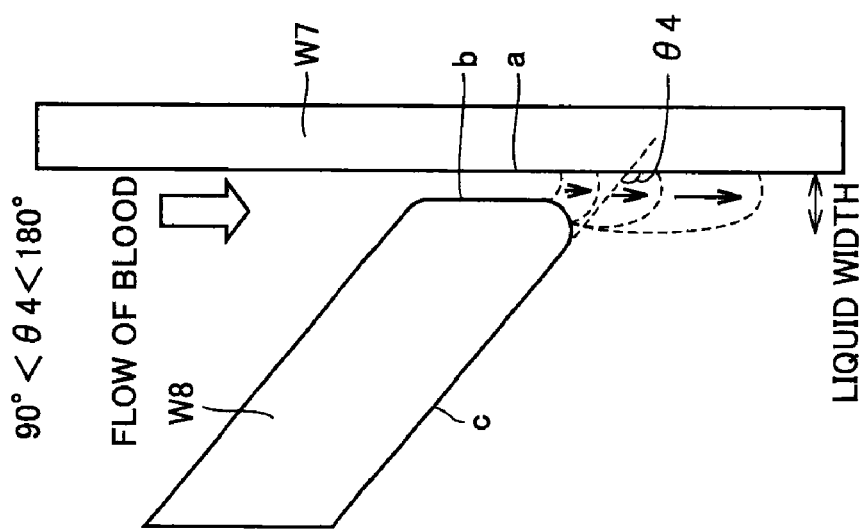

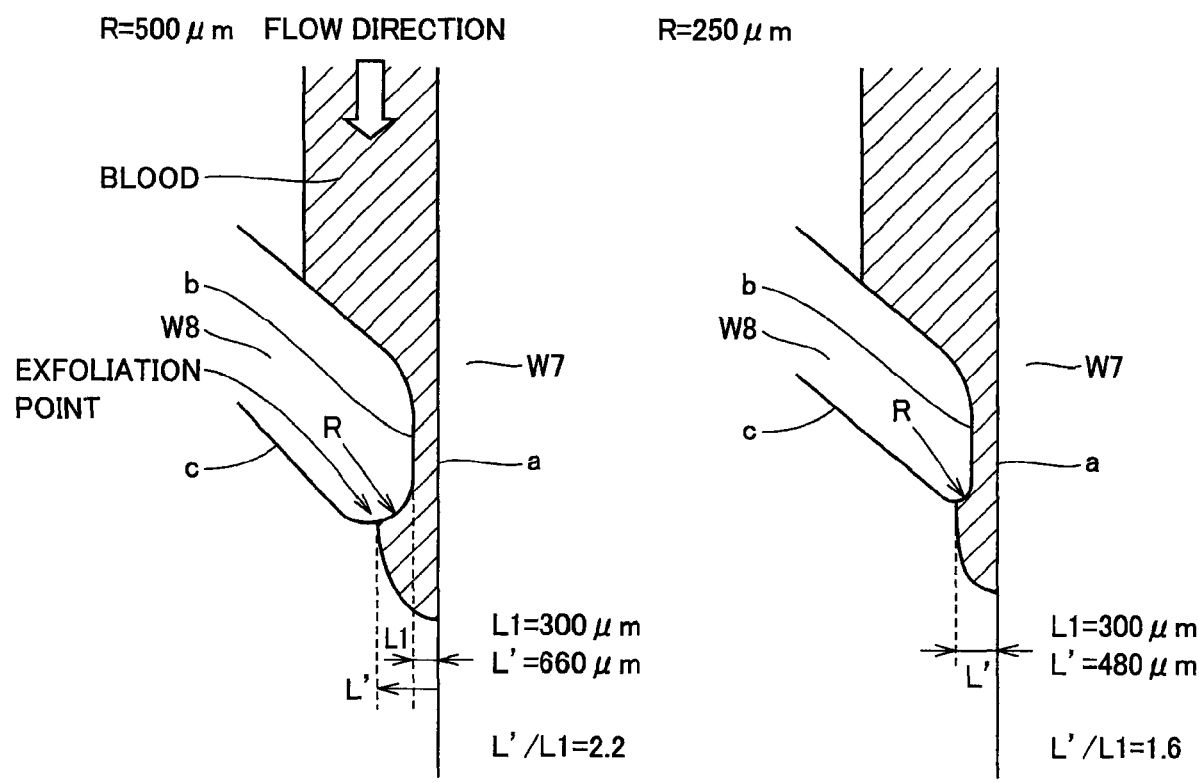

MICROCHIP

BACKGROUND OF THE INVENTION

1. Field of the Invention

The present invention relates to a microchip useful as μ-TAS (Micro Total Analysis System) preferably used for a biochemical test of DNA, protein, a cell, immunity and blood, chemical synthesis and environmental analysis.

2. Description of the Background Art

In recent years, importance of sensing, detecting or determining vital substances such as DNA Deoxyribo Nucleic Acid), an enzyme, an antigen, an antibody, protein, a virus and a cell and a chemical substance has increased in the fields of medical care, health, food and chemical production, and various biochips and microchemical chips (hereinafter these are generically referred to as microchips) capable of simply measuring the same are proposed. A microchip, capable of conducting a series of experimental/analytical operations conducted in a laboratory within a chip of several cm to 10 cm square having a thickness of about several mm to several cm, has such various advantages that the quantities of a specimen and a reagent may be small, the cost is low, the reaction rate is high, a test can be conducted at a high throughput, and a test result can be immediately obtained on the site where the specimen has been collected.

The microchip has a fluid circuit therein, and this fluid circuit can be mainly constituted of portions such as a liquid reagent holding portion holding a liquid reagent for mixing or reacting with a specimen (blood can be listed as an example thereof) or for treating the specimen, a measuring portion measuring the specimen and the liquid reagent, a mixing portion mixing the specimen and the liquid reagent with each other and a detecting portion for conducting analysis and/or a test as to the mixed liquid and a fine flow channel (having a width of about several 100 μm, for example) properly connecting these portions with each other. The microchip is typically placed on an apparatus (centrifugal apparatus) capable of applying centrifugal force thereto and used. Fluid treatments such as measurement of the specimen and the liquid reagent, mixture, and introduction of the mixed liquid into the detecting portion can be performed by applying centrifugal force of a proper direction to the microchip (refer to Japanese Patent Laying-Open No. 2007-017342, for example).

Test/analysis (detection of a specific component in the mixed liquid, for example) of the mixed liquid introduced into the detecting portion can be performed by optical measurement of applying detecting light to the detecting portion in which the mixed liquid is stored and measuring the transmittance thereof, for example (refer to Japanese Patent Laying-Open No. 2006-300741, for example).

In a microchip for a blood test, for example, various tests are generally conducted with a blood plasma component in blood, and hence the fluid circuit of the microchip generally includes a blood plasma separation portion (centrifugation portion) for removing a blood cell component from the blood introduced into the fluid circuit by centrifugation and separating and extracting a blood plasma component. In order to separate a blood plasma and a blood cell from the blood, there are a blood cell separation filter and a method of performing extraction after centrifugation, for example.

A microchip comprising a centrifugal tube for extracting a target component from a sample introduced into a fluid circuit is disclosed in the pamphlet of International Patent Laying-Open No. 05/033666. FIGS. 29, 30, 31, 32, 33 and 34 are schematic step diagrams showing an operating method of the microchip disclosed in the pamphlet of International Patent Laying-Open No. 05/033666. The fluid circuit of the microchip shown in FIGS. 29, 30, 31, 32, 33 and 34 is mainly constituted of an intake 1 for introducing the sample into the fluid circuit, a centrifugal tube 2 connected to intake 1, an adjusting tube 3 consisting of an adjusting tube connecting portion 3a and a reservoir portion 3b, a first weighing portion 4 for measuring the extracted target component, reagent reservoirs 6a and 6b in which a reagent 5 is stored, a primary mixing portion 7 and a secondary mixing portion 8 in which mixing of the target component and reagent 5 is performed and a photodetection channel 9 for conducting test/analysis as to the obtained mixed liquid, and centrifugal tube 2 has a first holding portion 10 for mainly storing a component (nontarget component) other than the target component (see FIG. 29). An outline of the operating method of this microchip is now described with reference to FIGS. 29, 30, 31, 32, 33 and 34.

First, a sample 11 is introduced from intake 1, so that centrifugal tube 2 and adjusting tube connecting portion 3a are filled up (see FIG. 29). Then, the microchip is so rotated around a first rotating axis 12 as to centrifuge sample 11 closer to centrifugal tube 2 than a boundary B-B' in centrifugal tube 2 (see FIG. 30). At this time, a nontarget component 14 other than a target component 13 in sample 11 is stored in first holding portion 10. Sample 11 closer to adjusting tube 3 than boundary B-B' is introduced into reservoir portion 3b. Reagent 5 having been stored in reagent reservoirs 6a and 6b is introduced into primary mixing portion 7 due to this rotation around first rotating axis 12.

Then, the microchip is so rotated around a second rotating axis 15 as to introduce centrifuged target component 13 into first weighing portion 4 from centrifugal tube 2 (see FIG. 31). Target component 13 overflowing first weighing portion 4 is introduced into a waste liquid reservoir 16 connected to first weighing portion 4. Then, the microchip is rotated around first rotating axis 12 again, thereby introducing target component 13 in first weighing portion 4 into primary mixing portion 7 and mixing the same with reagent 5 (see FIG. 32).

Then, a mixed substance 17 as obtained is introduced into secondary mixing portion 8 by sucking the same from a suction port 9a with a pump and further mixed (see FIG. 33), and mixed substance 17 is introduced into photodetection channel 9 (see FIG. 34). Mixed substance 17 introduced into photodetection channel 9 is subjected to optical measurement such as that of introducing light from a light inlet 18 and measuring the quantity of transmission of transmitted light extracted from a light outlet 19, so that test/analysis is conducted. Alternatively, the introduction of obtained mixed substance 17 into secondary mixing portion 8 and the introduction into photodetection channel 9 can also be performed by rotating the microchip around first rotating axis 12 and thereafter rotating the microchip around second rotating axis 15.

According to the microchip described in the pamphlet of International Patent Laying-Open No. 05/033666, as hereinabove described, treatments such as extraction of the target component in the sample, measurement of the target component and mixing with the reagent can be performed by rotating the microchip with the two rotating axes, i.e., first rotating axis 12 and second rotating axis 15 to apply centrifugal force of a proper direction.

SUMMARY OF THE INVENTION

In the conventional microchip for a blood test, the blood cell component may have partially mixed into the blood plasma component when the blood plasma component has been extracted from the blood plasma separation portion, even if it has been possible to separate the blood into a layer of the blood plasma component and a layer of the blood cell component by centrifugation. Such mixing of the blood cell component may hinder correct test/analysis as to the mixed liquid of the blood plasma component and the liquid reagent.

In the conventional microchip for a blood test, further, there has also been such a problem that the liquid width of the blood is so large that the blood fills up a channel in the blood plasma separation portion before reaching the bottom portion of the blood plasma separation portion and hinders discharge of air in the blood plasma separation portion when the blood is introduced into the blood plasma separation portion to easily cause such a phenomenon (clogging phenomenon) that the blood plasma separation portion is not filled with the blood. When such a clogging phenomenon takes place, the blood plasma component cannot be extracted in a necessary quantity, and hence correct test/analysis as to the mixed liquid of the blood plasma component and the liquid reagent may be hindered.

In the aforementioned microchip described in the pamphlet of International Patent Laying-Open No. 05/033666, there has been a possibility that nontarget component 14 having been held in first holding portion 10 and target component 13 flow out when the microchip is rotated around second rotating axis 15 in order to measure target component 13 or the microchip is rotated around second rotating axis 15 in order to introduce mixed substance 17 into photodetection channel 9. Such an outflow from first holding portion 10 may become a factor hindering correct test/analysis for such a reason that the same hinders correct measurement of target component 13. Further, there has been a possibility that gas (air) enters first holding portion 10 and this gas is not discharged but remains when sample 11 introduced into the fluid circuit is introduced into first holding portion 10 by rotating the microchip around first rotating axis 12. When the gas remains in first holding portion 10, there is a possibility that target component 13 is not introduced into first weighing portion 4 in a quantity sufficient for filling up first weighing portion 4, and this also may hinder correct test/analysis.

In the microchip described in the pamphlet of International Patent Laying-Open No. 05/033666, further, it has been impossible to simultaneously perform a test and analysis not only on target component 13 but also on nontarget component 14. For example, it has been difficult to simultaneously extract the blood plasma and the blood cell when performing a test and analysis of whole blood with the microchip. Further, it has been impossible to perform a test and analysis as to nontarget component 14 higher in specific gravity than target component 13. For example, it has been difficult to measure, test and analyze the blood cell when performing a test and analysis of the whole blood with the microchip.

In the conventional microchip, it has been problematic that the blood plasma and the blood cell separated from each other leak to a position different from the route in the fluid circuit designed in this microchip in the aforementioned blood plasma separation portion (centrifugation portion). In this microchip, centrifugal force of various directions is applied to the microchip in various orders in the holding portion etc. for separately holding the blood plasma and the blood cell. Therefore, when only the blood plasma is to be moved from the blood plasma separation portion (centrifugation portion) to the detecting portion of this microchip, for example, the blood cell having been held in the blood plasma separation portion (centrifugation portion) may also have leaked to the detecting portion due to the centrifugal force of various directions with respect to the microchip.

The present invention has been proposed in order to solve the aforementioned problems, and the objects thereof are as follows:

(1) To provide a microchip (microchip for a blood test, for example) capable of extracting a pure first component from a fluid (blood, for example) containing the first component (blood plasma component, for example) and a second component (blood cell component, for example) without mixing the second component and thereby capable of conducting correct and reliable test/analysis on the extracted first component.

(2) To provide a microchip (microchip for a blood test, for example) having a structure capable of reliably filling up a separation portion with a fluid by sufficiently narrowing the liquid width of the fluid at the time of introducing the fluid into the separation portion (blood plasma separation portion, for example) for separating a first component and a second component from each other.

(3) To provide a microchip comprising a centrifugation portion, from which a separated liquid (part of a target component and/or a nontarget component) separated by centrifugation does not flow out due to subsequent application of centrifugal force, capable of preventing gas (air) from remaining in centrifugation.

(4) In relation to a microchip for testing and analyzing a specimen in which a first target substance and a second target substance different in specific gravity from each other, such as blood in which a blood plasma and a blood cell are mixed with each other, for example, to provide a microchip capable of separating the first target substance and the second target substance from each other and simultaneously detecting/analyzing both substances.

(5) In relation to a microchip for testing and analyzing a specimen in which a first target component and a second target component larger in specific gravity than the first target component are mixed with each other, such as blood in which a blood plasma and a blood cell are mixed with each other, for example, to provide a microchip capable of separating the first target component and the second target component from each other and precisely measuring, testing and analyzing the second target component.

(6) In relation to a microchip for testing and analyzing a specimen in which a first target component and a second target component larger in specific gravity than the first target component are mixed with each other, such as blood in which a blood plasma and a blood cell are mixed with each other, for example, to provide a microchip capable of reliably employing the first target component for a test and analysis.

In order to attain the aforementioned object (1), the present invention provides a microchip, formed by bonding at least a first substrate including a groove provided on the substrate surface and a second substrate to each other, having a fluid circuit consisting of the groove and a surface of the second substrate closer to the said first substrate therein, wherein the fluid circuit at least has a separation portion for separating a first component from a fluid containing at least the first component and a second component, the groove constituting the separation portion includes a substantially V-shaped region surrounded by points P1, P2, P3, P4, P5 and P6 arranged clockwise as viewed from the thickness direction of the first substrate, the substantially V-shaped region is a region formed by a flow channel wall W2 having a wall surface passing through the point P2 and the point P3, a flow channel wall W3 having a wall surface passing through the point P3 and the point P4, a flow channel wall W4 having a wall surface passing through the point P4 and the point P5, a flow channel wall W5 having a wall surface passing through the point P5 and the point P6, and a flow channel wall W6 having a wall surface passing through the point P6 and the point P1, and an angle formed by the wall surface of the flow channel wall W2 passing through the point P2 and the point P3 and the wall surface of the flow channel wall W3 passing through the point P3 and the point P4 and an angle formed by the wall surface of the flow channel wall W5 passing through the point P5 and the point P6 and the wall surface of the flow channel wall W6 passing through the point P6 and the point P1 are less than 180 degrees respectively.

A portion having no flow channel wall reaching the aforementioned point P2 from the aforementioned point P1 is an opening for introducing the fluid.

Preferably, the depth of the groove in the aforementioned opening is smaller than the depth of the groove in a region B surrounded by the point P3, the point P4, the point P5 and the point P6, and the groove bottom surface in a region forming a part of a region A surrounded by the point P1, the point P2, the point P3 and the point P6 and including a straight line passing through the point P3 and the point P6 has an inclined structure changing from the depth of the groove in the opening to the depth of the groove in the region B.

Preferably in this microchip, the fluid circuit further has a flow rate limiting portion for limiting the flow rate of the fluid introduced into the separation portion above the aforementioned opening as viewed from the thickness direction of the first substrate. In this case, a groove constituting the flow rate limiting portion is constituted of a linearly extending flow channel wall W7 and a flow channel wall W8 formed to be opposed to the flow channel wall W7. It is preferable that the groove constituting the flow rate limiting portion is formed by a linear wall surface belonging to the flow channel wall W7 and another linear wall surface belonging to the flow channel wall W8, and it is more preferable that the linear wall surface belonging to the flow channel wall W7 and the linear wall surface belonging to the flow channel wall W8 are substantially parallel to each other. Preferably, the flow channel wall W7 extends up to the point P2 positioned in the opening of the aforementioned separation portion.

Preferably, an angle formed by the linear wall surface belonging to the aforementioned flow channel wall W7 and the wall surface of the aforementioned flow channel wall W2 passing through the point P2 and the point P3 is larger than 180 degrees and smaller than 240 degrees.

Preferably, the distance from the point P1 to the point P2 is three to 10 times the distance between the linear wall surface belonging to the aforementioned flow channel wall W7 and the linear wall surface belonging to the aforementioned flow channel wall W8.

Preferably, the specific gravity of the first component is smaller than the specific gravity of the second component.

In order to attain the aforementioned object (2), the present invention provides a microchip, formed by bonding at least a first substrate including a groove provided on the substrate surface and a second substrate to each other, having a fluid circuit consisting of the groove and a surface of the second substrate closer to the first substrate therein, wherein the fluid circuit at least has a separation portion for separating a first component from a fluid, having an opening for introducing the fluid containing at least the first component and a second component, and a flow rate limiting portion arranged above the opening for limiting the flow rate of the fluid introduced into the separation portion, a groove constituting the flow rate limiting portion in the first substrate is formed by a flow channel wall W7 having a linearly extending wall surface a and a flow channel wall W8 having a linearly extending wall surface b substantially parallel to the wall surface a an angle θ4 formed by a wall surface c, belonging to the flow channel wall W8, on the side of the aforementioned opening and the wall surface a satisfies 90 degrees<θ4<180 degrees, and the following expression (1) is satisfied assuming that L1 represents the distance between the wall surface a and the wall surface b, L2 represents the width of the opening and R represents the radius of curvature of a corner portion of the flow channel wall W8 formed by the wall surface b and the wall surface c:

$$2 \times (L1+R) < L2 \tag{1}$$

Preferably, the radius R of curvature satisfies 0<R≦0.25 mm. Preferably, the angle θ4 satisfies 130 degrees≦θ4<180 degrees.

It is preferable that the flow rate limiting portion is arranged immediately above the opening of the separation portion, and it is more preferable that an end of the opening is arranged on the wall surface a belonging to the aforementioned flow channel wall W7.

Preferably in the first substrate, the depth of the groove constituting the flow rate limiting portion is smaller than the depth of the groove constituting a lower portion of the flow rate limiting portion.

Preferably, the specific gravity of the first component is smaller than the specific gravity of the second component.

The inventor has found that a centrifugation portion for separating a target component in a specimen and an unnecessary nontarget component from each other by centrifugation may have a structure including two portions, i.e., a portion (first storage portion) for storing the target component and another portion (second storage portion) for mainly storing the nontarget component and two openings may be given to the centrifugation portion, in order to attain the aforementioned object (3).

The inventor has also found that, when moving the target component in the first storage portion to a measuring portion by applying centrifugal force and measuring the same, the target component in the first storage portion can be inhibited from moving toward the direction of the second storage portion and the target component can be introduced into the measuring portion in a quantity sufficient for filling up the measuring portion by separately connecting another flow channel to a connectional position between a flow channel connecting the first storage portion and the second storage portion with each other and the second storage portion so that gas (air) can be introduced into the connectional position.

In other words, the present invention provides a microchip, formed by bonding at least a first substrate including a groove on the surface and a second substrate to each other, having a fluid circuit formed by the groove and a surface of the second substrate closer to the first substrate therein, wherein the fluid circuit includes a centrifugation portion for separating a specimen introduced into the microchip into a target component and a nontarget component by centrifugation, and the centrifugation portion includes a first storage portion, including a first opening for introducing the specimen on an upper portion, for storing the target component separated by centrifugation, a second storage portion, connected to the bottom portion of the first storage portion and including a second opening on a position different from a connectional position with the first storage portion, for mainly storing the nontarget component separated by centrifugation, a first flow channel connected to the second opening, and a waste liquid reservoir connected to another end of the first flow channel, in order to attain the aforementioned object (3).

Preferably, the second storage portion includes a second opening on an upper portion thereof, and the first storage portion, the second storage portion and the first flow channel constitute a substantially U-shaped form.

Preferably in this microchip, the fluid circuit further includes a measuring portion for measuring the separated target component, and the first opening belonging to the first storage portion is connected to the measuring portion.

Preferably, the measuring portion and the waste liquid reservoir are arranged on the same side with respect to the first storage portion and the second storage portion.

The microchip may further comprise a through-hole, passing through the first substrate in the thickness direction, connected to the waste liquid reservoir.

Blood can be listed as the aforementioned specimen, and a blood plasma component can be listed as the target component. In this case, the microchip can be preferably employed for a blood test.

In order to attain the aforementioned object (3), further, the present invention provides a microchip, formed by bonding at least a first substrate including a groove on the surface and a second substrate to each other, having a fluid circuit formed by the groove and a surface of the second substrate closer to the first substrate therein, wherein the microchip has a specimen inlet, penetrating from the surface of the microchip up to the fluid circuit, for introducing a specimen into the fluid circuit, the fluid circuit includes a centrifugation portion for separating the specimen introduced from the specimen inlet into a target component and a nontarget component by centrifugation, and the centrifugation portion includes a first storage portion, including a first opening provided on the side of the specimen inlet for introducing the specimen, for storing the target component separated by centrifugation, a first flow channel connected to a side of the first storage portion opposite to the side of the first opening, a second storage portion, connected to another end of the first flow channel and including a second opening on a position different from a connectional position with the first flow channel, for mainly storing the nontarget component separated by centrifugation, a gas introduction channel whose one end is connected to the connectional position between the first flow channel and the second storage portion and whose another end is connected to a through-port penetrating from the microchip surface up to the fluid circuit, a second flow channel connected to the second opening, and a waste liquid reservoir connected to another end of the second flow channel.

In one preferred embodiment, the aforementioned through-port is the specimen inlet.

Preferably in this microchip, the width of the first flow channel is smaller than the width of the gas introduction channel. Preferably, the second storage portion includes a second opening on the side of the specimen inlet, and the first storage portion, the first flow channel, the second storage portion and the second flow channel constitute a substantially U-shaped form.

Preferably in this microchip, the fluid circuit further includes a measuring portion for measuring the separated target component, and the first opening belonging to the first storage portion is connected to the measuring portion.

Preferably, the measuring portion and the waste liquid reservoir are arranged on the same side with respect to the first storage portion and the second storage portion.

Preferably, the gas introduction channel is arranged on a side opposite to the side on which the measuring portion and the waste liquid reservoir are arranged with respect to the first storage portion and the second storage portion.

Blood can be listed as the aforementioned specimen, and a blood plasma component can be listed as the target component. In this case, the microchip can be preferably employed for a blood test.

The inventor has found that a centrifugation portion for separating the first target component and the second target component in a specimen from each other by centrifugation may have a structure including two portions, i.e., a storage portion for storing the second target component and a measuring portion for mainly storing the first target component and at least two openings may be given to the centrifugation portion, in order to attain the aforementioned object (4).

As to the centrifugation portion, the inventor has also found that the first target component and the second target component can be simultaneously extracted, for example, by adjusting the form of a wall surface forming the storage portion and the form of a wall surface forming the measuring portion.

In other words, the present invention provides a microchip, formed by bonding at least a first substrate including a groove provided on the substrate surface and a second substrate to each other, having a fluid circuit consisting of the groove and a surface of the second substrate closer to the first substrate therein, wherein the microchip has a specimen inlet, penetrating from one surface thereof up to the fluid circuit, for introducing a specimen into the fluid circuit, the fluid circuit includes a centrifugation portion for separating the specimen into a first target component and a second target component by centrifugation, and the centrifugation portion includes a storage portion, constituted of a wall surface formed in a U-shaped manner, having an opening provided on the side of the specimen inlet and narrowed, a measuring portion, provided in a specimen inlet-side direction of the opening, connected with the storage portion through the opening, a first wall surface arranged along inner walls forming the measuring portion and the storage portion up to a portion of the storage portion inward beyond the opening so that an end portion is not in contact with the inner wall of the storage portion, a first flow channel formed by the inner wall forming the storage portion and the first wall surface, a second wall surface arranged along another-side inner wall forming the measuring portion up to the opening in the storage portion, a second flow channel formed by the inner wall forming the measuring portion and the second wall surface, a specimen introducing portion formed by the second wall surface and the first wall surface, and a third flow channel formed between an end portion of the second wall surface and the first wall surface for connecting the specimen inlet and the inner part of the storage portion with each other, in order to attain the aforementioned object (4).

Preferably, the microchip further comprises a first calibration portion calibrating the first target component and a second calibration portion calibrating the second target component, the specimen introducing portion and the first flow channel are connected to the first calibration portion, and the second flow channel is connected to the second calibration portion.

Preferably, the width of the second flow channel is smaller than the width of the first flow channel. Preferably, the first flow channel is connected to an air hole coupling an external portion of the microchip and the fluid circuit with each other.

Preferably, the interface where the first target component and the second target component are separated from each other is set to be formed on the opening in the storage portion.

Preferably, the inner wall of the storage portion along which the first wall surface is arranged is bent in an L-shaped manner.

Blood can be listed as the aforementioned specimen, and a blood plasma component can be listed as the target component. In this case, the microchip can be preferably employed for a blood test. However, the microchip can similarly perform detection/analysis etc. not only on blood but also on a specimen in which substances different in specific gravity from each other are mixed.

In order to attain the aforementioned object (5), the inventor has noted the form of a centrifugation portion for separating a first target component and a second target component in a specimen from each other by centrifugation and a direction for applying centrifugal force to a microchip, and conducted deep studies. The inventor has found that only the second target component can be extracted by a quantity necessary for a test in the microchip, for example, by adjusting the form of a wall forming the centrifugation portion.

In other words, the present invention provides a microchip, formed by bonding at least a first substrate including a groove provided on the substrate surface and a second substrate to each other, having a fluid circuit formed by the groove and a surface of the second substrate closer to the first substrate therein, wherein the microchip has a specimen inlet, penetrating from one surface thereof up to the fluid circuit, for introducing a specimen into the fluid circuit, the fluid circuit includes a centrifugation portion for separating the specimen into a first target component and a second target component larger in specific gravity than the first target component by centrifugation by applying centrifugal force to the microchip in a first direction, and the centrifugation portion removes the first target component and a partial second target component while holding the rest of the second target component by applying centrifugal force in a second direction after applying the centrifugal force to the microchip in the first direction, and discharges the rest of the second target component from the centrifugation portion by applying centrifugal force in a third direction after applying the centrifugal force to the microchip in the second direction, in order to attain the aforementioned object (5).

Preferably in this microchip, the centrifugation portion includes a storage portion consisting of a space formed by a substantially U-shaped wall to have a narrowed opening for storing only the second target component, and an induction wall extending in a direction separating from the storage portion to be 0 to 90 degrees with respect to the second direction is connected to an end of the substantially U-shaped wall.

Preferably, an internal angle formed by the first direction and the second direction is 45 to 135 degrees, and an internal angle formed by the second direction and the third direction is 135 to 225 degrees.

Preferably, the microchip further has an auxiliary wall for introducing the specimen into the centrifugation portion from one direction in the vicinity of the induction wall.

Preferably, the average depth of the storage portion is larger than the average depth of the remaining portions.

Preferably in this microchip, the introducing quantity of the specimen is adjusted and employed in response to the mixing ratio of the first target component and the second target component in the specimen.

Blood can be listed as the aforementioned specimen, and a blood plasma component can be listed as the target component. In this case, the microchip can be preferably employed for a blood test. However, the microchip can similarly perform detection/analysis etc. not only on blood but also on a specimen in which substances different in specific gravity from each other are mixed.

In order to attain the aforementioned object (6), the inventor has noted the form of a centrifugation portion for centrifuging a specimen and separating the same into a first target component and a second target component.

In other words, the present invention provides a microchip, formed by bonding at least a first substrate including a groove provided on the substrate surface and a second substrate to each other, having a fluid circuit formed by the groove and a surface of the second substrate closer to the first substrate therein, wherein the microchip has a specimen inlet, penetrating from one surface thereof up to the fluid circuit, for introducing a specimen into the fluid circuit, the fluid circuit includes a centrifugation portion for separating the specimen into a first target component and a second target component larger in specific gravity than the first target component by centrifugation by applying centrifugal force to the microchip in a first direction, for discharging only the first target component from the centrifugation portion by applying centrifugal force in a second direction after applying the centrifugal force to the microchip in the first direction, and the rest of the specimen is held in the centrifugation portion after applying centrifugal force in a third direction after applying the centrifugal force to the microchip in the second direction, in order to attain the aforementioned object (6).

Preferably in this microchip, the centrifugation portion includes a storage portion consisting of a space formed by a substantially U-shaped wall to have a narrowed opening, a first wall extending in a direction separating from the storage portion so that an internal angle $\theta 1$ with respect to the second direction is 30 to 60 degrees (where it is assumed that $\theta 1$ represents an internal angle of not more than 90 degrees) is connected to an end of the substantially U-shaped wall, and the microchip includes a second wall arranged up to a substantially U-shaped wall bottom portion in the storage portion along the inner wall surface of the first wall and an inner wall surface forming the storage portion and not in contact with the inner wall forming the storage portion.

Preferably, the inner wall surface of the storage portion along which the second wall is arranged is bent in a substantially L-shaped manner or in a substantially C-shaped manner.

Preferably, the interface where the first target component and the second target component are separated from each other is formed on a side closer to the storage portion than the opening in the centrifugation portion.

Preferably in this microchip, an internal angle $\theta 2$ formed by the first direction and the second direction is 30 to 90 degrees (where it is assumed that $\theta 2$ represents an internal angle of not more than 90 degrees), and an internal angle $\theta 3$ formed by the second direction and the third direction is 30 to 150 degrees (where it is assumed that $\theta 3$ represents an internal angle less than 180 degrees).

Preferably in this microchip, the introducing quantity of the specimen is adjusted and employed in response to the mixing ratio of the first target component and the second target component in the specimen.

According to the present invention, a microchip (microchip for a blood test, for example) capable of extracting a pure first component from a fluid (blood, for example) containing the first component (blood plasma component, for example) and a second component (blood cell component, for example) without mixing the second component and capable of performing correct and reliable test/analysis as to the extracted first component is provided.

According to the present invention, the liquid width of the fluid can be sufficiently narrowed when introducing the fluid into a separation portion (blood plasma separation portion, for example) for separating the first component and the second component from each other. Thus, the separation portion can be reliably filled up with the fluid, whereby correct and reliable test/analysis can be conducted.

According to the microchip of the present invention, the separated liquid (part of the target component and/or the nontarget component) separated by centrifugation does not flow out by subsequent application of centrifugal force, and gas (air) can be prevented from remaining in centrifugation, whereby measurement of the target component can be correctly performed. Therefore, correctness and reliability of the test/analysis with the microchip can be improved.

According to the microchip of the present invention provided with the gas introduction channel, the separated liquid (part of the target component stored in the second storage portion by centrifugation and/or the nontarget component) separated by centrifugation does not flow out by subsequent application of centrifugal force, and gas (air) can be prevented from remaining in centrifugation, whereby measurement of the target component can be correctly performed. Further, the target component can be effectively inhibited from being pulled and moved in the second storage portion direction (waste liquid reservoir direction) by application of centrifugal force for introducing the target component in the first storage portion into the measuring portion, whereby the target component can be introduced into the measuring portion in a quantity sufficient for filling up the measuring portion. Therefore, correctness and reliability of the test/analysis with the microchip can be improved.

According to the microchip of the present invention, the first target substance and the second target substance can be separated from each other and both can be simultaneously detect/analyzed in the specimen in which the first target substance and the second target substance different in specific gravity from each other are mixed, such as blood in which a blood plasma and a blood cell are mixed, for example.

According to the microchip of the present invention, the first target component and the second target component can be separated from each other and the second target component can be precisely measured and detected/analyzed in the specimen in which the first target component and the second target component different in specific gravity from each other are mixed, such as blood in which a blood plasma and a blood cell are mixed, for example.

According to the microchip of the present invention, the first target component can be reliably tested/analyzed in the specimen in which the first target component and the second target component larger in specific gravity than the first target component are mixed.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 4A, 4B, 4C and 4D are schematic flow diagrams showing a flow from a step of introducing blood into the blood plasma separation portion up to a step of extracting the blood plasma component.

FIGS. 5A, 5B and 5C are schematic diagrams showing the relation between an angle θ4 formed by a wall surface c and another wall surface a and the liquid width of blood passing through a flow rate limiting portion.

FIGS. 6A and 6B are schematic diagrams showing the relation between a radius R of curvature of a corner portion of a flow channel wall W8 formed by a wall surface b and the wall surface c and the liquid width of the blood passing through the flow rate limiting portion.

DESCRIPTION OF THE PREFERRED EMBODIMENTS

First Embodiment

Figure 1:
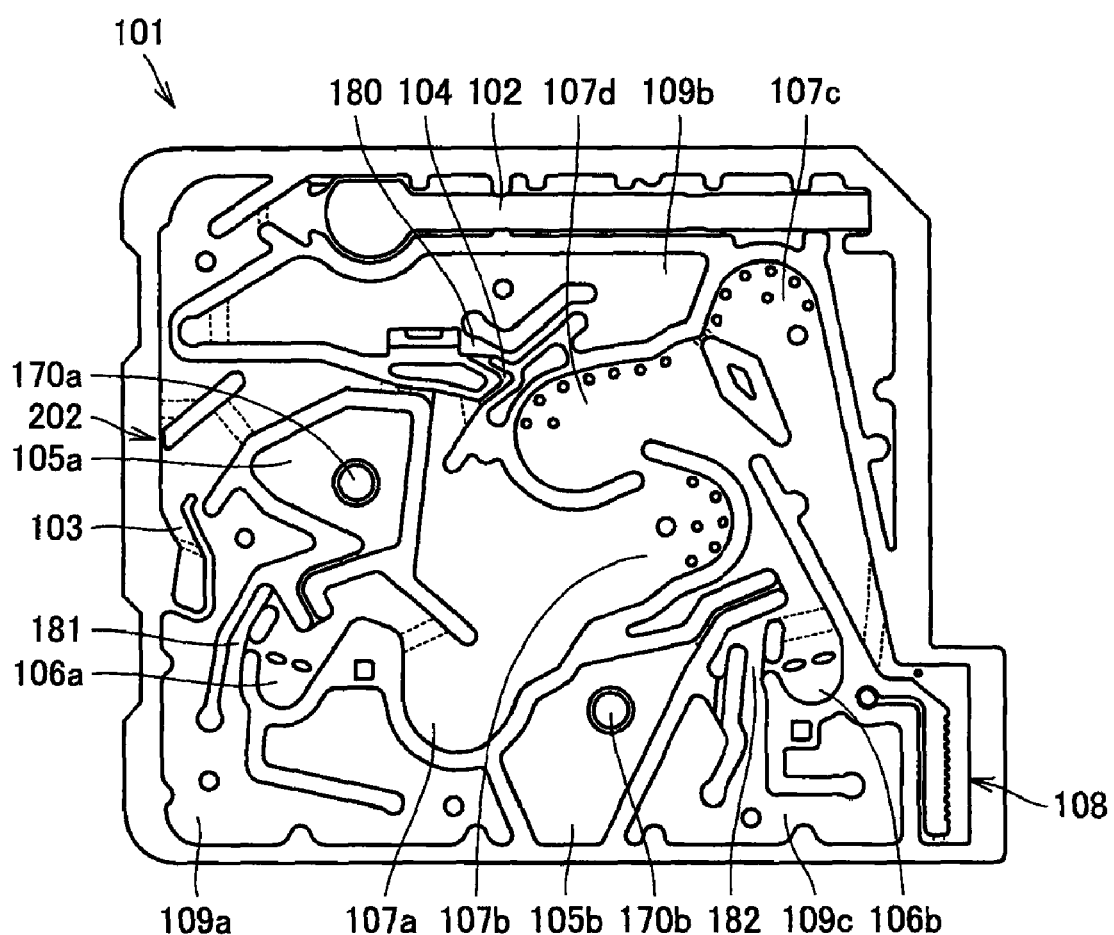
FIG. 1 is a top plan view showing an example of a first substrate constituting a microchip according to a first embodiment of the present invention.

A microchip according to this embodiment relates to a microchip having a fluid circuit therein, formed by bonding a second substrate onto a groove forming-side surface of a first substrate including a groove on the substrate surface. The fluid circuit is constituted of the groove formed on the surface of the first substrate and a bonded surface of the second substrate, and more specifically, the fluid circuit consists of a cavity portion constituted of the groove formed on the surface of the first substrate and the bonded surface of the second substrate. The dimensions of the microchip, not particularly restricted, can be set to about several cm in length and width and about several mm to 1 cm in thickness, for example.

In this embodiment, grooves may be provided on both surfaces of the first substrate, and in this case, the microchip is prepared by bonding the second substrate and a third substrate to hold the first substrate therebetween. The microchip employing such three substrates has two-layer fluid circuits including a fluid circuit constituted of a groove formed on the side of the first substrate closer to the second substrate and a bonded surface of the second substrate and another fluid circuit constituted of a groove formed on a side of the first substrate closer to the third substrate and a bonded surface of the third substrate. The two layers mean that the fluid circuits are provided on two positions different from each other in relation to the thickness direction of the microchip. Such two-layer fluid circuits can be connected with each other by a through-hole passing through the first substrate in the thickness direction.

A method of forming the groove constituting the fluid circuit on the surface of the first substrate is not particularly restricted, but injection molding employing a mold having a transfer structure or imprinting can be listed. When forming the substrate with an inorganic material, etching or the like can be employed.

In the microchip according to this embodiment, the fluid circuit includes at least a separation portion. The separation portion is a portion for separating/removing a second component and extracting a first component from a fluid (liquid, for example) containing the first component and the second component different therefrom. While the types of the first component and the second component separated from each other by the microchip according to this embodiment are not particularly restricted but various components can be efficiently separated according to the microchip of this embodiment, the specific gravity of the first component to be extracted is preferably smaller than the specific gravity of the removed second component.

Such a microchip according to this embodiment can be preferably employed as a microchip for a blood test, for example, and in this case, the aforementioned separation portion can be utilized as a blood plasma separation portion for separating/removing a blood cell component (second component) and extracting a blood plasma component (first component) from blood introduced into the fluid circuit. The extracted blood plasma component is subjected to a necessary treatment in the fluid circuit, so that test/analysis is conducted.

Preferably in the microchip according to this embodiment, the fluid circuit includes a flow rate limiting portion arranged above an opening of the separation portion for limiting the flow rate and the liquid width of the fluid (blood, for example) introduced into the separation portion. Such a flow rate limiting portion is so provided that the liquid width of the fluid introduced into the separation portion can be sufficiently narrowed, whereby the aforementioned clogging phenomenon can be eliminated, and the separation portion can be reliably filled up with the fluid.

The aforementioned fluid circuit may have other portions, in addition to the separation portion (blood plasma separation portion, for example) and the flow rate limiting portion. While other portions are not particularly restricted, a liquid reagent holding portion for holding a liquid reagent, a specimen measuring portion for measuring the extracted first component (blood plasma component, for example), a liquid reagent measuring portion for measuring the liquid reagent, a mixing portion for mixing the measured liquid reagent and the first component with each other, a detecting portion for conducting test/analysis (detection of a specific component in the mixed liquid, for example) as to the mixed liquid and the like can be listed. A further portion may be provided if necessary. This test/analysis, not particularly restricted, can be performed by optical measurement such as a method of applying light to the detecting portion and detecting the intensity (transmittance) of transmitted light; or a method of measuring an absorption spectrum as to the mixed liquid held in the detecting portion, for example. In this embodiment, the liquid reagent is a reagent treating the specimen (first component) subjected to the test/analysis conducted with the microchip or mixed or reacted with the specimen, and previously stored in the liquid reagent holding portion of the fluid circuit before the use of the microchip in general.

The respective portions in the aforementioned fluid circuit are arranged on proper positions and connected with each other through a fine channel, so that measurement of the first component and the liquid reagent, mixing of the first component and the liquid reagent, introduction of the obtained mixed liquid into the detecting portion and test/analysis of the mixed liquid can be successively performed, for example. Application of centrifugal force to the microchip is typically performed by placing the microchip on an apparatus (centrifugal apparatus) capable of applying centrifugal force thereto. The microchip according to this embodiment is now described in more detail.

FIG. 1 is a top plan view (an upper surface) of a first substrate 101 constituting a microchip 100 which is an example of the microchip according to the present invention. Here, "upper surface" denotes a surface on a side provided with a groove forming a fluid circuit. It is assumed that "lower surface" denotes a surface on a side not provided with the groove forming the fluid circuit. Microchip 100 is formed by bonding a second substrate (not shown) onto a groove forming-side surface (upper surface) of a first substrate 101, which is a transparent substrate, having a groove formed on the substrate surface and a through-hole penetrating in the thickness direction of the substrate, as shown in FIG. 1. The fluid circuit is constituted of the groove formed on the surface (upper surface) of first substrate 101 and a bonded surface of the second substrate. Microchip 100 has a fluid circuit structure preferably applicable as a microchip removing a blood cell component and extracting a blood plasma component from blood and conducting test/analysis as to the blood plasma component.

Referring to FIG. 1, the fluid circuit belonging to microchip 100 is mainly constituted of a sample tube receiving portion 102 for incorporating a sample tube such as a capillary containing blood collected from a subject, a flow rate limiting portion 202 adjusting the flow rate and the liquid width of the blood derived from the sample tube, a blood plasma separation portion 103 for removing a blood cell component and extracting a blood plasma component from the blood, a specimen measuring portion 104 for measuring the separated blood plasma component, two liquid reagent holding portions 105a and 105b for holding a liquid reagent, liquid reagent measuring portions 106a and 106b for measuring the liquid reagent, mixing portions 107a, 107b, 107c and 107d for mixing the blood plasma component and the liquid reagent with each other, and a detecting portion 108 in which test/analysis as to the obtained mixed liquid is conducted. Microchip 100 is such a "liquid reagent containing type microchip" that the liquid reagent is previously contained in the fluid circuit, and the liquid reagent is injected from the side of the lower surface (first substrate 101-side surface in microchip 100) of first substrate 101 through liquid reagent inlets 170a and 170b, which are through-holes penetrating in the thickness direction of first substrate 101, formed on liquid reagent holding portions 105a and 105b. Openings of these liquid reagent inlets are sealed by bonding a sealing label or the like to the lower surface (first substrate 101-side surface in microchip 100) of first substrate 101.

(Separation Portion)

Figure 2:
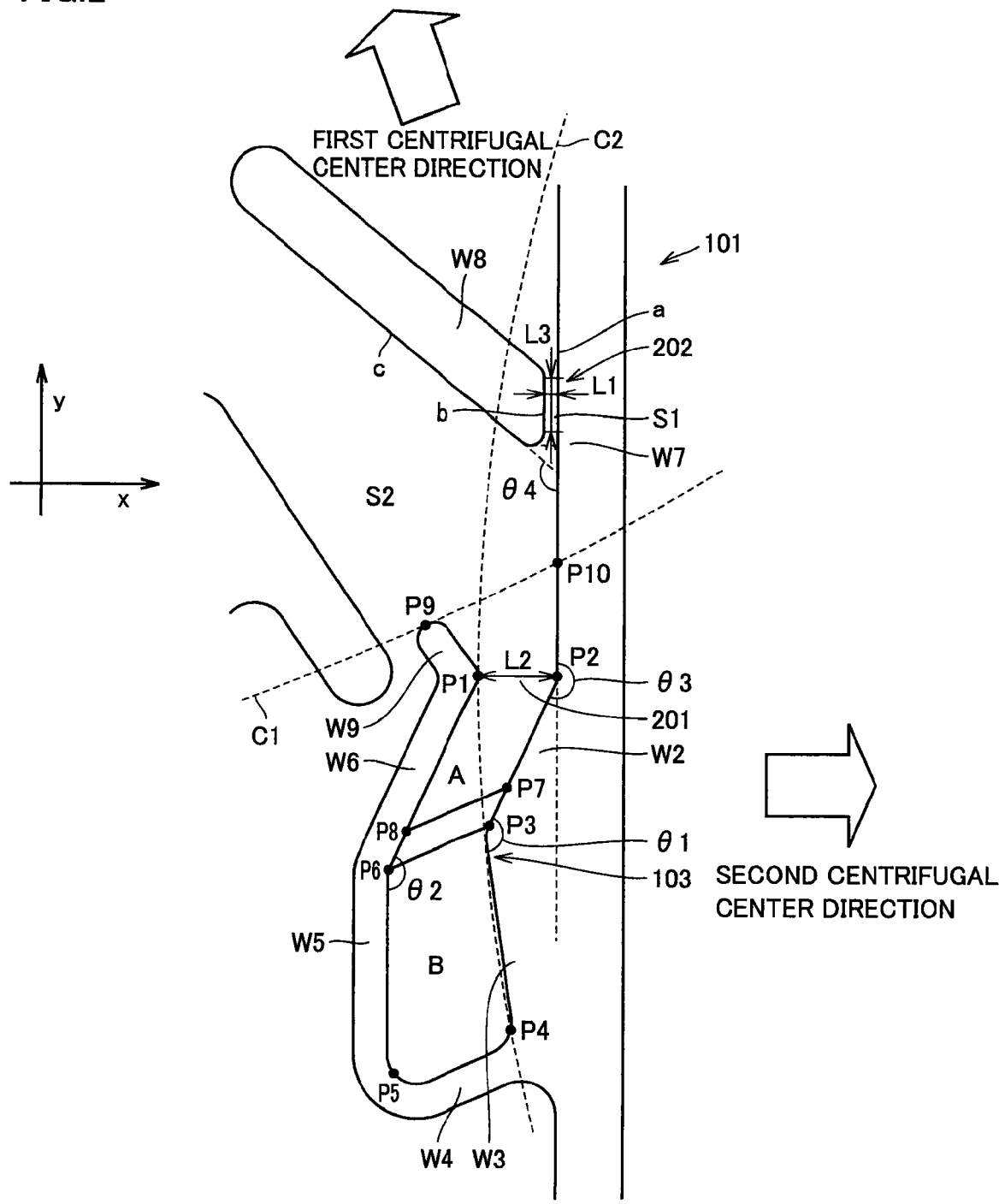
FIG. 2 is an enlarged diagram showing a peripheral region of a blood plasma separation portion shown in FIG. 1.

Blood plasma separation portion 103 which is the separation portion according to this embodiment is described in detail. FIG. 2 is an enlarged view showing a peripheral region of blood plasma separation portion 103 shown in FIG. 1, as viewed from the side of the lower surface (first substrate 101-side surface in microchip 100) of first substrate 101. Microchip 100 has blood plasma separation portion 103 for removing the blood cell component and extracting the blood plasma component from the blood introduced into the fluid circuit. This embodiment is characterized in that blood plasma separation portion 103 includes a substantially V-shaped region surrounded by points P1, P2, P3, P4, P5 and P6 arranged clockwise as viewed from the thickness direction of first substrate 101, as shown in FIG. 2. The substantially V-shaped region formed by points P1 to P6 is a region surrounded by a flow channel wall W2 having a wall surface passing through point P2 and point P3, a flow channel wall W3 having a wall surface passing through point P3 and point P4, a flow channel wall W4 having a wall surface passing through point P4 and point P5, a flow channel W5 having a wall surface passing through point P5 and point P6, and a flow channel wall W6 having a wall surface passing through point P6 and point P1, and a region, reaching point P2 from point P1, provided with no flow channel wall forms an opening 201 of blood plasma separation portion 103.

Figure 3:
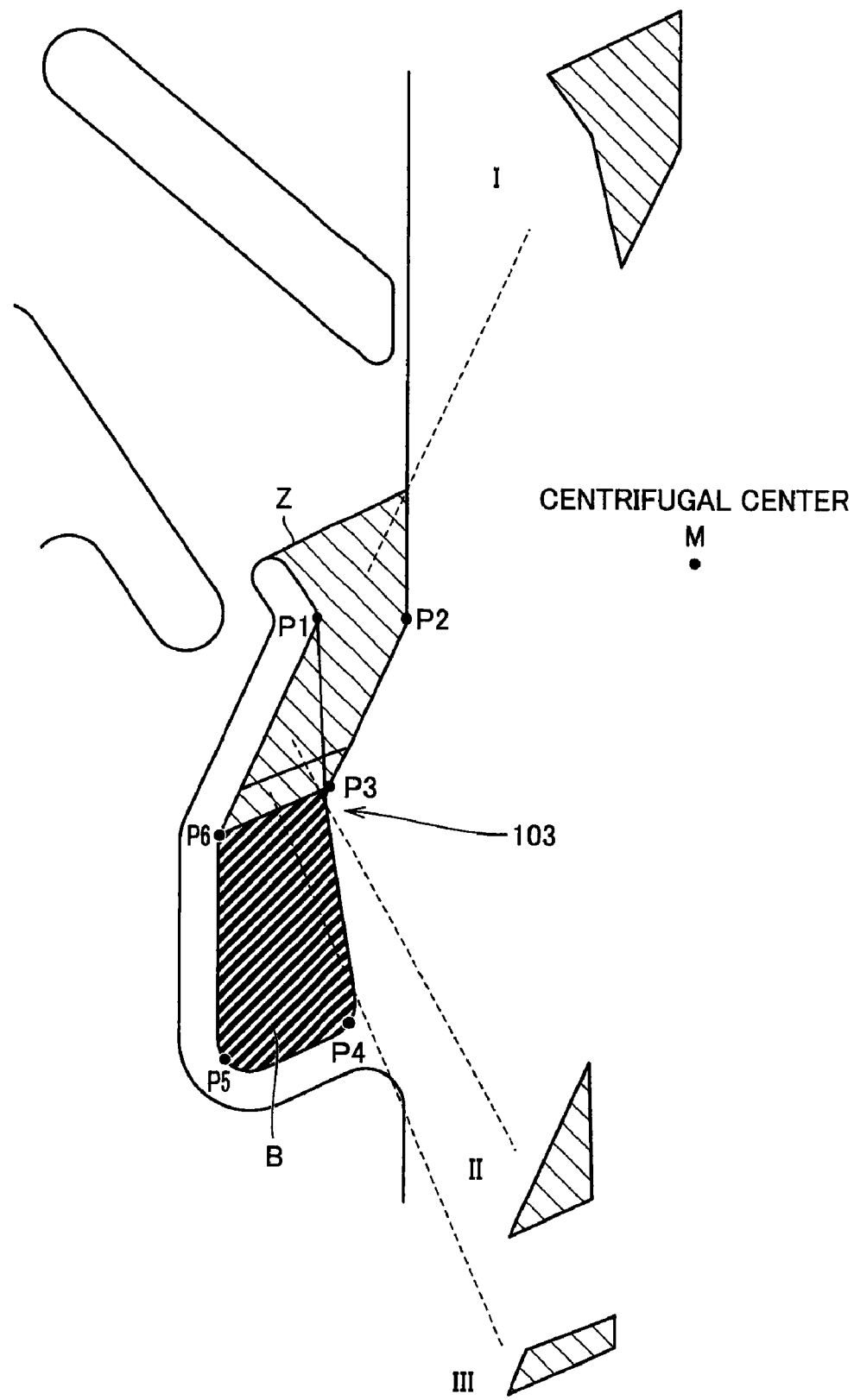
FIG. 3 is a schematic diagram showing a state where blood is introduced into the blood plasma separation portion shown in FIG. 1 and separated into a layer of a blood plasma component and a layer of a blood cell component by centrifugation.

FIG. 3 is a schematic diagram showing a state where the blood is introduced into blood plasma separation portion 103 and separated into a layer of a blood plasma component and a layer of a blood cell component by centrifugation. FIG. 3 shows such an example that the interface between the layer of the blood plasma component and the layer of the blood cell component is positioned on a straight line coupling point P3 and point P6 with each other. This interface may be present under the straight line coupling point P3 and point P6 with each other. It follows that the blood cell component larger in specific gravity occupies a region B formed by points P3, P4, P5 and P6 (i.e., a lower region of blood plasma separation portion 103) by centrifugation. The blood plasma component occupies an upper region of blood plasma separation portion 103, and the level thereof is a level Z shown in FIG. 3.

In order to extract only the blood plasma component from the blood layer-separated into the layer of the blood plasma component and the layer of the blood cell component in this manner, microchip 100 is rotated around a centrifugal center M in FIG. 3, and leftward centrifugal force in FIG. 3 is applied, for example. In microchip 100, the form of blood plasma separation portion 103 is substantially V-shaped, and hence only the blood plasma component in a region I in FIG. 3 in the layer-separated blood plasma component is discharged from blood plasma separation portion 103 while the blood plasma component in regions II and III remains in blood plasma separation portion 103. At this time, the blood cell component in region B positioned under the remaining blood plasma component is not discharged by the application of the leftward centrifugal force. In other words, the form of the blood plasma separation portion is so rendered substantially V-shaped that the separated blood cell component is not mixed when the layer-separated blood plasma component is extracted and hence a pure blood plasma component can be extracted.

FIGS. 4A, 4B, 4C and 4D are schematic flow diagrams showing a flow from the step of introducing the blood into blood plasma separation portion 103 up to the step of extracting the blood plasma component. First, referring to FIGS. 4A and 4B, the blood is introduced into blood plasma separation portion 103 through flow rate limiting portion 202 (this is described later) by applying centrifugal force G to the microchip in the illustrated direction. Excess blood overflowing blood plasma separation portion 103 is stored in a waste liquid reservoir portion (not shown in FIGS. 4A to 4D. Waste liquid reservoir portion 109a in FIG. 1) through a flow channel connected to blood plasma separation portion 103. Then, referring to FIG. 4C, centrifugation is performed by further applying centrifugal force G to the microchip in the illustrated direction, to separate the blood into the blood plasma component and the blood cell component. Finally, referring to FIG. 4D, centrifugal force G is applied to the microchip in the illustrated direction, thereby discharging part of the layer-separated blood plasma component from blood plasma separation portion 103 and extracting the pure blood plasma component into which no blood cell component is mixed. The centrifugal force in the direction illustrated in FIGS. 4A to 4C can be obtained by rotating the microchip around a centrifugal center N in FIG. 1, for example.

A preferred structure of the blood plasma separation portion is now described in further detail with reference to FIG. 2. In this embodiment, the blood plasma separation portion has the substantially V-shaped form as hereinabove described, and more specifically, an angle θ1 formed by the wall surface of flow channel wall W2 passing through point P2 and point P3 and the wall surface of flow channel wall W3 passing through point P3 and point P4 and an angle θ2 formed by the wall surface of flow channel wall W5 passing through point P5 and P6 and the wall surface of flow channel wall W6 passing through point P6 and point P1 are less than 180 degrees respectively. It is preferable to introduce the blood along flow channel wall W3 in order not to inhibit extrusion of air, and hence θ1 preferably satisfies about 120 degrees<θ1. Clogging easily takes place when the width of region B is narrower than the distance between point P3 and point P6, and hence θ2 preferably satisfies θ2≧θ1. Assuming that R' represents the radius of the following arc C2, θ1 and the following θ3 preferably satisfy the relation of the following expression:

$$\cos \theta 1 = (R'-L2) \times \cos \theta 3 / R$$

While arc C2 in FIG. 2 is an arc of a circle centering on a centrifugal center (second centrifugal center) for providing centrifugal force (leftward centrifugal force in FIG. 2) applied when discharging part of the blood plasma component from blood plasma separation portion 103 and passing through point P1, aforementioned point P3 is preferably positioned on arc C2 or in the vicinity thereof, or a side farther from the centrifugal center than arc C2 (to have an x-coordinate smaller than the x-coordinate of any point on arc C2 when employing x-coordinates shown in FIG. 2). When point P3 is positioned on a side remarkably closer to the second centrifugal center than arc C2, there is a possibility that the layer-separated blood cell component is mixed in extraction of the blood plasma component.

While the position of point P2 is not particularly restricted, it is preferable to have a y-coordinate identical to the y-coordinate of point P1 or smaller than the same.

Blood plasma separation portion 103 may be provided with a flow channel wall W9 having a forward end on a point P9, as shown in FIG. 2. Flow channel wall W9 is so provided that the quantity of the extracted blood plasma component can be adjusted in response to the position of point P9. The position of point P9 is preferably so set as to be identical to the x-coordinate of point P1 or smaller than this. If the x-coordinate of point P9 is larger than the x-coordinate of point P1, it follows that the quantity of the blood plasma component remaining in blood plasma separation portion 103 increases in extraction of the blood plasma component.

The position of point P6 is not particularly restricted but can be so arranged that a straight line coupling point P3 and point P6 with each other is substantially parallel to a level formed by the blood introduced into blood plasma separation portion 103, for example. The level formed by the blood introduced into blood plasma separation portion 103 is present on an arc C1 of a circle centering on a centrifugal center (first centrifugal center) for providing centrifugal force applied when introducing the blood into blood plasma separation portion 103 and passing through point P9, and more specifically, this is an arc reaching a point P10 from point P9 in FIG. 2.

The blood is preferably introduced along flow channel wall W3 in order not to inhibit extrusion of air and hence flow channel wall W3 is preferably so arranged that the wall surface passing through point P3 and point P4 is positioned substantially on arc C2 or on the left side (−x side) of arc C2, while the present invention is not restricted to this. Flow channel wall W5 is preferably so arranged that the distance between the wall surface passing through point P3 and point P4 and the wall surface passing through point P5 and point P6 is identical to the distance between point P3 and point P6 or larger than the same. The positions of flow channel walls W3, W4 and W5 are preferably decided in consideration of the quantity of the blood cell component stored in blood plasma separation portion 103 (i.e., the hematocrit of the blood introduced into blood plasma separation portion 103). When constituting a blood plasma separation portion capable of coping with a hematocrit of not more than 60%, for example, flow channel walls W3, W4 and W5 are so arranged that the volume of a space formed by flow channel walls W3, W4 and W5 is 60% of the quantity of the blood introduced into blood plasma separation portion 103.

The depth of the groove in opening 201 (depth of the groove in a region surrounded by points P2, P7, P8 and P1, for example) is preferably rendered smaller than the depth of the groove in region B surrounded by points P3, P4, P5 and P6, and in this case, the groove bottom surface in a region surrounded by points P7, P3, P6 and P8 preferably has an inclined structure changing from the depth of the groove in the aforementioned opening up to the depth of the groove in aforementioned region B. Thus, the groove bottom surface of blood plasma separation portion 103 is brought into a step structure coupled by the inclined structure and the groove in region B which is a region in which the blood cell component is stored is rendered larger, so that the blood cell component can be more effectively prevented from mixing when extracting the layer-separated partial blood plasma component. The positions of points P7 and P8, i.e., the area of the region (region surrounded by points P7, P3, P6 and P8) having the inclined structure occupying region A surrounded by points P1, P2, P3 and P6 is not particularly restricted, but part of region A including a straight line passing through point P3 and point P6 may have the inclined structure.

(Flow Rate Limiting Portion)

In the microchip according to this embodiment, a flow rate limiting portion for limiting the flow rate of the blood introduced into blood plasma separation portion 103 is preferably provided above blood plasma separation portion 103 (preferably immediately above the blood plasma separation portion), as shown in FIG. 2. The flow rate limiting portion may have a structure such as the structure of flow rate limiting portion 202 shown in FIG. 2, for example. In other words, a groove constituting flow rate limiting portion 202 can be constituted of a flow channel wall W7 having a linearly extending wall surface and a flow channel wall W8, having a linearly extending wall surface, formed to be opposed to flow channel wall W7. The linear wall surface belonging to flow channel wall W7 and the linear wall surface belonging to flow channel wall W8 are preferably substantially parallel to each other.

The distance (width of flow rate limiting portion 202) L1 between the linear wall surface belonging to flow channel wall W7 and the linear wall surface belonging to flow channel wall W8, not particularly restricted, can be set to about 0.1 to 0.4 mm, for example, and is more specifically about 0.2 mm, for example. Width L1 of flow rate limiting portion 202 is preferably set to about $1/10$ to about $1/3$, more preferably set to about $1/8$ to about $1/3$, and further preferably about $1/8$ or about $1/5$ of the width (distance between point P1 and point P2) L2 of opening 201 of blood plasma separation portion 103. If width L2 of the opening is less than about three times width L1 of flow rate limiting portion 202, the blood fills up the groove in blood plasma separation portion 103 before reaching the bottom portion of blood plasma separation portion 103 and inhibits discharge of air in blood plasma separation portion 103, to easily cause such a phenomenon (clogging phenomenon) that the blood does not fill up blood plasma separation portion 103. If width L2 of the opening exceeds about 10 times width L1 of flow rate limiting portion 202, the volume of blood plasma separation portion 103 so increases that a larger quantity of blood is required in order to fill up blood plasma separation portion 103.

The length L3 of flow rate limiting portion 202 is not particularly restricted either, but can be set to about 0.8 to 2.0 mm, for example.

Flow channel wall W7 preferably extends up to point P2 which is the right end of opening 201 of blood plasma separation portion 103. In other words, flow channel wall W7 couples with flow channel wall W2 on point P2 in this case, and it follows that the right end of blood plasma separation portion 103 is positioned immediately under flow rate limiting portion 202 formed by the linear wall surface belonging to flow channel wall W7 and the linear wall surface belonging to flow channel wall W8. According to this structure, the flow rate and the liquid width of the blood passing through flow rate limiting portion 202 are reduced, whereby the blood can be efficiently introduced into blood plasma separation portion 103 without causing the aforementioned clogging phenomenon.

In the case where flow channel wall W7 extends up to point P2 which is the right end of opening 201 of blood plasma separation portion 103, an angle θ3 (see FIG. 2) formed by the linear wall surface belonging to flow channel wall W7 and the wall surface of flow channel wall W2 passing through point P2 and point P3 is preferably larger than 180 degrees and smaller than 240 degrees. More preferably, the angle is at least 190 degrees and not more than 210 degrees. If θ3 is at least 240 degrees, the speed of the blood colliding with the wall surface passing through point P2 and point P3 so abruptly lowers that the liquid forward end swells to easily cause the clogging phenomenon. If θ3 is not more than 180 degrees, on the other hand, there is a possibility that the blood cell component mixes when extracting the blood plasma component.

The positions of the grooves constituting blood plasma separation portion 103 and flow rate limiting portion 202 on first substrate 101, not particularly restricted, are preferably so arranged as to be along a sidewall of a peripheral portion of first substrate 101, as shown in FIG. 1. Thus, when centrifugal force is applied in the direction (downward in FIG. 1) for passing the blood through flow rate limiting portion 202 and introducing the same into blood plasma separation portion 103, force in a direction pressed against the sidewall acts on the blood along with the downward force in FIG. 1, whereby the blood can be fed along the sidewall and hence the liquid width of the blood does not excessively spread but the total quantity of the blood introduced into the fluid circuit can be reliably induced into opening 201 of blood plasma separation portion 103. When blood plasma separation portion 103 and flow rate limiting portion 202 are arranged in the aforementioned manner, flow channel wall W7 constituting flow rate limiting portion 202 and flow channel walls W2 and W3 constituting blood plasma separation portion 103 become the sidewall itself.

A more preferred structure of the flow rate limiting portion is now described with reference to FIG. 2. Flow rate limiting portion 202 shown in FIG. 2 is a flow channel formed by a linearly extending wall surface a belonging to flow channel wall W7 which is the sidewall of the peripheral portion of first substrate 101 and a linearly extending wall surface b in flow channel wall W8 arranged to be opposed to flow channel wall W7. In other words, the groove constituting flow rate limiting portion 202 in first substrate 101 is formed by flow channel wall W7 having linearly extending wall surface a and flow channel wall W8 having linearly extending wall surface b parallel to wall surface a. While wall surface b is arranged parallelly to wall surface a of flow channel wall W7 in flow rate limiting portion 202 shown in FIG. 2, the present invention is not restricted to this. Flow channel wall W8 has a wall surface c which is a wall surface closer to opening 201 of blood plasma separation portion 103.

In this embodiment, an angle θ4 formed by wall surface c closer to opening 201 belonging to flow channel wall W8 and wall surface a preferably satisfies 90 degrees<θ4<180 degrees. The setting of angle θ4 formed by wall surface c and wall surface a in this range contributes to narrowing of the liquid width of the blood passing through flow rate limiting portion 202.

FIGS. 5A, 5B and 5C are schematic diagrams showing the relation between angle θ4 formed by wall surface c and wall surface a and the liquid width of the blood passing through the flow rate limiting portion. As shown in FIGS. 5A to 5C, the blood passing through the flow rate limiting portion flows along wall surface c of flow channel wall W8 and hence the liquid width of the blood spreads, if θ4 is 90 degrees (FIG. 5B) or 0 degrees<θ4<90 degrees (FIG. 5C). On the other hand, θ4 is so set to 90 degrees<θ4<180 degrees (FIG. 5A) that the liquid width can be reduced as compared with the cases of FIGS. 5B and 5C. The blood can be more efficiently inhibited from flowing along wall surface c by more approximating the flow direction of the blood and wall surface c to parallelism, and hence θ4 preferably satisfies 130 degrees≦θ4<180 degrees. Also in the case where θ4 is set to 90 degrees<θ4<180 degrees, however, spreading of the liquid width can take place as compared with distance (width of the flow rate limiting portion) L1 between wall surface a and wall surface b, depending on a radius R of curvature of a corner portion of flow channel wall W8 formed by wall surface b and wall surface c.

FIGS. 6A and 6B are schematic diagrams showing the relation between radius R of curvature of the corner portion of flow channel wall W8 formed by wall surface b and wall surface c and the liquid width of the blood passing through the flow rate limiting portion. FIG. 6A is a diagram showing a calculation result on the assumption that radius R of curvature is 500 μm and width L1 of the flow rate limiting portion is 300 μm, and FIG. 6B is a diagram showing a calculation result on the assumption that radius R of curvature is 250 μm and width L1 of the flow rate limiting portion is 300 μm. Referring to FIGS. 6A and 6B, angle θ4 formed by wall surface c and wall surface a is set to 130 degrees. From these calculation results, it is understood that a liquid width L' (distance from wall surface a to an exfoliation point. The exfoliation point denotes a point of the blood farthest from wall surface a on the wall surface of flow channel wall W8 in a case where the blood flows along the wall surface of flow channel wall W8 and spreads in a direction separating from wall surface A) of the blood having passed through the flow rate limiting portion can be more narrowed by reducing radius R of curvature.

The inventors have conducted deep studies as to the relation between liquid width L' of the blood having passed through the flow rate limiting portion and width L2 of the opening of the blood plasma separation portion in order to eliminate the aforementioned clogging phenomenon in the blood plasma separation portion, to find that the aforementioned clogging phenomenon can be eliminated by designing the flow rate limiting portion and the blood plasma separation portion to satisfy the following expression (1):

$$2\times(L1+R)<L2 \qquad (1)$$

L1 represents the distance (width of the flow rate limiting portion) between wall surface a and wall surface b, L2 represents the width of the opening of the blood plasma separation portion, and R represents the radius of curvature of the corner portion of flow channel wall W8 formed by wall surface b and wall surface c.

(L1+R) on the left side of the above expression (1) is a numerical value excellently correlating to liquid width L' of the blood having passed through the flow rate limiting portion. Referring to FIGS. 6A and 6B, (L1+R) is calculated as 800 μm and 550 μm respectively, while the calculation results of liquid width L' are 660 μm and 480 μm respectively, for example. Thus, liquid width L' takes a value slightly smaller than (L1+R), while it can be said that (L1+R) excellently reflects liquid width L'.

Therefore, the above expression (1) means that width L2 of the opening of the blood plasma separation portion must be set to a value larger than about twice liquid width L'. The clogging phenomenon can be eliminated by satisfying the conditions of the above expression (1), whereby the blood plasma separation portion can be reliably filled up with the blood. When width L2 of the opening is extremely enlarged with respect to (L1+R), the area occupied by the blood plasma separation portion in the fluid circuit increases although the clogging phenomenon can be eliminated, and hence width L2 of the opening preferably satisfies L2<5×(L1+R).

Further, the above expression (1) indicates that L2 can be more reduced by further reducing L1 and/or R, and hence L1 and R are preferably as small as possible. More specifically, width L1 of the flow rate limiting portion can be set to about 0.1 to 0.4 mm, and is preferably about 0.1 to 0.2 mm. Radius R of curvature is preferably not more than 0.25 mm. While the corner portion of flow channel wall W8 formed by wall surface b and wall surface c ideally has a sharp form (form whose radius of curvature is zero), it is difficult to prepare such a sharp form in a case of forming the groove of the first substrate with a mold. In practice, therefore, radius R of curvature becomes larger than zero. Length L3 of flow rate limiting portion 202 is not particularly restricted, but can be set to about 0.8 to 2.0 mm, for example.

Flow rate limiting portion 202 is arranged above blood plasma separation portion 103, and preferably arranged immediately above the blood plasma separation portion, as shown in FIG. 2. The flow rate limiting portion and the blood plasma separation portion are more preferably so arranged that flow channel wall W7 extends up to point P2 which is the right end of opening 201 of blood plasma separation portion 103 and an end (point P2) of the opening of the blood plasma separation portion is arranged on wall surface a belonging to flow channel wall W7. According to this structure, the blood having passed through flow rate limiting portion 202 can be introduced into blood plasma separation portion 103 along wall surface a.

Referring to FIG. 2, the depth of the groove constituting flow rate limiting portion 202 (region S1) is preferably rendered smaller than the depth of the groove constituting a lower region (region S2) of flow rate limiting portion 202, particularly the depth of the groove in the vicinity of an outlet of flow rate limiting portion 202. Such a step structure is so provided that spreading of the liquid width of the blood which can take place immediately after passing through flow rate limiting portion 202 before reaching the blood plasma separation portion can be absorbed in the depth direction of the substrate, whereby spreading of the liquid width can be more effectively suppressed.

While the material for the first substrate and the second substrate constituting the microchip according to this embodiment is not particularly restricted, resin is preferably employed in consideration of workability. Among resin materials, polystyrene-based resin, a cycloolefin polymer (COP) or acrylic resin is preferably employed, and the polystyrene-based resin is more preferable in particular, since moisture resistance and workability (such as easiness in injection molding) are excellent.

The first substrate is a substrate on whose surface the groove constituting the fluid circuit is formed, as hereinabove described. Such a first substrate, including the site to which detection light is applied in optical measurement, is preferably formed by a transparent substrate, and at least a region of the detecting portion through which the detection light passes must be made of a transparent material such as transparent resin. The second substrate may be formed by either a transparent substrate or an opaque substrate. Bonding between the first substrate and the second substrate can be performed by welding such as laser welding, thermal welding or ultrasonic welding; or bonding with an adhesive, and welding is preferably employed. In the laser welding, for example, bonding is performed by applying a laser to a bonded surface of at least either the first substrate or the second substrate and welding the bonded surface, while an opaque substrate (preferably a black substrate) is so employed as the substrate at this time that light absorbance increases and the laser welding can be efficiently performed. When the first substrate is formed by a transparent substrate, therefore, the second substrate is preferably formed by an opaque substrate, and more preferably formed by a black substrate. When preparing the microchip by providing grooves on both surfaces of the first substrate and bonding the second substrate and the third substrate to hold the first substrate therebetween, on the other hand, the first substrate can be formed by an opaque substrate (preferably a black substrate), and the second and third substrates can be formed by transparent substrates.

Finally, an example of the operating method of microchip 100 is described with reference to FIG. 1. The operating method described below is merely an example, and not restricted to this method. First, the sample tube containing the blood collected from the subject is loaded on sample tube receiving portion 102. Then, centrifugal force is applied to microchip 100 in a leftward direction in FIG. 1 (hereinafter simply referred to as leftward. This also applies to other directions) to extract the blood from the sample tube, and the blood is thereafter introduced into blood plasma separation portion 103 through flow rate limiting portion 202 by downward centrifugal force (rotating microchip 100 around centrifugal center N, for example) and separated into the blood plasma component (upper layer) and the blood cell component (lower layer) by centrifugation performed by continuously applying the downward centrifugal force. At this time, excess blood is stored in waste liquid reservoir 109a. A liquid reagent X in liquid reagent holding portion 105a is introduced into and measured in liquid reagent measuring portion 106a due to this downward centrifugal force. Liquid reagent X overflowing liquid reagent measuring portion 106a is stored in waste liquid reservoir 109a through a channel 181 connected to an outlet-side end portion of liquid reagent measuring portion 106a.

Then, the separated blood plasma component in blood plasma separation portion 103 is introduced into specimen measuring portion 104 by rightward centrifugal force, and measured. The blood plasma component overflowing specimen measuring portion 104 is stored in waste liquid reservoir 109b through a channel 180 connected to an outlet-side end portion of specimen measuring portion 104. Measured liquid reagent X moves to mixing portion 107b, while a liquid reagent Y in liquid reagent holding portion 105b is discharged from liquid reagent holding portion 105b.

Then, the measured blood plasma component and measured liquid reagent X move to mixing portion 107a and are mixed with each other due to the downward centrifugal force. Further, liquid reagent Y is introduced into and measured in liquid reagent measuring portion 106b. Liquid reagent Y overflowing liquid reagent measuring portion 106b is stored in waste liquid reservoir 109c through a channel 182 connected to an outlet-side end portion of liquid reagent measuring portion 106b. Then, rightward centrifugal force, downward centrifugal force and rightward centrifugal force are successively applied to transfer the mixed liquid of the blood plasma component and liquid reagent X between mixing portions 107a and 107b, thereby sufficiently mixing the mixed liquid.

Then, the mixed liquid of the blood plasma component and liquid reagent X and measured liquid reagent Y are mixed with each other in mixing portion 107c by upward centrifugal force. Then, leftward centrifugal force, upward centrifugal force, leftward centrifugal force and upward centrifugal force are successively applied to transfer the mixed liquid between mixing portions 107c and 107d, thereby sufficiently mixing the mixed liquid. Finally, the mixed liquid in mixing portion 107c is introduced into detecting portion 108 by rightward centrifugal force. The mixed liquid stored in detecting portion 108 is subjected to the aforementioned optical measurement, for example, so that test/analysis is conducted.

While the separation portion and the flow rate limiting portion of the microchip according to this embodiment have been described with reference to the microchip shown in FIGS. 1 and 2, the microchip according to this embodiment may have only either the separation portion or the flow rate limiting portion according to the present invention. When the microchip according to this embodiment has only the separation portion according to the present invention, the flow rate limiting portion may not be present, or the microchip may have a flow rate limiting portion irrelevant to the present invention. When the microchip according to this embodiment has only the flow rate limiting portion according to the present invention, the form of the separation portion is not restricted to the form shown in FIG. 2. In order to effectively eliminate the clogging phenomenon by sufficiently narrowing the liquid width of the fluid introduced into the separation portion while making it possible to extract a certain specific component from a fluid containing a large number of components in high purity, however, the microchip preferably has both of the separation portion and the flow rate limiting portion (the blood plasma separation portion and the flow rate limiting portion shown in FIG. 2, for example) according to the present invention.

Second Embodiment

A microchip according to this embodiment is formed by bonding a first substrate including a groove on the substrate surface and a second substrate to each other in one preferred mode. Such a microchip comprises a fluid circuit consisting of a cavity portion constituted of the groove provided on the surface of the first substrate and a first substrate-side surface (bonded surface of the second substrate) of the second substrate therein.

The microchip according to this embodiment is formed by bonding a third substrate, a first substrate including grooves provided on both surfaces of the substrate and a second substrate to each other in this order, in another preferred mode. The microchip consisting of such three substrates comprises two-layer fluid circuits, i.e., a first fluid circuit constituted of grooves provided on a third substrate-side surface of the first substrate and a first substrate-side surface of the third substrate and a second fluid circuit constituted of grooves provided on a second substrate-side surface of the first substrate and a first substrate-side surface of the second substrate. The two layers mean that the fluid circuits are provided on two positions different from each other in relation to the thickness direction of the microchip. The first fluid circuit and the second fluid circuit may be coupled with each other through one or at least two through-holes formed in the first substrate to penetrate in the thickness direction.

The material for each substrate constituting the microchip according to this embodiment is not particularly restricted but an organic material such as polyethylene terephthalate (PET), polybutylene terephthalate (PBT), polymethyl methacrylate (PMMA), polycarbonate (PC), polystyrene (PS), polypropylene (PP), polyethylene (PE), polyethylene naphthalate (PEN), polyallylate resin (PAR), acrylonitrile butadiene styrene resin (ABS), polyvinyl chloride resin (PVC), polymethyl pentene resin (PMP), polybutadiene resin (PBD), a biodegradable polymer (BP), a cycloolefin polymer (COP) or polydimethyl siloxane (PDMS); or an inorganic material such as silicon, glass or quartz can be employed.

A method of forming the grooves constituting the fluid circuits on the surfaces of the first substrate is not particularly restricted, but injection molding employing a mold having a transfer structure or imprinting can be listed. When preparing the substrate from an inorganic material, etching or the like can be employed.

In the microchip according to this embodiment, each fluid circuit (the first fluid circuit and the second fluid circuit when comprising two-layer fluid circuits) includes various portions arranged on proper positions in the fluid circuit to be capable of performing various proper treatments on a fluid (liquid, in particular) in the fluid circuit, and these portions are properly connected with each other through a fine channel.

In the microchip according to this embodiment, the fluid circuit includes a centrifugation portion for separating a specimen introduced into the microchip into a target component and a nontarget component by centrifugation, as one of the aforementioned portions. The "specimen" denotes a substance (blood, for example) introduced into the fluid circuit as an object of test/analysis. The "target component" denotes a specific component in the specimen constituting a sample, prepared in the microchip, subjected to the test/analysis, and is typically a specific component in the specimen mixed or reacted with a liquid reagent having been previously held in the microchip. When the specimen is blood, a blood plasma component can be listed as the target component. The "nontarget component" denotes a component other than the "target component" in the specimen.

In this embodiment, the fluid circuit may include portions other than the centrifugation portion, and a liquid reagent holding portion for holding the liquid reagent, a target component measuring portion for measuring the target component, a liquid reagent measuring portion for measuring the liquid reagent, a mixing portion for mixing the target component and the liquid reagent with each other and a detecting portion for conducting the test/analysis (detection or determination of the specific component in the mixed liquid, for example) as to the obtained mixed liquid (the aforementioned sample subjected to the test/analysis) can be listed as such portions, for example. The microchip according to this embodiment may have all of these illustrated portions, or may not have at least any one portion. Further, the microchip may have portions other than these illustrated portions.

In this embodiment, the "liquid reagent" is a substance (reagent) to be mixed or reacted with the aforementioned target component, and previously stored in the liquid reagent holding portion of the fluid circuit before use of the microchip in general. The mixed liquid finally obtained by mixing the target component and the liquid reagent with each other is subjected to optical measurement such as a method of applying light to a portion (detecting portion, for example) in which the mixed liquid is stored and detecting the intensity (transmittance) of transmitted light, for example, so that the test/analysis is conducted, although not particularly restricted.

Fluid treatments in the fluid circuit such as extraction of the target component from the specimen (separation of the target component and the nontarget component), measurement of the target component and/or the liquid reagent, mixing of the target component and the liquid reagent and introduction of the obtained mixed liquid into the detecting portion can be performed by successively applying centrifugal force of proper directions to the microchip. Application of the centrifugal force to the microchip is typically performed by placing the microchip on an apparatus (centrifugal apparatus) capable of applying centrifugal force thereto. The microchip according to this embodiment is now described in more detail.

Figure 7:
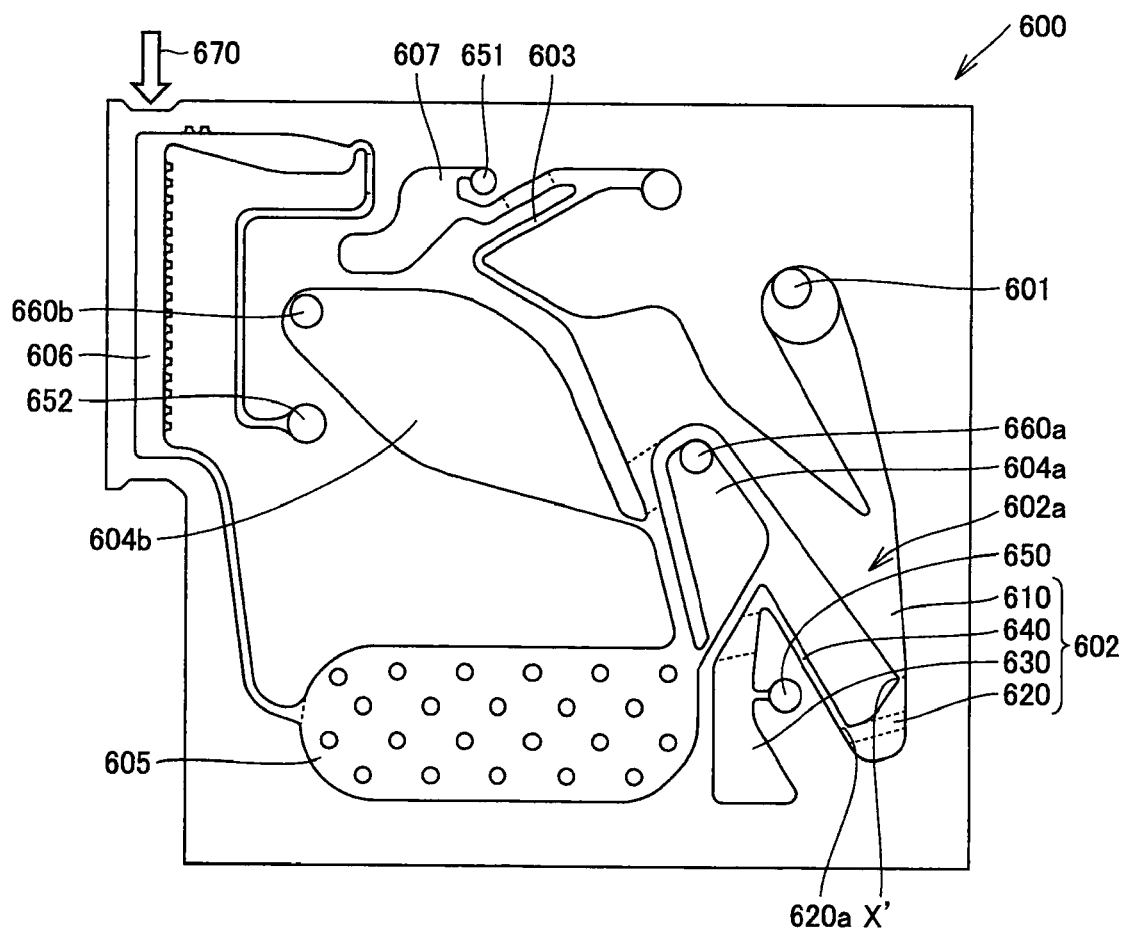
FIG. 7 is a schematic top plan view showing a preferred example of a microchip according to a second embodiment of the present invention.

FIG. 7 is a schematic top plan view showing a preferred example of the microchip according to this embodiment. A microchip 600 shown in FIG. 7 is prepared by bonding a second substrate to a groove forming-side surface of a first substrate including a groove constituting a fluid circuit and a through-hole penetrating in the thickness direction on the surface. FIG. 7 is a top plan view showing a first substrate-side surface of this microchip. While the groove constituting the fluid circuit is formed on a side opposite to the surface shown in FIG. 7 in practice, FIG. 7 shows the pattern of the groove with solid lines, so that the fluid circuit structure can be clearly grasped.

The fluid circuit formed in microchip 600 is mainly constituted of a centrifugation portion 602, connected to a specimen inlet 601 for introducing a specimen into the fluid circuit, for separating the specimen into a target component and a nontarget component, a target component measuring portion 603, connected to a first opening 602a of centrifugation portion 602, for measuring the target component, a second waste liquid reservoir 607 for storing the target component overflowing target component measuring portion 603 in measurement, liquid reagent holding portions 604a and 604b holding a liquid reagent A (not shown) and a liquid reagent B (not shown) respectively, a mixing portion 605 for mixing the measured target component and liquid reagents A and B with each other, and a detecting portion 606 for conducting test/analysis as to the mixed liquid obtained in mixing portion 605. Centrifugation portion 602 is constituted of a first storage portion 610, including first opening 602a for introducing the specimen on an upper portion (closer to specimen inlet 601), for storing the target component separated by centrifugation, a second storage portion 620, connected to the bottom portion of first storage portion 610, for mainly storing the nontarget component separated by centrifugation, a first waste liquid reservoir 630 and a first channel 640 connecting second storage portion 620 and first waste liquid reservoir 630 with each other.

Second storage portion 620 is coupled with the bottom portion of first storage portion 610 on a region opposite to first waste liquid reservoir 630 in the upper portion (closer to specimen inlet 601) thereof and has a second opening 620a on a region closer to first waste liquid reservoir 630 in the upper portion (closer to specimen inlet 601) thereof, while second opening 620a is coupled to an end of first channel 640.

A first air hole 650 is connected to first waste liquid reservoir 630, to provide a structure releasing gas (air) when a liquid (a specimen or a separated liquid stored in the second storage portion) flows into first waste liquid reservoir 630 so that inflow of the fluid is smoothly performed. Similarly, a second air hole 651 and a third air hole 652 are provided also on second waste liquid reservoir 607 and detecting portion 606 respectively. These air holes are through-holes passing through the first substrate in the thickness direction. Specimen inlet 601 and liquid reagent injection ports 660a and 660b provided on the respective liquid reagent holding portions are also through-holes passing through the first substrate in the thickness direction.

According to the structure such as that of centrifugation portion 602, the nontarget component (blood cell component, for example. However, the liquid stored in second storage portion 620 can contain a partial target component along with the nontarget component) separated by centrifugation and stored in second storage portion 620 can be prevented from flowing out in the direction of first storage portion 610 due to subsequent application of centrifugal force such as centrifugal force for introducing the separated target component into target component measuring portion 603. In other words, when centrifugal force (leftward centrifugal force in FIG. 7) for introducing the target component separated by centrifugation and stored in first storage portion 610 into target component measuring portion 603 is applied, it follows that the separated liquid containing the nontarget component stored in second storage portion 620 is introduced into first waste liquid reservoir 630 through first channel 640, not moved in the direction of first storage portion 610, whereby this separated liquid containing the nontarget component can be prevented from flowing out in the direction of target component measuring portion 603.

Further, second opening 620a is so included independently of first opening 602a for introducing the specimen that gas (air) in centrifugation portion 602 can be released to the direction of first waste liquid reservoir 630 when introducing the specimen into centrifugation portion 602, whereby the gas (air) can be prevented from remaining in centrifugation portion 602. Thus, the target component can be reliably extracted in a quantity sufficient for filling up target component measuring portion 603.

Preferably, first channel 640 connecting second storage portion 620 and first waste liquid reservoir 630 with each other extends from second opening 620a of second storage portion 620 in the upward direction in FIG. 7 (i.e., first storage portion 610 and first channel 640 are arranged on the same side with respect to second storage portion 620), and first storage portion 610, second storage portion 620 and first channel 640 constitute a substantially U-shaped form. Such a form is so constituted that the gas can be prevented from remaining in second storage portion 620 when introducing the specimen into centrifugation portion 602.

Preferably, target component measuring portion 603 and first waste liquid reservoir 630 are arranged on the same side with respect to first storage portion 610 and second storage portion 620. In the example shown in FIG. 7, both of target component measuring portion 603 and first waste liquid reservoir 630 are arranged on the left side in FIG. 7 with respect to first storage portion 610 and second storage portion 620. According to this structure, the target component can be introduced into target component measuring portion 603 and the separated liquid containing the nontarget component in second storage portion 620 can be introduced into first waste liquid reservoir 630 by applying centrifugal force (leftward centrifugal force in FIG. 7) for introducing the centrifuged target component in first storage portion 610 into target component measuring portion 603. At this time, first channel 640 preferably extends from second opening 620a not immediately upward in FIG. 7 but in a somewhat leftwardly inclined manner in FIG. 7, so that the separated liquid containing the nontarget component can be introduced into first waste liquid reservoir 630 due to the application of the leftward centrifugal force in FIG. 7.

While the width of a portion coupling first storage portion 610 and second storage portion 620 with each other is not particularly restricted, the width of this coupling portion is preferably narrow in order to disrupt the liquid in centrifugation portion 602 with excellent drainage on a boundary line X' shown in FIG. 7 or in the vicinity thereof when applying the leftward centrifugal force in FIG. 7. Therefore, the width of this coupling portion is preferably set to about 50 to 500 µm, for example. First storage portion 610 and second storage portion 620 may be connected with each other through a channel.

On the other hand, first opening 602a on the upper portion of first storage portion 610 is an inlet for introducing the specimen into centrifugation portion 620 as well as an outlet for introducing the target component separated by centrifugation into target component measuring portion 603, and hence the width thereof is preferably relatively large, and can be set to about 500 to 5000 µm, for example. Therefore, the form of first storage portion 610 typically takes a form such as that of an inverted triangle.

While the form of second storage portion 620 is not particularly restricted, the groove bottom surface constituting second storage portion 620 is preferably inclined (region held between two dotted lines in FIG. 7) to further increase the depth of the groove on a region closer to the bottom portion than this inclined region. Thus, the separated liquid of a large quantity can be stored with a small area. While the position of second opening 620a is not particularly restricted either, second opening 620a is preferably provided on the upper portion (closer to specimen inlet 601) thereof. When first waste liquid reservoir 630 is arranged on the left side with respect to second storage portion 620, second opening 620a is preferably provided on the left end of the upper portion of second storage portion 620, as shown in FIG. 7, for example. This is so intended that the separated liquid stored in second storage portion 620 can be efficiently fed to first waste liquid reservoir 630.

Figure 8:
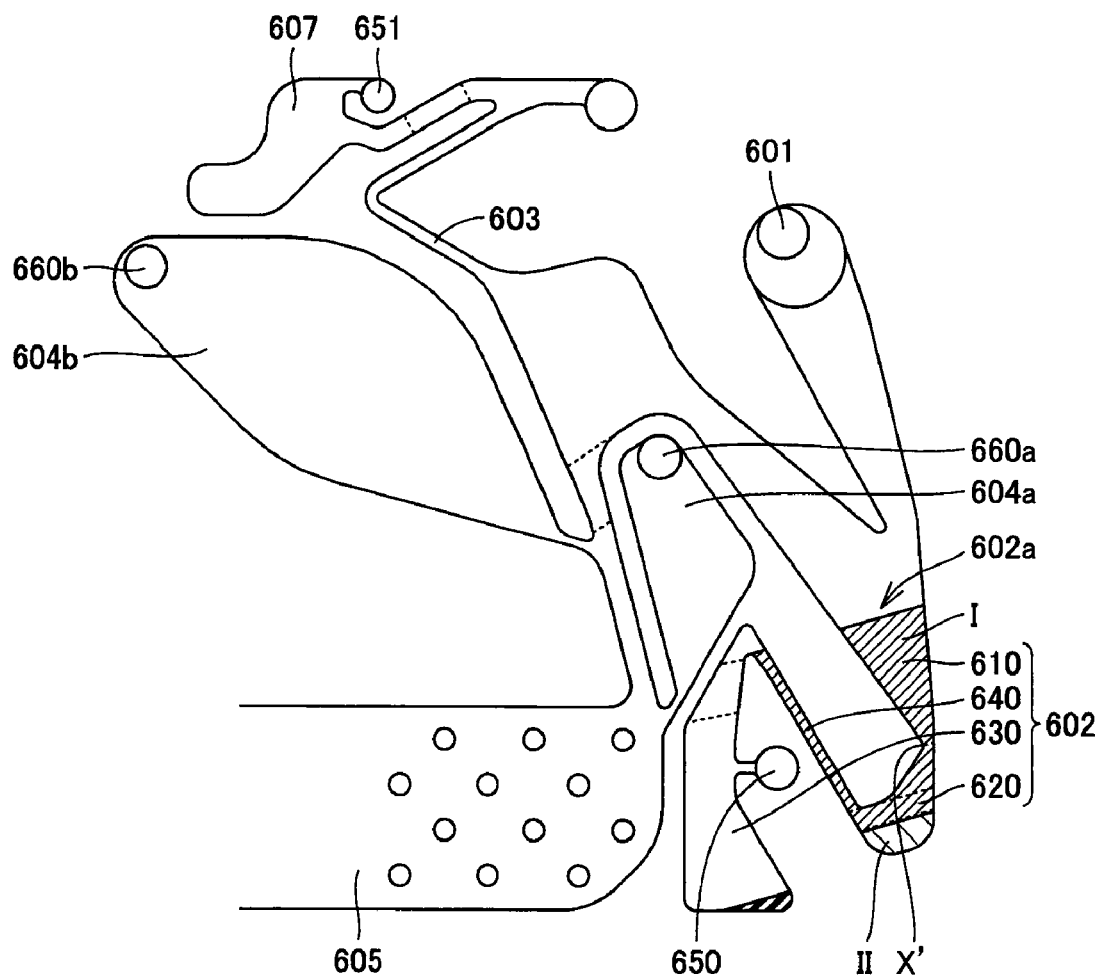
FIG. 8 is a top plan view showing the periphery of a centrifugation portion of the microchip shown in FIG. 7.

The separation treatment in centrifugation portion 602 of microchip 600 shown in FIG. 7 is now described with reference to FIG. 8. FIG. 8 is a top plan view showing a portion around centrifugation portion 602 of microchip 600 shown in FIG. 7, for illustrating a state after introducing the specimen (blood or the like) from specimen inlet 601 and thereafter introducing the specimen into centrifugation portion 602 and performing centrifugation by applying downward centrifugal portion in FIG. 8.

As shown in FIG. 8, the specimen introduced into centrifugation portion 602 is separated into a target component I (blood plasma component, for example) and a nontarget component II (blood cell component, for example) by the centrifugation through the application of the downward centrifugal force. While the interfacial position between target component I and nontarget component II is changeable in response to the quantity of the nontarget component in the specimen, the volume of second storage portion 620 is so adjusted that at least this interface is positioned in second storage portion 620. When the specimen is human blood and nontarget component II is a blood cell component, for example, the hematocrit of the human blood is generally about 35 to 50% and hence the volume of second storage portion 620 is adjusted in consideration of this point.

When introducing the specimen into centrifugation portion 602 through first opening 602a, gas (air) having been present in centrifugation portion 602 moves in the direction of first waste liquid reservoir 630 through first channel 640, whereby the gas (air) does not remain in centrifugation portion 602. The gas moving to first waste liquid reservoir 630 is discharged from the microchip through first air hole 650. When a specimen in a quantity exceeding the total volume of first storage portion 610, second storage portion 620 and first channel 640 is introduced into centrifugation portion 602, the excess specimen is stored in first waste liquid reservoir 630 through first channel 640 (see FIG. 8).

Liquid reagents A and B having been stored in liquid reagent holding portions 604a and 604b are introduced into mixing portion 605 respectively, due to the application of the downward centrifugal force.

Then, leftward centrifugal force in FIG. 8 is applied to the microchip from the centrifuged state shown in FIG. 8, thereby introducing target component I in first storage portion 610 into target component measuring portion 603 and performing measurement. Target component I overflowing target component measuring portion 603 is stored in second waste liquid reservoir 607 connected to target component measuring portion 603. Target component I introduced into target component measuring portion 603 due to this application of the leftward centrifugal force is a target component upward beyond boundary line X shown in FIG. 8 or in the vicinity thereof (closer to first storage portion 610). On the other hand, target component I downward beyond boundary line X' or in the vicinity thereof (closer to second storage portion 620. Also including target component I in first channel 640) and nontarget component II are introduced into first waste liquid reservoir 630 due to this application of the leftward centrifugal force. Thus, it follows that target component I downward beyond boundary line X' or in the vicinity thereof and nontarget component II move to first waste liquid reservoir 630 through first channel 640, thereby not flowing out in the direction of target component measuring portion 603.

A fluid treatment (operating method of the microchip) after measuring the target component is generally as follows, with reference to FIG. 7: First, the target component in target component measuring portion 603 is introduced into mixing portion 605 by applying downward centrifugal force in FIG. 7, and mixed with liquid reagents A and B to obtain a mixed liquid. Then, the mixed liquid is introduced into detecting portion 606 by applying leftward centrifugal force in FIG. 7. The mixed liquid in detecting portion 606 is subjected to optical measurement such as a method of applying light 670 to detecting portion 606 and measuring the intensity (transmittance) of transmitted light, so that test/analysis is conducted.

Third Embodiment

Characteristic portions of this embodiment are now described in detail. As to the remaining points, the contents described as to the aforementioned second embodiment also apply to this embodiment.

In a microchip according to this embodiment, a fluid circuit includes a centrifugation portion for separating a specimen introduced into the microchip into a target component and a nontarget component by centrifugation. When the specimen is blood, a blood plasma component can be listed as the target component, and a blood cell component can be listed as the nontarget component.

The microchip according to this embodiment has a specimen inlet, and the specimen is introduced into the fluid circuit through this specimen inlet. The specimen inlet can be constituted as a through-port penetrating from one surface of the microchip up to the fluid circuit. More specifically, when the microchip is constituted of a first substrate including a groove on the aforementioned substrate surface and a second substrate, the specimen inlet can be formed by a through-port passing through the first substrate in the thickness direction. When the microchip is formed by bonding a third substrate, a first substrate including grooves provided on both surfaces of the substrate and a second substrate with each other in this order, the specimen inlet can be formed by a through-port passing through the third substrate (or the second substrate) in the thickness direction. The aforementioned centrifugation portion is connected with the specimen inlet through a channel, so that the specimen injected from the specimen inlet can be introduced into the centrifugation portion.

Figure 9:
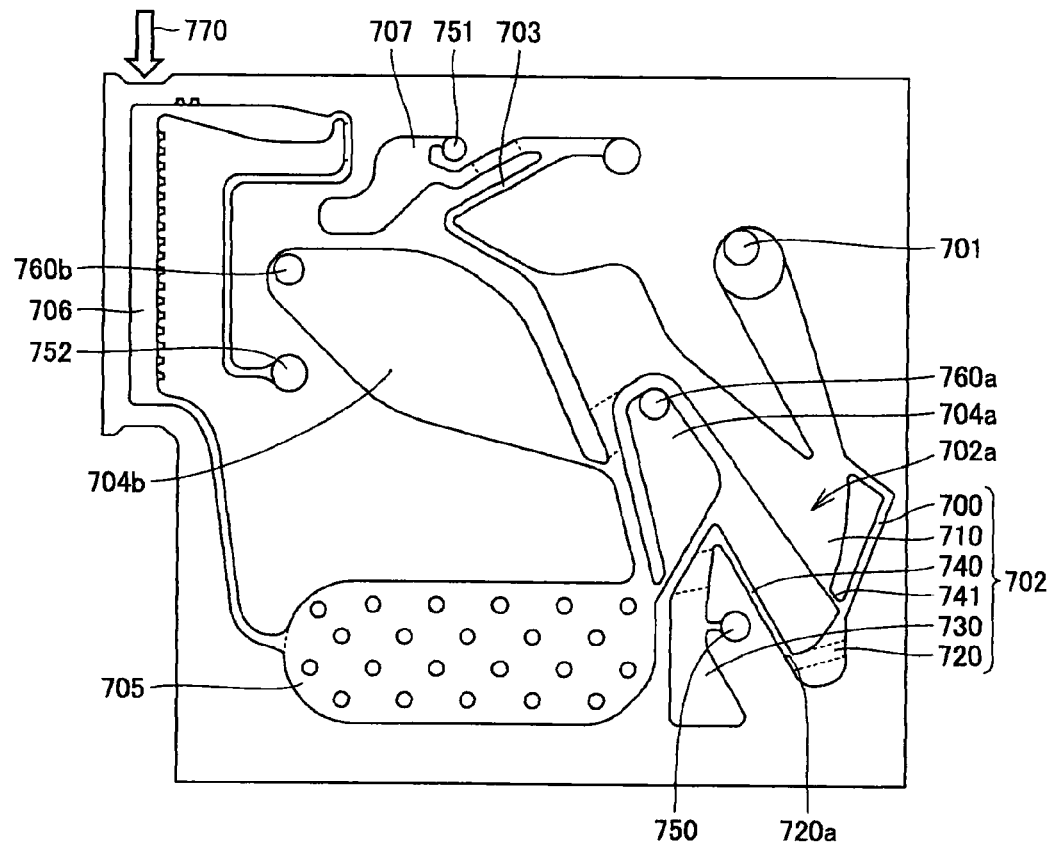
FIG. 9 is a schematic top plan view showing a preferred example of a microchip according to a third embodiment of the present invention.

FIG. 9 is a schematic top plan view showing a preferred example of the microchip according to this embodiment. The microchip shown in FIG. 9 is prepared by bonding a second substrate to a groove forming-side surface of a first substrate including a groove constituting a fluid circuit and a through-hole penetrating in the thickness direction on the surface. FIG. 9 is a top plan view showing a first substrate-side surface of this microchip. While the groove constituting the fluid circuit is formed on a surface (surface bonded to the second substrate) of the first substrate opposite to the surface shown in FIG. 9 in practice, FIG. 9 shows the pattern of the groove with solid lines, so that the fluid circuit structure can be clearly grasped.

The fluid circuit formed in the microchip is mainly constituted of a centrifugation portion 702, connected to a specimen inlet 701 for introducing a specimen into the fluid circuit, for separating the specimen into a target component and a nontarget component, a target component measuring portion 703, connected to a first opening 702a of centrifugation portion 702, for measuring the target component, a second waste liquid reservoir 707 for storing the target component overflowing target component measuring portion 703 in measurement, liquid reagent holding portions 704a and 70b holding a liquid reagent A (not shown) and a liquid reagent B (not shown) respectively, a mixing portion 705 for mixing the measured target component and liquid reagents A and B with each other, and a detecting portion 706 for conducting test/analysis as to the mixed liquid obtained in mixing portion 705. Specimen inlet 701 is a through-port passing through the first substrate in the thickness direction.

Centrifugation portion 702 is constituted of a first storage portion 710, including a first opening 702a for introducing the specimen on an upper portion (closer to specimen inlet 701), for storing the target component separated by centrifugation due to application of downward centrifugal force (or centrifugal force in a direction at least including a downward component) in FIG. 9, a first channel 741 whose one end is connected to the bottom portion (opposite to first opening 702a) of first storage portion 710, a second storage portion 720, connected to another end of first channel 741, for mainly storing the nontarget component separated by the aforementioned centrifugation, a gas introduction channel 700 whose one end is connected to the position connecting first channel 741 and second storage portion 720 with each other and whose another end is connected to a channel connecting specimen inlet 701 and centrifugation portion 702 with each other, a first waste liquid reservoir 730, and a second channel 740 connecting second storage portion 720 and first waste liquid reservoir 730 with each other.

Second storage portion 720 is coupled with the bottom portion of first storage portion 710 through first channel 741 on a region of the upper portion (closer to specimen inlet 701) thereof opposite to first waste liquid reservoir 730 and has a second opening 720a on a region of the upper portion (closer to specimen inlet 701) thereof on the side of first waste liquid reservoir 730, while an end of first channel 740 is coupled to second opening 720a.

An end of gas introduction channel 700 is connected to the position connecting first channel 741 and second storage portion 720 with each other, and another end thereof is connected to the channel connecting specimen inlet 701 and centrifugation portion 702 with each other. Thus, gas (air) can be introduced into this connectional position through specimen inlet 701.

A first air hole 750 is connected to first waste liquid reservoir 730, to provide a structure releasing the gas (air) when a liquid (the specimen and a separated liquid stored in the second storage portion) flows into first waste liquid reservoir 730 so that inflow of the liquid is smoothly performed. Similarly, a second air hole 751 and a third air hole 752 are provided also on second waste liquid reservoir 707 and detecting portion 706 respectively. These air holes are through-holes passing through the first substrate in the thickness direction. Liquid reagent injection ports 760a and 760b provided on liquid reagent holding portions 704a and 704b are also through-holes passing through the first substrate in the thickness direction, and liquid reagents A and B are injected through liquid reagent injection ports 760a and 760b respectively, so that the liquid reagents are previously stored.

According to the structure such as that of aforementioned centrifugation portion 702, the nontarget component (blood cell component, for example. However, the liquid stored in second storage portion 720 can contain a partial target component along with the nontarget component) separated by centrifugation and stored in second storage portion 720 can be prevented from flowing out in the direction of first storage portion 710 due to subsequent application of centrifugal force such as centrifugal force for introducing the separated target component in first storage portion 710 into target component measuring portion 703. In other words, when centrifugal force (leftward centrifugal force in FIG. 9) for introducing the target component separated by centrifugation and stored in first storage portion 710 into target component measuring portion 703 is applied, it follows that the separated liquid containing the nontarget component stored in second storage portion 720 is introduced into first waste liquid reservoir 730 through second channel 740, not moved in the direction of first storage portion 710, whereby this separated liquid containing the nontarget component can be prevented from flowing out in the direction of target component measuring portion 703 (i.e., the direction of first storage portion 710).

Further, second opening 720a is so included independently of first opening 702a for introducing the specimen that gas (air) in centrifugation portion 702 can be released to the direction of first waste liquid reservoir 730 when introducing the specimen into centrifugation portion 702, whereby the gas (air) can be prevented from remaining in centrifugation portion 702. Thus, the target component can be reliably extracted in a quantity sufficient for filling up target component measuring portion 703.

In addition, gas introduction channel 700 is so connected to the connectional position between first channel 741 and second storage portion 720 that gas (air) can be introduced into this connectional position, whereby the target component in first storage portion 710 can be prevented from being pulled by the liquid in second storage portion 720 by surface tension and flowing out toward second storage portion 720 when introducing the target component into target component measuring portion 703 by applying the leftward centrifugal force in FIG. 9. Thus, the target component can be reliably introduced into target component measuring portion 703 in a quantity sufficient for filling up target component measuring portion 703.

Preferably, second channel 740 connecting second storage portion 720 and first waste liquid reservoir 730 with each other extends from second opening 720a of second storage portion 720 in the upward direction in FIG. 9 (i.e., first storage portion 710 and second channel 740 are arranged on the same side with respect to second storage portion 720), and first storage portion 710, second storage portion 720 and second channel 740 constitute a substantially U-shaped form. Such a form is so constituted that the gas can be prevented from remaining in second storage portion 720 when introducing the specimen into centrifugation portion 702.

Preferably, target component measuring portion 703 and first waste liquid reservoir 730 are arranged on the same side with respect to first storage portion 710 and second storage portion 720. In the example shown in FIG. 9, both of target component measuring portion 703 and first waste liquid reservoir 730 are arranged on the left side in FIG. 9 with respect to first storage portion 710 and second storage portion 720.

According to this structure, the target component can be introduced into target component measuring portion 703 and the separated liquid containing the nontarget component in second storage portion 720 can be introduced into first waste liquid reservoir 730 by applying centrifugal force (leftward centrifugal force in FIG. 9) for introducing the centrifuged target component in first storage portion 710 into target component measuring portion 703. At this time, second channel 740 preferably extends from second opening 720a not immediately upward in FIG. 9 but in a somewhat leftwardly inclined manner in FIG. 9, so that the separated liquid containing the nontarget component can be introduced into first waste liquid reservoir 730 due to the application of the leftward centrifugal force in FIG. 9.

When target component measuring portion 703 and first waste liquid reservoir 730 are arranged on the same side with respect to first storage portion 710 and second storage portion 720 as hereinabove described, gas introduction channel 700 is preferably arranged on a side opposite to the side where target component measuring portion 703 and first waste liquid reservoir 730 are arranged with respect to first storage portion 710 and second storage portion 720. In the example shown in FIG. 9, gas introduction channel 700 is arranged on the right side in FIG. 9 with respect to first storage portion 710 and second storage portion 720. According to this structure, the separated separated liquid in second storage portion 720 can be prevented from flowing back into gas introduction channel 700 when applying centrifugal force (leftward centrifugal force in FIG. 9) for introducing the centrifuged target component in first storage portion 710 into target component measuring portion 703.

Figure 10:
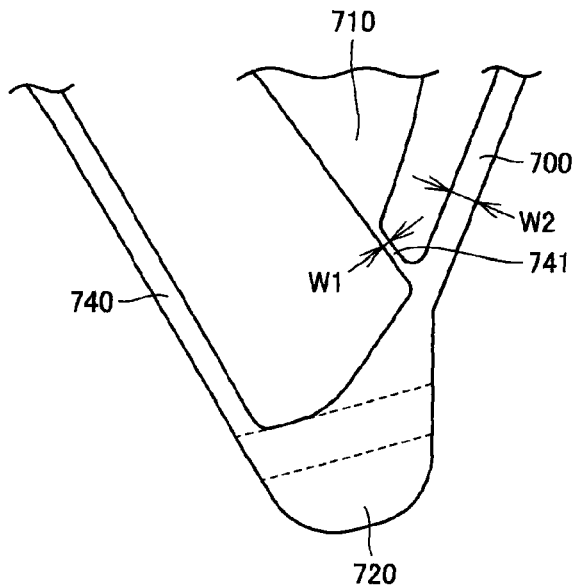
FIG. 10 is a top plan view showing a centrifugation portion of the microchip shown in FIG. 9 in a partially enlarged manner.

FIG. 10 is a top plan view showing centrifugation portion 702 of the microchip shown in FIG. 9 in a partially enlarged manner. The bottom portion of first storage portion 710 and the upper right end of second storage portion 720 are connected with each other by first channel 741, and the end of gas introduction channel 700 is connected to the position connecting first channel 741 and second storage portion 720 with each other. If the width W1 of first channel 741 is rendered smaller than the width W2 of gas introduction channel 700 as shown in FIG. 10, the target component charged into gas introduction channel 700 preferentially moves to second storage portion 720 when leftward centrifugal force in FIG. 10 is applied in order to introduce the target component stored in first storage portion 710 into target component measuring portion 703, and it follows that the gas (air) so interposes on the connectional position between first channel 741 and second storage portion 720 that the target component in first storage portion 710 and the separated liquid in second storage portion 720 are parted when the target component charged into gas introduction channel 700 is used up, whereby the target component in first storage portion 710 is more effectively prevented from flowing out in the direction of second storage portion 720.

In order to attain this effect, the depth of first channel 741 may be rendered smaller than the depth of gas introduction channel 700. In this case, width W1 of first channel 741 and width W2 of gas introduction channel 700 may have the aforementioned relation, or may be substantially identical widths.

On the other hand, first opening 702a on the upper portion of first storage portion 710 is an inlet for introducing the specimen into centrifugation portion 702 as well as an outlet for introducing the target component separated by centrifugation into target component measuring portion 703, and hence the width thereof is preferably relatively large, and can be set to about 500 to 5000 μm, for example. Therefore, the form of first storage portion 710 typically takes a form such as that of an inverted triangle.

While the form of second storage portion 720 is not particularly restricted, the groove bottom surface constituting second storage portion 720 (hence the depth of the fluid circuit) is preferably inclined (region held between two dotted lines in each of FIGS. 9 and 10) to further increase the depth of the groove on a region closer to the bottom portion than this inclined region. Thus, the separated liquid of a large quantity can be stored with a small area. While the position of second opening 720a is not particularly restricted either, second opening 720a is preferably provided on the upper portion (closer to specimen inlet 701) thereof. When first waste liquid reservoir 730 is arranged on the left side with respect to second storage portion 720, second opening 720a is preferably provided on the left end of the upper portion of second storage portion 720, as shown in FIG. 9, for example. This is so intended that the separated liquid stored in second storage portion 720 can be efficiently fed to first waste liquid reservoir 730.

While another end of gas introduction channel 700 is connected to specimen inlet 701 through the channel connecting specimen inlet 701 and centrifugation portion 702 with each other in order to introduce the gas into the connectional position between first channel 741 and second storage portion 720 in the microchip shown in FIG. 9, the present invention is not restricted to this but this end may be connected to a separately provided through-port.

Figure 11:
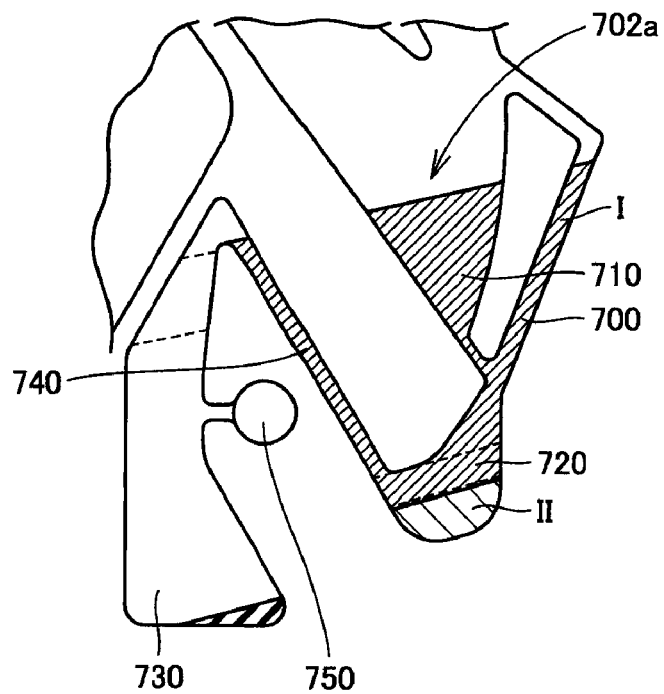
FIGS. 11 and 12 are top plan views for illustrating a separation treatment in the centrifugation portion of the microchip shown in FIG. 9.
Figure 12:
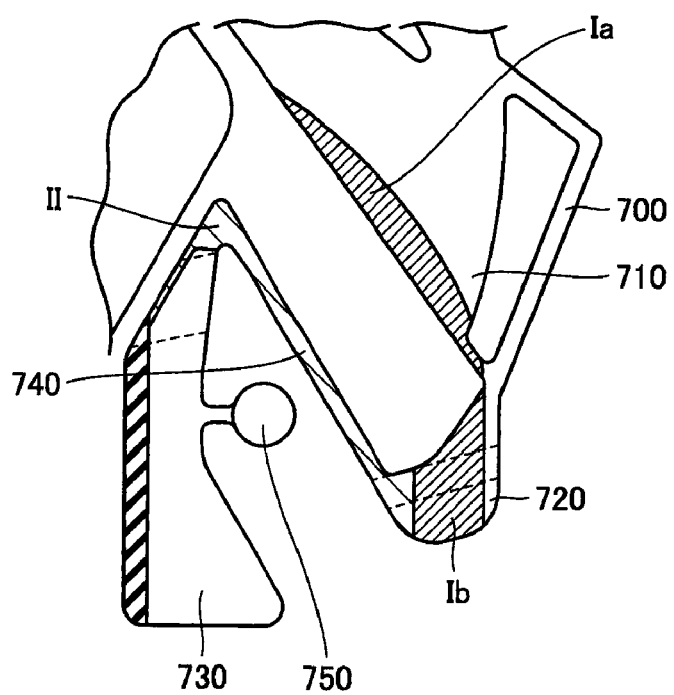

A separation treatment in centrifugation portion 702 of the microchip shown in FIG. 9 is now described with reference to FIGS. 11 and 12. FIGS. 11 and 12 are top plan views for illustrating the separation treatment in centrifugation portion 702 of the microchip shown in FIG. 9. In a fluid treatment with the microchip shown in FIG. 9, the specimen (blood or the like) is first introduced into the fluid circuit from specimen inlet 701 (not shown in FIG. 11) as shown in FIG. 11, and the specimen is introduced into centrifugation portion 702 from first opening 702a by applying downward centrifugal force in FIG. 11 to the microchip and centrifuged into a target component I (blood plasma component, for example) and a nontarget component II (blood cell component, for example) by further applying this downward centrifugal force. While the interfacial position between target component I and nontarget component II is changeable in response to the quantity of the nontarget component in the specimen, the volume of second storage portion 720 is so adjusted that at least this interface is positioned in second storage portion 720. When the specimen is human blood and nontarget component II is a blood cell component, for example, the hematocrit of the human blood is generally about 35 to 50% and hence the volume of second storage portion 720 is adjusted in consideration of this point. According to this centrifugation, first storage portion 710, first channel 741, part of gas introduction channel 700 and second channel 740 are filled up with target component I, and second storage portion 720 is filled up with part of phase-separated target component I and nontarget component II.

When introducing the specimen into centrifugation portion 702 through first opening 702a, gas (air) having been present in centrifugation portion 702 moves in the direction of first waste liquid reservoir 730 through second channel 740 or gas introduction channel 700 or discharged from specimen inlet 701, whereby the gas (air) does not remain in centrifugation portion 702. The gas moving to first waste liquid reservoir 730 is discharged from the microchip through first air hole 750. When a specimen of a quantity overflowing second channel 740 is introduced into centrifugation portion 702, the excess specimen is stored in first waste liquid reservoir 730 through second channel 740 (see FIG. 11).

Liquid reagents A and B having been stored in liquid reagent holding portions 704a and 704b are introduced into mixing portion 705 due to this application of the downward centrifugal force (see FIG. 9).

Then, leftward centrifugal force is applied to the microchip from the centrifuged state shown in FIG. 11, thereby introducing target component I in first storage portion 710 into target component measuring portion 703 and performing measurement. Target component I overflowing target component measuring portion 703 is stored in second waste liquid reservoir 707 connected to target component measuring portion 703 (see FIG. 9). It follows that target component I in second storage portion 720 and nontarget component II are introduced into first waste liquid reservoir 730 through second channel 740, due to this application of the leftward centrifugal force. FIG. 12 is a diagram showing a state where target component I (Ia shown in FIG. 12) in first storage portion 710 moves in the direction of target component measuring portion 703 and the separated liquid (nontarget component I and target component Ib) in second storage portion 720 move to first waste liquid reservoir 730 due to this leftward centrifugal force. As shown in FIG. 12, target component I in first storage portion 710 and the separated liquid in second storage portion 720 are typically parted in the vicinity of the lower portion (position connected with second storage portion 720) of first channel 741 by this leftward centrifugal force, to move in the aforementioned respective directions. When gas introduction channel 700 of the aforementioned structure is provided at this time, the separated liquid in second storage portion 720 moves to first waste liquid reservoir 730 while target component I in gas introduction channel 700 preferentially moves to second storage portion 720, and it follows that the gas interposes on the connectional position between first channel 741 and second storage portion 720 (state shown in FIG. 12).

Thus, the gas is so interposed on the connectional position between first channel 741 and second storage portion 720 that it follows that target component I upward (closer to first storage portion 710) beyond this connectional position and the separated liquid downward (closer to second storage portion 720) beyond this connectional position are parted by the interposed gas, whereby, when the separated liquid in second storage portion 720 moves to first waste liquid reservoir 730, target component I in first storage portion 710 can be prevented from being pulled by this, moving in the direction of second storage portion 720 and flowing out toward first waste liquid reservoir 730. Thus, target component I in first storage portion 710 can be introduced into target component measuring portion 730 by the total quantity or substantially by the total quantity. The separated liquid in second storage portion 720 can also be prevented from flowing out in the direction of target component measuring portion 703 through first channel 741.

The fluid treatment (operating method of the microchip) after measuring the target component is generally as follows, with reference to FIG. 9: First, the target component in target component measuring portion 703 is introduced into mixing portion 705 by applying downward centrifugal force in FIG. 9 and mixed with liquid reagents A and B to obtain a mixed liquid. Then, the mixed liquid is introduced into detecting portion 706 by applying leftward centrifugal force in FIG. 9. The mixed liquid in detecting portion 706 is subjected to optical measurement such as a method of applying light 770 to detecting portion 706 and detecting the intensity (transmittance) of transmitted light, so that test/analysis is conducted.

Fourth Embodiment

Characteristic portions of this embodiment are now described in detail. As to the remaining points, the contents described as to the aforementioned second embodiment also apply to this embodiment.

In a microchip according to this embodiment, a fluid circuit includes a centrifugation portion for separating a specimen introduced into the microchip into a first target component and a second target component by centrifugation. When the specimen is blood, a blood plasma component can be listed as the first target component, and a blood cell component can be listed as the second target component.

The microchip according to this embodiment has a specimen inlet, and the specimen is introduced into the fluid circuit through this specimen inlet. The specimen inlet can be constituted as a through-port penetrating from one surface of the microchip up to the fluid circuit. More specifically, when the microchip is constituted of a first substrate including a groove on the aforementioned substrate surface and a second substrate, the specimen inlet can be formed by a through-port passing through the first substrate in the thickness direction. When the microchip is formed by bonding a third substrate, a first substrate including grooves provided on both surfaces of the substrate and a second substrate with each other in this order, the specimen inlet can be formed by a through-port passing through the third substrate (or the second substrate) in the thickness direction. The aforementioned centrifugation portion is connected with the specimen inlet through a channel, so that the specimen injected from the specimen inlet can be introduced into the centrifugation portion.

Figure 13:
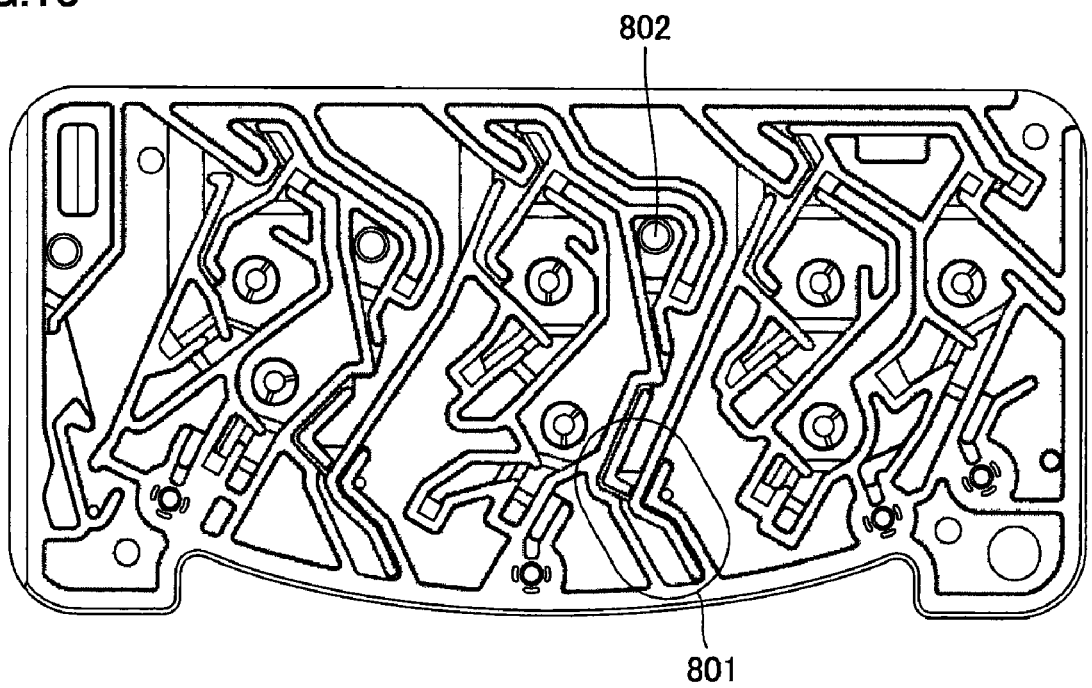
FIG. 13 is a schematic top plan view showing a preferred example of a microchip according to a fourth embodiment of the present invention.
Figure 14:
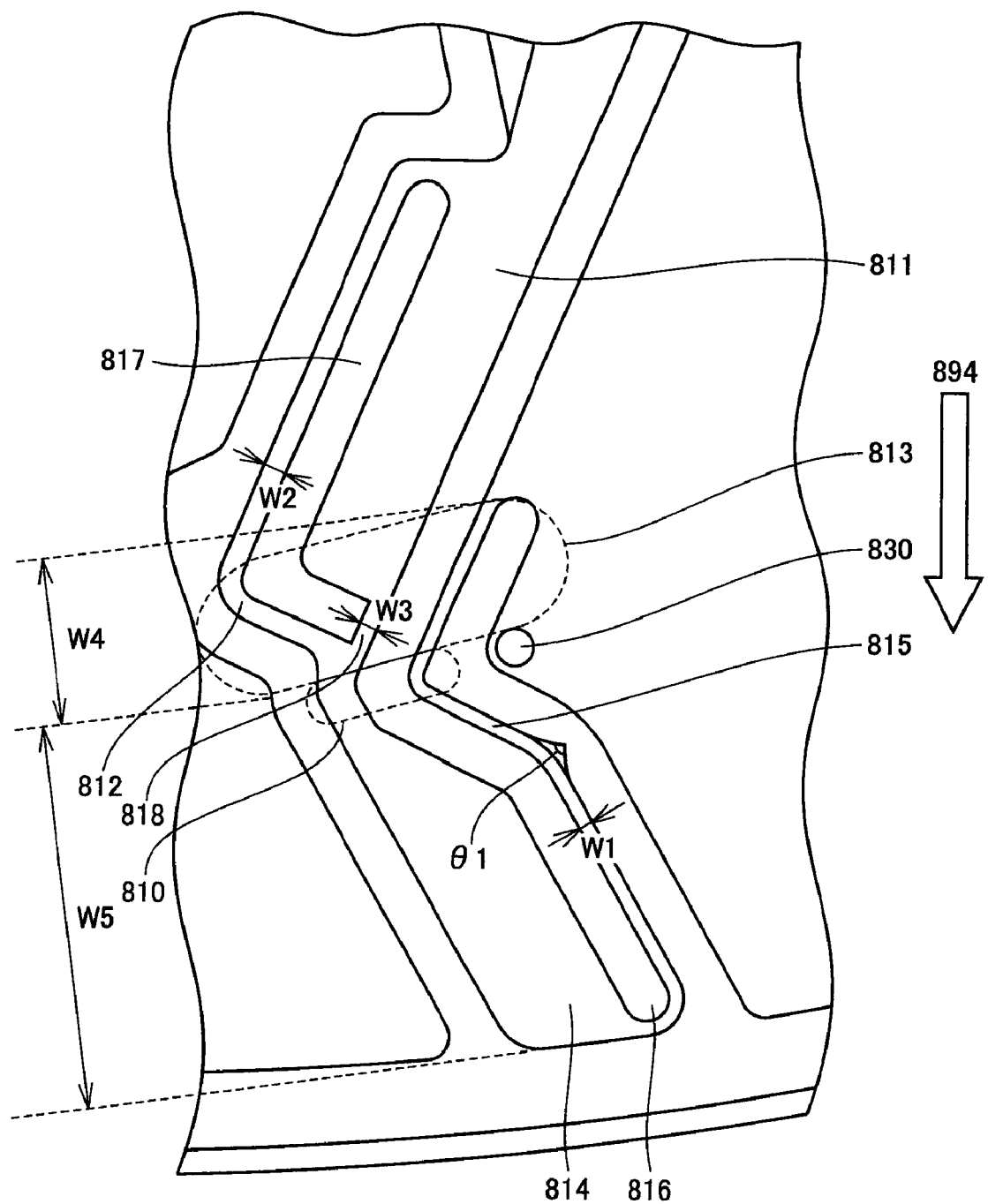
FIG. 14 is a schematic top plan view partially enlarging the microchip shown in FIG. 13.

FIG. 13 is a schematic top plan view showing a preferred example of the microchip according to this embodiment. FIG. 14 is a schematic top plan view partially enlarging FIG. 13.

The microchip according to this embodiment is prepared by bonding a second substrate to a groove forming-side surface of a first substrate including a groove constituting a fluid circuit and a through-hole penetrating in the thickness direction on the surface. FIG. 13 is a top plan view showing a first substrate-side surface of this microchip. While the groove constituting the fluid circuit is formed on a surface (surface bonded to the second substrate) of the first substrate opposite to the surface shown in FIG. 13 in practice, FIG. 13 shows the pattern of the groove with solid lines, so that the fluid circuit structure can be clearly grasped.

The microchip according to this embodiment has a specimen inlet 802, penetrating from one surface thereof up to the fluid circuit, for introducing the specimen into the fluid circuit. The fluid circuit includes a centrifugation portion 801 for separating the specimen into a first target component and a second target component by centrifugation. FIG. 14 is a top plan view enlarging centrifugation portion 801 shown in FIG. 13. As shown in FIG. 14, centrifugation portion 801 includes a storage portion 814, provided on the side of specimen inlet 802, constituted of a U-shaped wall surface having a narrowed opening 810 and a measuring portion 813, provided in a direction of opening 810 closer to specimen inlet 802, connected with storage portion 814 through opening 810. In the microchip according to this embodiment, U-shaped storage portion 814 may be substantially U-shaped, may have a constant length in the short-side direction of the microchip shown in FIG. 13, and may be in such a form that the wall surface forming storage portion 814 is narrowed toward the direction of opening 810. Storage portion 814 is a portion for storing the specimen when centrifugal force is applied along arrow 894. Measuring portion 813 is connected with storage portion 814 through opening 810. A wall surface forming measuring portion 813 preferably spreads from opening 810 toward the direction closer to specimen inlet 802. The wall surface forming measuring portion 813 and the wall surface forming storage portion 814 are preferably a series of wall surfaces.

Centrifugation portion 801 includes a first wall surface 816 arranged up to a portion inward beyond opening 810 in storage portion 814 along the inner walls forming measuring portion 813 and storage portion 814. A first channel 815 formed by the inner wall forming storage portion 814 and first wall surface 816 is formed, and an end portion of first wall surface 816 in storage portion 814 does not come into contact with the inner wall of storage portion 814.

Centrifugation portion 801 further includes a second wall surface 817 arranged up to opening 810 along the inner wall forming measuring portion 813 on another end where first wall surface 816 is arranged. A second channel 812 is formed by the inner wall forming measuring portion 813 and second wall surface 817, and second channel 812 and storage portion 814 are connected with each other. Preferably, second wall surface 817 is formed in a substantially L-shaped manner, and substantially parallel to first wall surface 816 directed toward specimen inlet 802 from opening 810, as shown in FIG. 14.

The microchip according to this embodiment comprises a specimen introducing portion 811 formed by second wall surface 817 and first wall surface 816 and a third channel 818 formed between an end portion of second wall surface 817 and first wall surface 816 for connecting specimen inlet 802 and the inner part of storage portion 814 with each other.

First channel 815 is connected to an air hole 830 coupling an external portion of the microchip and the fluid circuit with each other. First channel 815 and air hole 830 are so connected with each other that no air accumulates in overall centrifugation portion 801, and deterioration of drainage in the channel hardly takes place. The specimen inlet is also connected with the external portion of the microchip.

In the microchip according to this embodiment, the width W3 of third channel 818 is preferably smaller than the width W2 of second channel 812. Width W3 of third channel 813 is preferably smaller than the width W1 of first channel 815. This is because the widths exert influence when separately collecting the specimen as the first target component and the second target component after applying centrifugal force in an operation of the fluid in centrifugation portion 801 described later. More specifically, W1, W2 and W3 can be set to not more than 0.2 μm, not more than 0.3 μm and not more than 0.15 μm respectively.

The volumes of measuring portion 813 and storage portion 814 are properly set in response to the specimen in the microchip according to this embodiment. More specifically, the width W4 of measuring portion 813 in the short-side direction in the microchip of FIG. 13 and the width W5 of storage portion 814 in the short-side direction are so adjusted that an interface where the first target component and the second target component are separated from each other is formed in narrowed opening 810. First channel 815 and second channel 812 are preferably formed upward beyond storage portion 814 in the positional relation in FIG. 14.

The inner wall of storage portion 814 along which first wall surface 816 is arranged is preferably bent in an L-shaped manner, and more specifically, θ1 is preferably 90 to 120 degrees in FIG. 14. This is because the first target component can be prevented from being pulled in the fluid circuit when only the target component is extracted from measuring portion 813 after application of centrifugal force, as described later.

The microchip shown in FIG. 13 further comprises a first calibration portion calibrating the first target component and a second calibration portion calibrating the second target component, first channel 815 and second channel 812 are connected to the first calibration portion, and specimen inlet 811 is connected to the second calibration portion. The microchip so comprises the first calibration portion and the second calibration portion that the same can simultaneously obtain both test results of the first target component and the second target component. The forms etc. of the first calibration portion and the second calibration portion can be properly set.

In this embodiment, only the first target component is extracted from specimen introducing portion 811 and first channel 815 and the second target component is extracted from second channel 812 after centrifugal force is applied along arrow 894.

The fluid circuit formed in the microchip according to this embodiment is mainly composed of centrifugation portion 801, connected to specimen inlet 802 for introducing the specimen into the fluid circuit, for separating the specimen into the first target component and the second target component, measuring portion 813, connected to specimen introducing portion 811 of centrifugation portion 801, for measuring the specimen, a waste liquid reservoir (whose position is not shown in FIG. 13) for storing the specimen overflowing measuring portion 813 in measurement, and a first detecting portion and a second detecting portion (whose positions are not shown in FIG. 13) for conducting test/analysis as to a liquid reagent A (not shown) as well as the first target component and the second target component. Specimen inlet 802 is a through-port passing through the first substrate in the thickness direction.

According to the structure such as that of aforementioned centrifugation portion 801, the second target component (blood cell component, for example. However, the liquid stored in storage portion 814 can contain a partial first target component along with the second target component) separated by centrifugation and stored in storage portion 814 can be prevented from flowing out in the direction of specimen introducing portion 811 due to subsequent application of centrifugal force such as centrifugal force for extracting the separated first target component (blood plasma, for example) from specimen introducing portion 811. In other words, when centrifugal force (rightward centrifugal force in FIG. 13) for extracting only the first target component separated by centrifugation and stored in measuring portion 813 from specimen introducing portion 811 is applied, it follows that the second target component stored in storage portion 814 is baffled not in the direction of specimen introducing portion 811 but in first channel 815, whereby this second target component can be prevented from flowing out in the direction of specimen introducing portion 811.

The microchip comprises second channel 812 independently of specimen introducing portion 811 for introducing the specimen so that gas (air) in centrifugation portion 801 can be released in the direction of first channel 815 when introducing the specimen into centrifugation portion 801, whereby the gas (air) can be prevented from remaining in centrifugation portion 801. Thus, the flows of the specimen, the first target component and the second target component smoothen, and drainage in each channel improves.

Further, second channel 812 is so connected to the connectional position between third channel 818 and storage portion 814 that the gas (air) can be introduced into this connectional position, whereby the first target component in measuring portion 813 can be prevented from flowing out in the direction of storage portion 814 when extracting the first target component from specimen introducing portion 811 by applying rightward centrifugal force in FIG. 13.

It is preferable that second channel 812 and first channel 815 extend upward in FIG. 13 from opening 810 of storage portion 814, and it is more preferable that second channel 812 and first channel 815 constitute a substantially V-shaped form. According to this form, such an effect can be attained that a solution in second channel 812 can be easily discharged in FIG. 15D while outflow of a solution in first channel 815 is limited.

According to the microchip of this embodiment, as hereinabove described, the separated second target component in storage portion 814 can be prevented from being simultaneously extracted from specimen introducing portion 811 when applying centrifugal force (rightward centrifugal force in FIG. 13) for extracting the centrifuged first target component in measuring portion 813 from specimen introducing portion 811.

While the form of storage portion 814 is not particularly restricted, the groove bottom surface constituting storage portion 814 (hence the depth of the fluid circuit) is preferably so inclined as to further increase the depth of the groove in a region closer to the bottom portion than this inclined region. Thus, the second target component of a large quantity can be stored with a small area. While the position of first channel 815 is not particularly restricted either, first channel 815 must be provided on the upper portion (closer to specimen inlet 802) thereof. This is because a waste liquid treatment in a case where excess blood enters is easy and estimation of total blood measurement is simplified.

FIGS. 15A to 15F are schematic step diagrams showing a centrifugation operation with the microchip according to this embodiment. The centrifugation of the specimen in this microchip is now described with reference to FIGS. 15A to 15F.

Figure 15A:
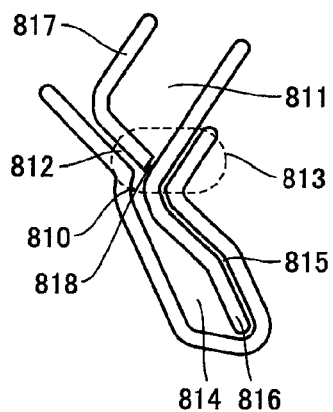
FIGS. 15A, 15B, 15C, 15D, 15E an 15F are schematic step diagrams showing a centrifugation operation with the microchip shown in FIG. 13.
Figure 15B:
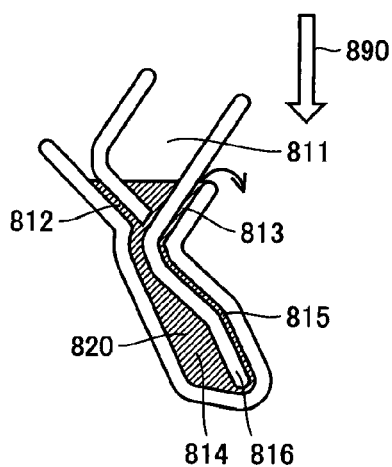
Figure 15C:
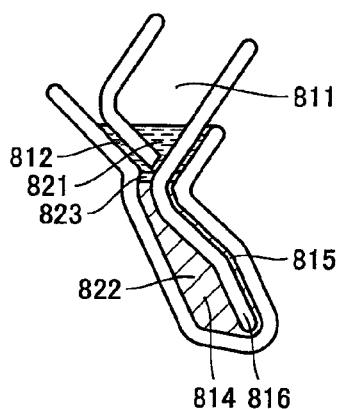

First, centrifugal force is applied to the centrifugation portion into which no specimen is introduced as shown in FIG. 15A along arrow 890, thereby introducing the specimen (blood) from specimen introducing portion 811 as shown in FIG. 15B. At this time, a specimen of a quantity unnecessary for a test is discharged from first channel 815 by measuring portion 813. First channel 815 is connected to the waste liquid reservoir (not shown). Centrifugal force is further applied along arrow 890, thereby separating a specimen 820 into a first target component 821, a second target component 822 and an intermediate layer 823, as shown in FIG. 15C.

When introducing the specimen into storage portion 814 and measuring portion 813 from specimen introducing portion 811 through opening 810, gas (air) having been present in centrifugation portion 801 moves to the air hole direction through first channel 815 or is discharged from the specimen inlet, whereby the gas (air) does not remain in centrifugation portion 801.

Figure 15D:
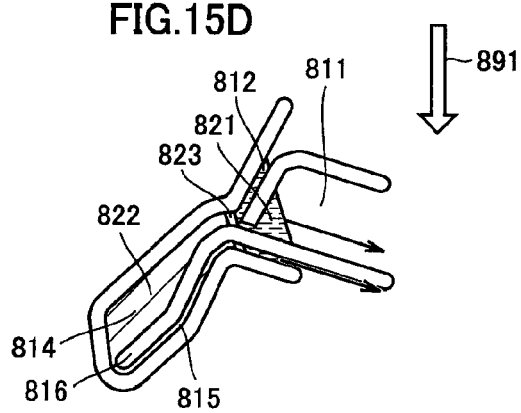
Figure 15E:
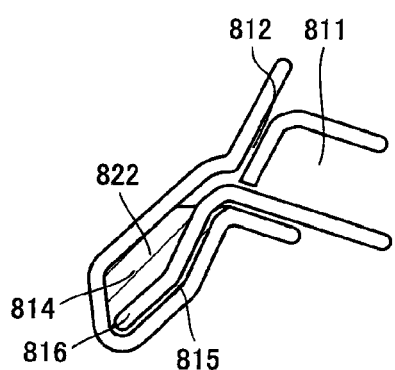

Then, centrifugal force is applied along arrow 891, so that only first target component 821 is extracted from specimen introducing portion 811 and first channel 815, as shown in FIG. 15D. The extracted first target component is introduced into the first calibration portion, as described above. The microchip is so set as to apply centrifugal force along arrow 891 in the state shown in FIG. 15E at this time, so that the first target component and the second target component are separated from each other around opening 810 and only the second target component remains in storage portion 814.

Figure 15F:
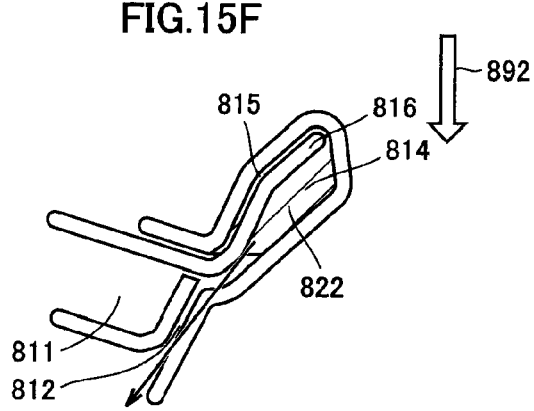

Finally, only second target component 822 can be extracted by applying centrifugal force to the microchip according to this embodiment along arrow 892, as shown in FIG. 15F. the extracted second target component is introduced into the second calibration portion, as described above.

According to the microchip of this embodiment, Glu, AST, ALT, UA or Cre using blood plasma and HbA1C or the like using a blood cell can be simultaneously tested.

Fifth Embodiment

Characteristic portions of this embodiment are now described in detail. As to the remaining points, the contents described as to the aforementioned second embodiment also apply to this embodiment.

In a microchip according to this embodiment, a fluid circuit includes a centrifugation portion for separating a specimen introduced into the microchip into a first target component and a second target component by centrifugation. When the specimen is blood, a blood plasma component can be listed as the first target component, and a blood cell component can be listed as the second target component.

The microchip according to this embodiment has a specimen inlet, and the specimen is introduced into the fluid circuit through this specimen inlet. The specimen inlet can be constituted as a through-port penetrating from one surface of the microchip up to the fluid circuit. More specifically, when the microchip is constituted of a first substrate including a groove on the aforementioned substrate surface and a second substrate, the specimen inlet can be formed by a through-port passing through the first substrate in the thickness direction. When the microchip is formed by bonding a third substrate, a first substrate including grooves provided on both surfaces of the substrate and a second substrate with each other in this order, the specimen inlet can be formed by a through-port passing through the third substrate (or the second substrate) in the thickness direction. The aforementioned centrifugation portion is connected with the specimen inlet through a channel, so that the specimen injected from the specimen inlet can be introduced into the centrifugation portion.

Figure 16:
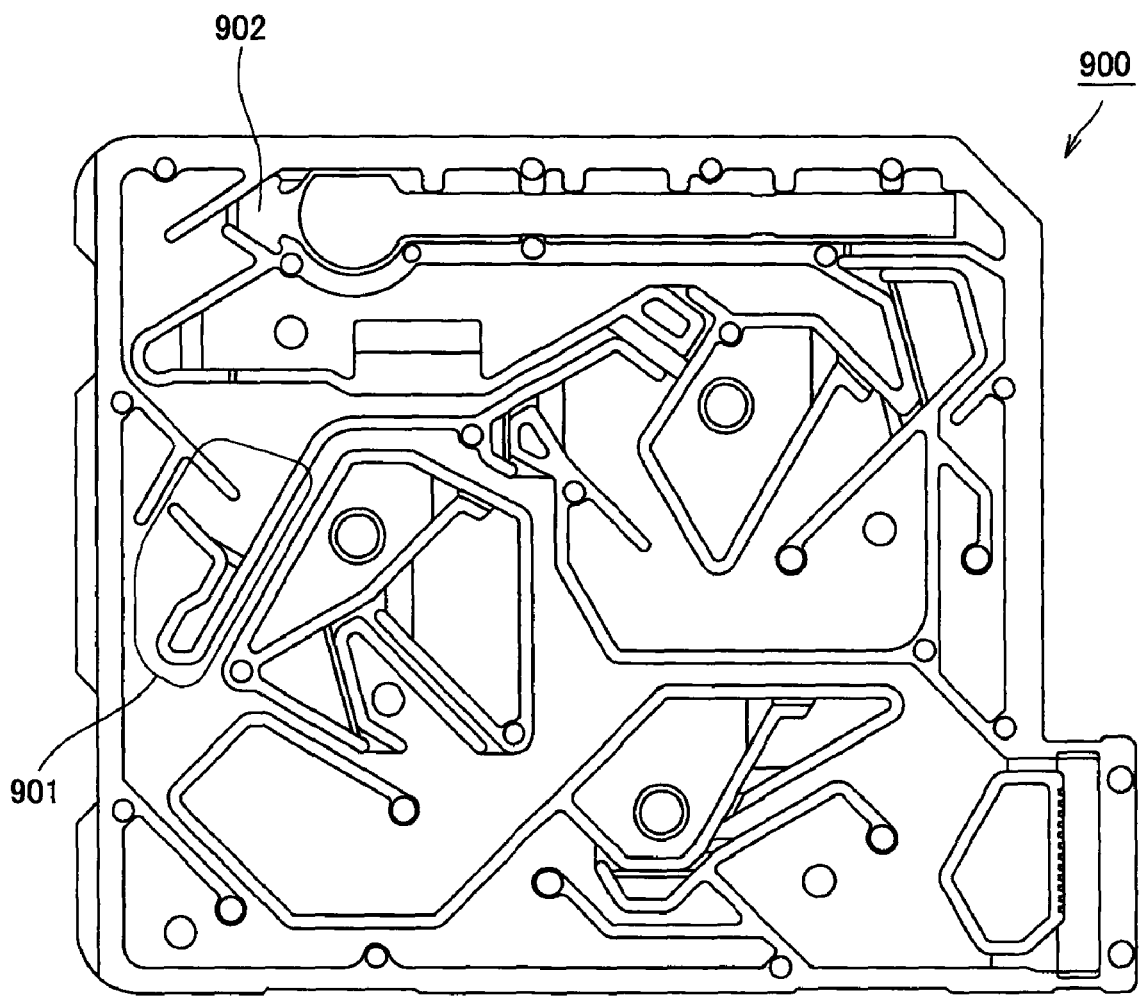
FIG. 16 is a schematic top plan view showing a preferred example of a microchip according to a fifth embodiment of the present invention.
Figure 17:
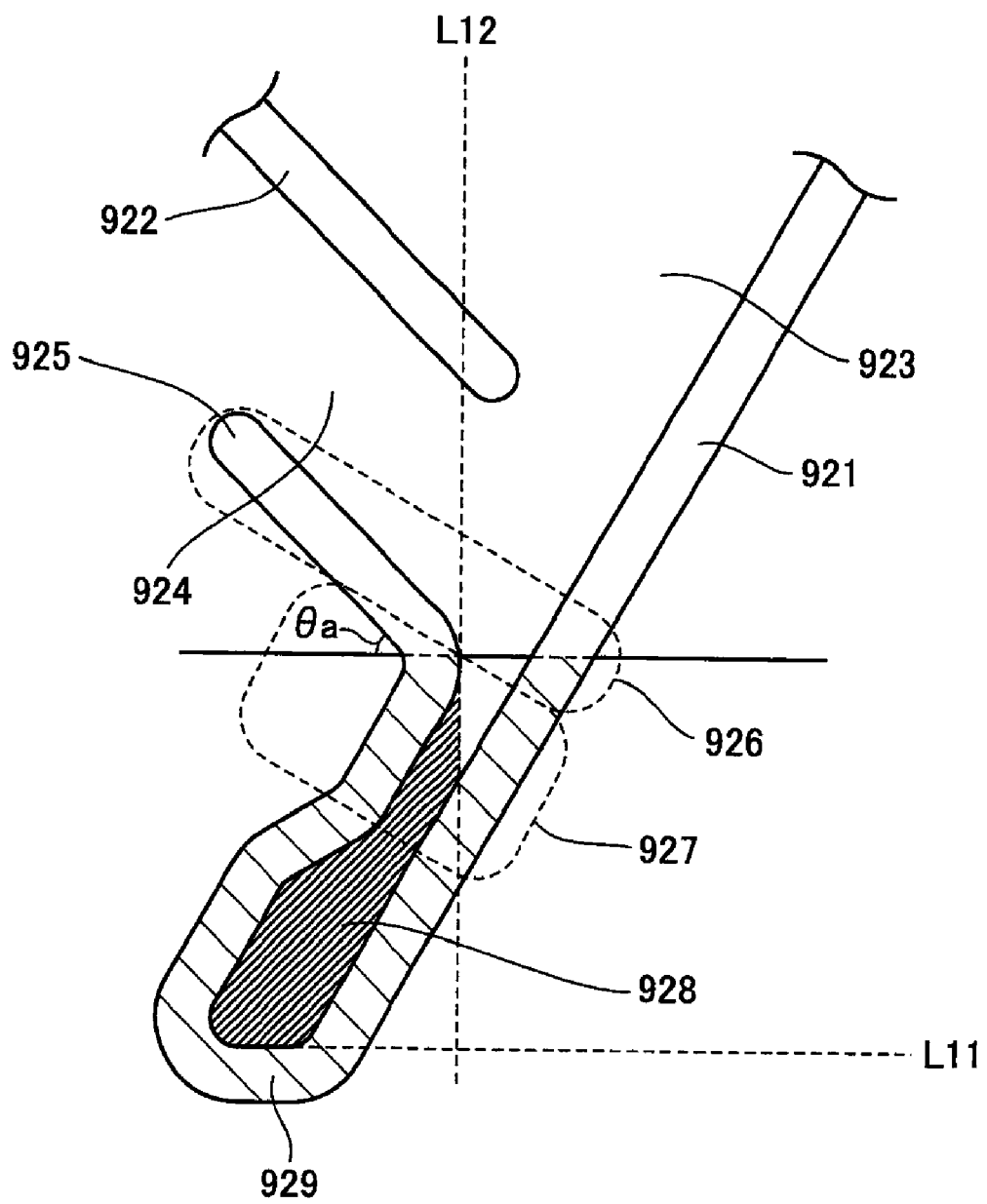
FIG. 17 is a schematic top plan view, partially enlarging FIG. 16, for illustrating a centrifugation portion.
Figure 18:
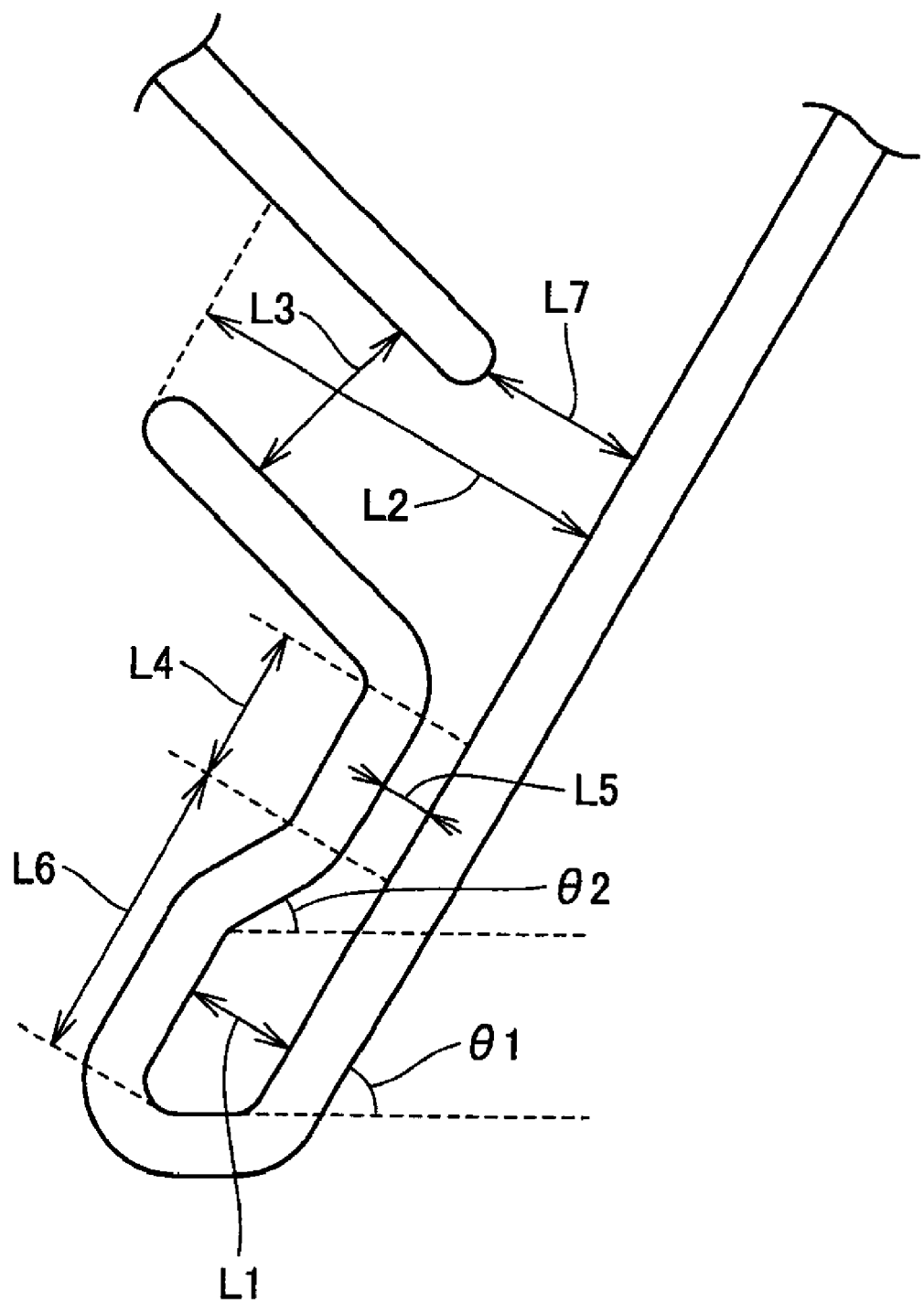
FIG. 18 is a schematic top plan view, partially enlarging FIG. 16, for illustrating preferable dimensions of the centrifugation portion.

FIG. 16 is a schematic top plan view showing a preferred example of the microchip according to this embodiment. FIG. 17 is a schematic top plan view, partially enlarging FIG. 16, for illustrating the centrifugation portion. FIG. 18 is a schematic top plan view, partially enlarging FIG. 16, for illustrating preferable dimensions of the centrifugation portion.

A microchip 900 according to this embodiment is prepared by bonding a second substrate to a groove forming-side surface of a first substrate including a groove constituting a fluid circuit and a through-hole penetrating in the thickness direction on the surface. FIG. 16 is a top plan view showing a first substrate-side surface of microchip 900. While the groove constituting the fluid circuit is formed on a surface (surface bonded to the second substrate) of the first substrate opposite to the surface denoted by 900 in practice, FIG. 16 shows the pattern of the groove with solid lines, so that the fluid circuit structure can be clearly grasped.

Microchip 900 according to this embodiment has a specimen inlet 902, penetrating from one surface thereof up to the fluid circuit, for introducing a specimen into the fluid circuit. The fluid circuit includes a centrifugation portion 901 for separating the specimen into a first target component and a second target component by centrifugation. Centrifugation portion 901 is a structural portion for separating the specimen into the first target component and the second target component larger in specific gravity than the first target component by centrifugation by applying centrifugal force to microchip 900 in a first direction. In this embodiment, the first direction is not particularly restricted so far as the same is a direction for storing the specimen in centrifugation portion 901, and the centrifugal force can be applied in a parallel direction of a specimen induction wall 921, for example.

FIG. 17 is a top plan view enlarging centrifugation portion 901 shown in FIG. 16. Respective portions of centrifugation portion 901 are now described. Centrifugation portion 901 can remove the first target component and a partial second target component while holding the rest of the second target component by applying centrifugal force to microchip 900 in the first direction and thereafter applying centrifugal force in a second direction, and can discharge the rest of the second target component from centrifugation portion 901 in the direction of specimen induction wall 921 by applying centrifugal force in a third direction after applying centrifugal force to microchip 900 in the second direction.

Preferably in this embodiment, an internal angle formed by the first direction and the second direction is 45 to 135 degrees, and an internal angle formed by the second direction and the third direction is 135 to 225 degrees. In particular, the internal angle formed by the first direction and the second direction is preferably 70 to 110 degrees, and the internal angle formed by the second direction and the third direction is preferably 160 to 200 degrees. This is because an operation of completely removing the first target component from the storage portion and feeding the second target component in the third direction without a liquid deposit must be taken into consideration in the structure of the microchip according to this embodiment.

A structure of microchip 900 capable of performing the aforementioned operation is now illustrated. Centrifugation portion 901 includes a storage portion 928, storing only the second target component, consisting of a space formed by a substantially U-shaped wall 929 to have a narrowed opening 927, and an induction wall 925 so extending in a direction separating from storage portion 928 that an angle θa with respect to the second direction is 0 to 90 degrees is connected to an end of substantially U-shaped wall 929. θa is particularly preferably 30 to 60 degrees. Preferably, aforementioned specimen induction wall 921 linearly extends from another end of substantially U-shaped wall 929. It is assumed that substantially U-shaped wall 929 is the hatched portion in FIG. 17.

Preferably, centrifugation portion 901 shown in FIG. 17 further has an auxiliary wall 922 for introducing the specimen into centrifugation portion 901 from one direction in the vicinity of induction wall 925. This is because an operation of introducing the specimen into storage portion 928 only along specimen induction wall 921 can be so prompted that air can be extruded from the bottom portion of storage portion 928 when introducing the specimen into storage portion 928.

Preferably, an end of substantially U-shaped wall 929 closer to specimen induction wall 921 is linear, and another end closer to induction wall 925 is in a form having a swelling. The form of narrowed opening 927 can be properly adjusted. The microchip can be so designed that the first target component and a partial second target component are held in a space 926 formed by induction wall 925 and specimen induction wall 921 from opening 927.

Referring to FIG. 17, L11 is parallel to the longitudinal direction of microchip 900, and the left direction along L11 becomes the second direction in FIG. 17. The microchip is so set that a prescribed quantity of the second target component can be measured on a line L12 by applying centrifugal force in the second direction. In this embodiment, L12 is a straight line, passing through the point of contact between substantially U-shaped wall 929 and induction wall 925, in a direction orthogonal to L11.

The fluid circuit formed in the microchip according to this embodiment is mainly constituted of storage portion 928, connected to specimen introducing portion 923 of centrifugation portion 901, for measuring the specimen, a waste liquid reservoir (whose position is not shown in FIG. 16) for storing the specimen overflowing storage portion 928 and a detecting portion (whose position is not shown in FIG. 16) for conducting test/analysis as to a liquid reagent A (not shown) and the second target component. Specimen inlet 902 is a through-port passing through the first substrate in the thickness direction.

An outlet 924 for discharging an excess first target component and a partial second target component is so provided independently of specimen inlet 923 for introducing the specimen that gas (air) in centrifugation portion 901 can be released in the direction of outlet 924 when introducing the specimen into centrifugation portion 901. Further, the gas (air) can be prevented from remaining in centrifugation portion 901. Thus, flows of the specimen, the first target component and the second target component smoothen, and drainage in each channel improves.

Preferable dimensions in centrifugation portion 901 are now described with reference to FIG. 18. When employing the following dimensions, it is assumed that the dimensions of microchip 900 are 45 to 50 mm in the longitudinal direction and 35 to 45 mm in the short-side direction. Referring to FIG. 18, L1 denotes the dimension of the largest width in the substantially U-shaped wall. L2 denotes the direct distance from the specimen induction wall to the terminal of the induction wall. L3 denotes the width of the outlet. L4 denotes the distance of the opening in the longitudinal direction. L5 denotes the width of the opening. L6 denotes the longitudinal distance of the storage portion. L7 denotes the width of the specimen introducing portion. θ1 denotes an internal angle formed by the second direction according to this embodiment which is the longitudinal direction of microchip 900 and the specimen introduction wall. θ2 denotes an internal angle formed by the second direction according to this embodiment which is the longitudinal direction of microchip 900 and a deflecting portion of the substantially U-shaped wall.

L1 in FIG. 18 is preferably 500 to 2000 μm, more preferably about 1000 μm. There is such an advantage that the second target component can be held in the substantially U-shaped wall, due to this dimension.

L2 is preferably 2000 to 6000 μm, more preferably about 4000 μm. There is such an advantage that a quantity in which the specimen (total blood) introduced into microchip 900 can be temporarily held can be previously defined, due to this dimension.

L3 is preferably 1500 to 2500 μm, more preferably about 2000 μm. There is an advantage of preventing diffusion of the specimen when introducing the specimen into the substantially U-shaped wall from the auxiliary wall, due to this dimension.

L4 is preferably 2000 to 3000 μm, more preferably about 2500 μm. There is such an advantage that the second target component in the substantially U-shaped wall can be held when applying centrifugal force in the second direction, due to this dimension.

L5 is preferably 300 to 600 μm, more preferably about 500 μm. There is such an advantage that solution clogging can be prevented when introducing a solution into the substantially U-shaped wall while a liquid quantity error of the second target component can be reduced when applying centrifugal force in the second direction, due to this dimension.

L6 is preferably 2000 to 5000 μm, more preferably about 3000 to 4000 μm. L7 is preferably 50 to 2000 μm, more preferably about 1000 µm. There is such an advantage that the specimen flowing from the auxiliary wall can be prevented from flowing out as a waste liquid over the induction wall, due to these dimensions.

θ1 is preferably 30 to 80 degrees, more preferably 60 degrees. There is such an advantage that the specimen can be introduced along the specimen induction wall, due to this dimension. θ2 is preferably 30 to 80 degrees, more preferably 60 degrees. There is such an advantage that air (bubbles) does not remain in the inner part after introducing the solution into the substantially U-shaped wall, due to this dimension. However, the above are illustrations, and do not particularly restrict the modes thereof.

According to the microchip of this embodiment, as hereinabove described, a precisely measured second target component can be obtained when applying centrifugal force (rightward centrifugal force in FIG. 16) for discharging the centrifuged second target in storage portion 928.

While the form of storage portion 928 is not particularly restricted, the groove bottom surface constituting storage portion 928 (hence the depth of the fluid circuit) is preferably so inclined as to further increase the depth of the groove in a region closer to the bottom portion than this inclined region. In other words, the average depth of storage portion 928 is preferably larger than the average depth of the remaining portions. This structure is so employed that the level of the second target component can be adjusted to properly come to opening 927, and the second target component of a large quantity can be stored with a small area.

FIGS. 19A, 19B, 19C and 19D are schematic step diagrams showing a centrifugation operation with the microchip shown in FIG. 16. Centrifugation of the specimen in this microchip is now described with reference to FIGS. 19A to 19D.

Figure 19A:
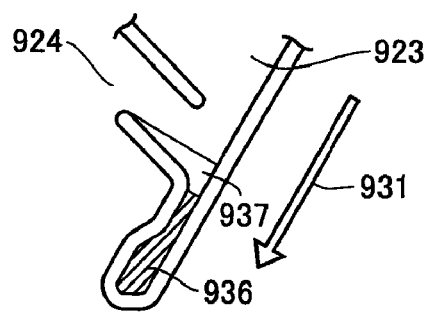
FIGS. 19A, 19B, 19C and 19D are schematic step diagrams showing a centrifugation operation with the microchip shown in FIG. 16.

First, centrifugal force is applied to the centrifugation portion into which no specimen is introduced as shown in FIG. 19A along arrow 931, thereby introducing the specimen (blood) from specimen introducing portion 923, as shown in FIG. 19A. At this time, a specimen of a quantity unnecessary for a test is discharged from outlet 924. Outlet 924 is connected to the waste liquid reservoir (not shown). Centrifugal force is further applied along arrow 931, thereby separating the specimen into a first target component 937 and a second target component 936, as shown in FIG. 19A.

When introducing the specimen into the storage portion from specimen introducing portion 923 through the opening, gas (air) having been present in centrifugation portion 901 is discharged from outlet 924, whereby no gas (air) remains in centrifugation portion 901. Further, the gas (air) does not remain in the centrifugation portion due to the specific gravity of the specimen and the gas.

Figure 19B:
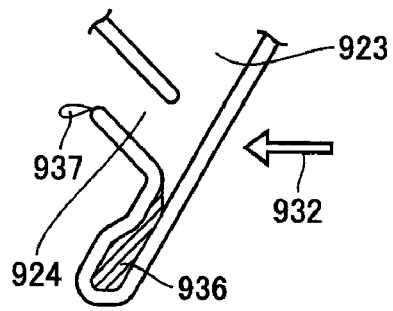

Then, centrifugal force is so applied along arrow 932 as shown in FIG. 19B that only first target component 937 unnecessary in the measurement with the microchip according to this embodiment and excess partial second target component 936 are extracted from outlet 924.

Figure 19C:
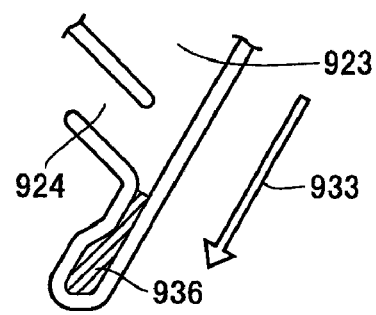

The operation of the microchip may comprise a step of regulating the level of second target component 936 by applying centrifugal force along arrow 933 as shown in FIG. 19C, as a part thereof. However, this step can be arbitrarily carried out.

Figure 19D:
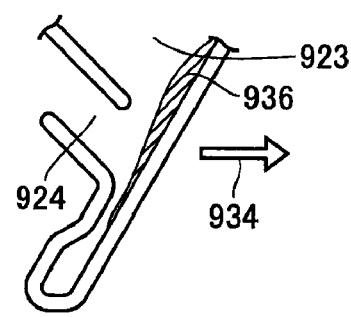

Finally, only second target component 936 can be extracted by applying centrifugal force to the microchip according to this embodiment along arrow 934, as shown in FIG. 19D.

According to this embodiment, it is possible to adjust and employ the quantity for introducing the specimen in response to the mixing ratio between the first target component and the second target component in the specimen. Therefore, when the quantity of a solution which can be held in the substantially U-shaped wall is 1.0 µL and a blood cell component of 1.0 µL is necessary, for example, it can be selected that blood of a patient whose hematocrit is 40% is introduced into microchip 900 by 2.5 µL while blood of a patient whose hematocrit is 10% is introduced into microchip 900 by 10 µL. Such selectability has such an advantage that a blood test can be conducted with a smaller total blood quantity.

Sixth Embodiment

Characteristic portions of this embodiment are now described in detail. As to the remaining points, the contents described as to the aforementioned second embodiment also apply to this embodiment.

In a microchip according to this embodiment, a fluid circuit includes a centrifugation portion for separating a specimen introduced into the microchip into a first target component and a second target component by centrifugation. When the specimen is blood, a blood plasma component can be listed as the first target component, and a blood cell component can be listed as the second target component.

The microchip according to this embodiment has a specimen inlet, and the specimen is introduced into the fluid circuit through this specimen inlet. The specimen inlet can be constituted as a through-port penetrating from one surface of the microchip up to the fluid circuit. More specifically, when the microchip is constituted of a first substrate including a groove on the aforementioned substrate surface and a second substrate, the specimen inlet can be formed by a through-port passing through the first substrate in the thickness direction. When the microchip is formed by bonding a third substrate, a first substrate including grooves provided on both surfaces of the substrate and a second substrate with each other in this order, the specimen inlet can be formed by a through-port passing through the third substrate (or the second substrate) in the thickness direction. The aforementioned centrifugation portion is connected with the specimen inlet through a channel, so that the specimen injected from the specimen inlet can be introduced into the centrifugation portion.

Figure 20:
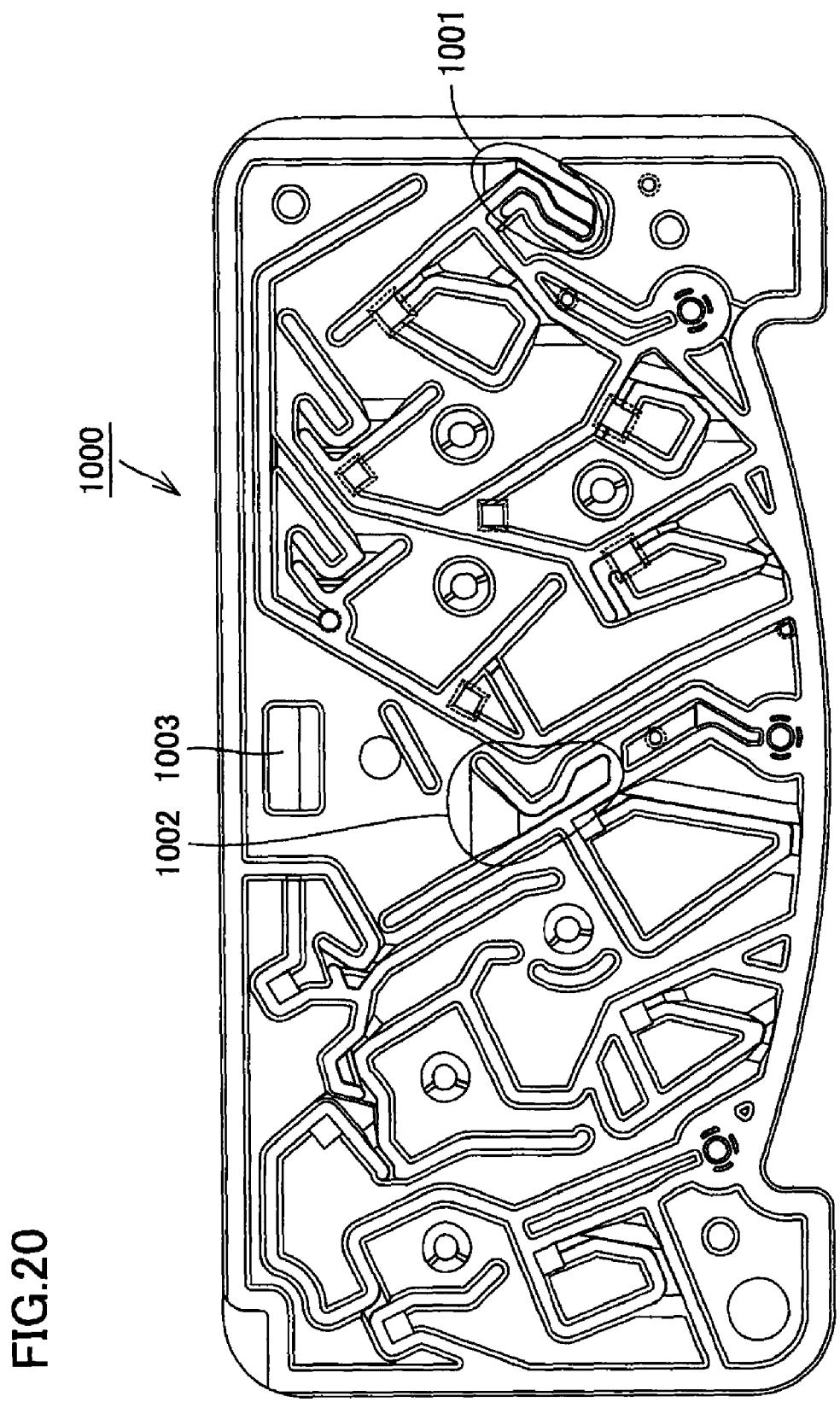
FIG. 20 is a schematic top plan view showing a preferred example of a microchip according to a sixth embodiment of the present invention.
Figure 21:
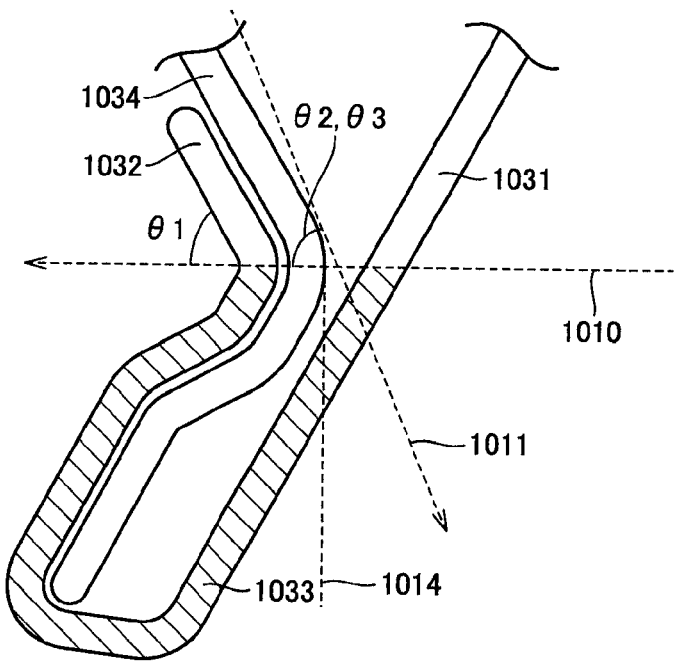
FIGS. 21 and 22 are schematic top plan views, partially enlarging FIG. 20, for illustrating the centrifugation portion.
Figure 22:
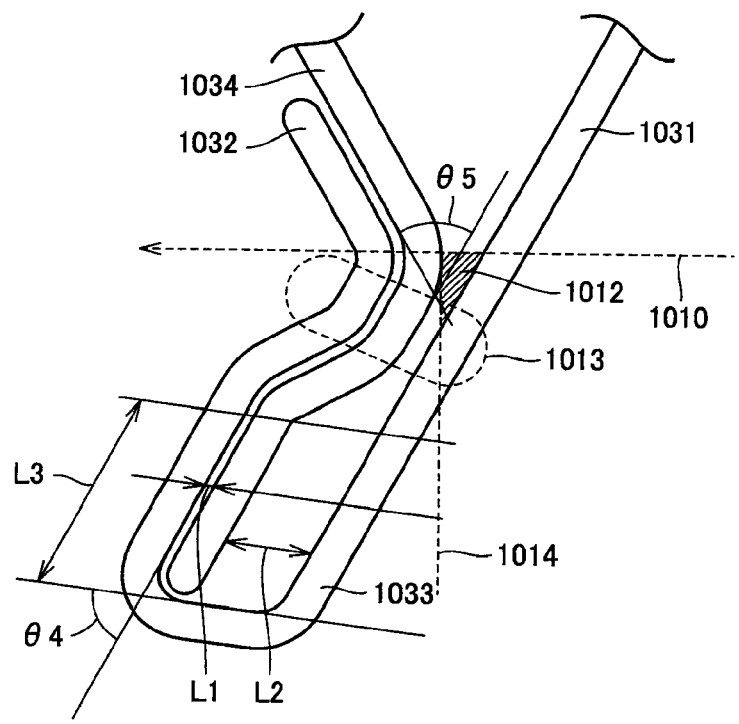

FIG. 20 is a schematic top plan view showing a preferred example of the microchip according to this embodiment. FIGS. 21 and 22 are schematic top plan views, partially enlarging FIG. 20, for illustrating the centrifugation portion.

A microchip 1000 according to this embodiment is prepared by bonding a second substrate to a groove forming-side surface of a first substrate including a groove constituting a fluid circuit and a through-hole penetrating in the thickness direction on the surface. FIG. 20 is a top plan view showing a first substrate-side surface of this microchip 1000. While the groove constituting the fluid circuit is formed on a surface (surface bonded to the second substrate) of the first substrate opposite to the surface shown in FIG. 20 in practice, FIG. 20 shows the pattern of the groove with solid lines, so that the fluid circuit structure can be clearly grasped.

Microchip 1000 according to this embodiment has a specimen inlet 1003, penetrating from one surface thereof up to the fluid circuit, for introducing a specimen into the fluid circuit. The fluid circuit includes a centrifugation portion 1001 and another centrifugation portion 1002 for separating the specimen into a first target component and a second target component larger in specific gravity than the first target component by centrifugation by applying centrifugal force to microchip 1000 in a first direction. Microchip 1000 according to this embodiment may not comprise centrifugation 1002 shown in FIG. 20, if the same comprises functions and a form of centrifugation portion 1001 described below.

According to this embodiment, only the first target component is discharged from centrifugation portion 1001 by applying centrifugal force in a second direction after applying the centrifugal force to microchip 1000 in the first direction. After applying the centrifugal force to microchip 1000 in the second direction, centrifugal force is further applied to overall microchip 1000 in a third direction for an operation necessary in design. Also in this case, however, the rest of the specimen is held in centrifugation portion 1001. This means that the rest of the specimen held in centrifugation portion 1001, i.e., a partial first target component and the second target component can be inhibited from leaking out of centrifugation portion 1001 also when applying the centrifugal force to microchip 1000 in the third direction. Therefore, reliable feeding of only the first target component is enabled in the operation of microchip 1000.

In this embodiment, it is assumed that microchip 1000 is 50 to 100 mm in the longitudinal direction, and 20 to 50 mm in the short-side direction. Further, microchip 1000 is held in a discoidal centrifugal apparatus of 40 to 50 cm in diameter so that centrifugal force is applied thereto. The first direction, the second direction and the third direction applied to microchip 1000 center on an angle defined by a spatial portion of a space 1012 shown in FIG. 22 between a second wall 1034, through which a straight line drawn in the same direction as the longitudinal direction of microchip 1000 passes, and a substantially U-shaped wall 1033 through the junction point between substantially U-shaped wall 1033 and a first wall 1032 in centrifugation portion 1001 shown in FIGS. 21 and 22 described later.

The specific form of centrifugation portion 1001 is now described. As shown in FIGS. 21 and 22, centrifugation portion FIG. 22 includes a storage portion consisting of a space formed by substantially U-shaped wall 1033 to have a narrowed opening 1013, and first wall 1032 so extending in a direction separating from the storage portion that an internal angle θ1 with respect to a second direction 1010 is 30 to 60 degrees (where it is assumed that θ1 is an internal angle of not more than 90 degrees) is connected to an end of substantially U-shaped wall 1033. Centrifugation portion 1001 includes second wall 1034, arranged up to the bottom portion of substantially U-shaped wall 1033 in the storage portion along an inner wall surface of first wall 1032 and an inner wall surface forming the storage portion, not coming into contact with the inner wall forming the storage portion. A third wall 1031 formed by serially extending substantially U-shaped wall 1033 as such is connected to another end of substantially U-shaped wall 1033 in the same direction as this end of substantially U-shaped wall 1033.

In this embodiment, second direction 1010 denotes the longitudinal direction of microchip 1000, and a leftward direction toward FIG. 20. When centrifugal force is applied to microchip 1000 in second direction 1010, centrifugal force parallel to second direction 1010 is applied around opening 1013 of centrifugation portion 1001. A first direction 1011 denotes the short-side direction of microchip 1000 and a downward direction in FIG. 20. When centrifugal force is applied to microchip 1000 in first direction 1011, centrifugal force in first direction 1011 substantially parallel to first wall 1032 is applied to centrifugation portion 1001.

The first target component and the second target component in the specimen are centrifuged when applying centrifugal force to microchip 1000 in first direction 1011, and only the first target component is discharged from centrifugation portion 1001 through second wall 1034 when applying centrifugal force in second direction 1010. Preferably, therefore, the interface between the first target component and the second target component passes through a bent portion around opening 1013 of the storage portion, and is present closer to the storage portion than a direction 1014 orthogonal to second direction 1010 with respect to centrifugation portion 1001. In other words, the interface where the first target component and the second target component are separated from each other is preferably formed on the side closer to the storage portion than opening 1013 in the centrifugation portion. This is in order to inhibit the second target component unnecessary in this embodiment from being pulled in the direction of first wall 1032 when applying centrifugal force to microchip 1000 in second direction 1010.

While the first direction is the downward direction at the central portion of microchip 1000 in this embodiment as hereinabove described, the first direction is not restricted to this. However, an inner angle θ2 formed by first direction 1011 and second direction 1010 in centrifugation portion 1001 is preferably 30 to 90 degrees, particularly preferably 60 to 90 degrees (where it is assumed that θ2 is an internal angle of not more than 90 degrees). This is because the interface between the first target component and the second target component is formed on the side closer to the storage portion and hence the second target component is not fed when applying centrifugal force in the second direction. Further, an internal angle θ3 formed by second direction 1010 and third direction 1011 is preferably 30 to 150 degrees, particularly preferably 60 to 120 degrees. This is because the remaining second target component can be held without being fed to other portions. While first direction 1011 and the third direction are substantially identical directions in this embodiment, the present invention is not restricted to this.

In this embodiment, the distance L1 between second wall 1034 and substantially U-shaped wall 1033 is preferably 100 to 300 μm, particularly preferably 200 μm. The target component entering grooves of substantially U-shaped wall 1033 and second wall 1034 becomes a useless solution since the same is substantially not utilized, and hence distance L1 is so set as to suppress the quantity of this solution to the minimum. The distance L2 between second wall 1034 and substantially U-shaped wall 1033 is preferably 0.8 to 1.2 Urn, particularly preferably 0.9 to 1.1 μm. This is in order to sufficiently store the second target component to be held and to reduce the residual quantity of the first target component. The length L3 of the storage portion is preferably 1.5 to 2.5 μm, particularly preferably 1.8 to 2.2 μm. This is because of the reason for separating the interface between the first target component and the second target component from the storage portion at a maximum and ensuring a volume necessary and sufficient for holding the second target component.

The inner wall surface of the storage portion along which second wall 1034 is arranged is bent in a substantially L-shaped manner. This is because only the first target component can be smoothly moved from centrifugation portion 1001 due to such bending. The refraction angle θ4 of the L-shaped portion is preferably 30 to 90 degrees, particularly preferably 60 to 90 degrees. This is because the solution can be charged without leaving air in the storage portion when applying centrifugal force in the first direction.

An internal angle θ5 (where it is assumed that θ5 is an internal angle of not more than 90 degrees) formed by third wall 1031 and second wall 1034 is preferably 30 to 90 degrees, particularly preferably 60 to 90 degrees. This is because introduction of the solution is easy when applying centrifugal force in the first direction, and feeding of the first target component is simplified when applying centrifugal force in the second direction.

The volume of the second target component held in the storage portion can be properly adjusted by rendering the average depth of the storage portion larger than the average depth of the remaining portions of the microchip.

Figure 23:
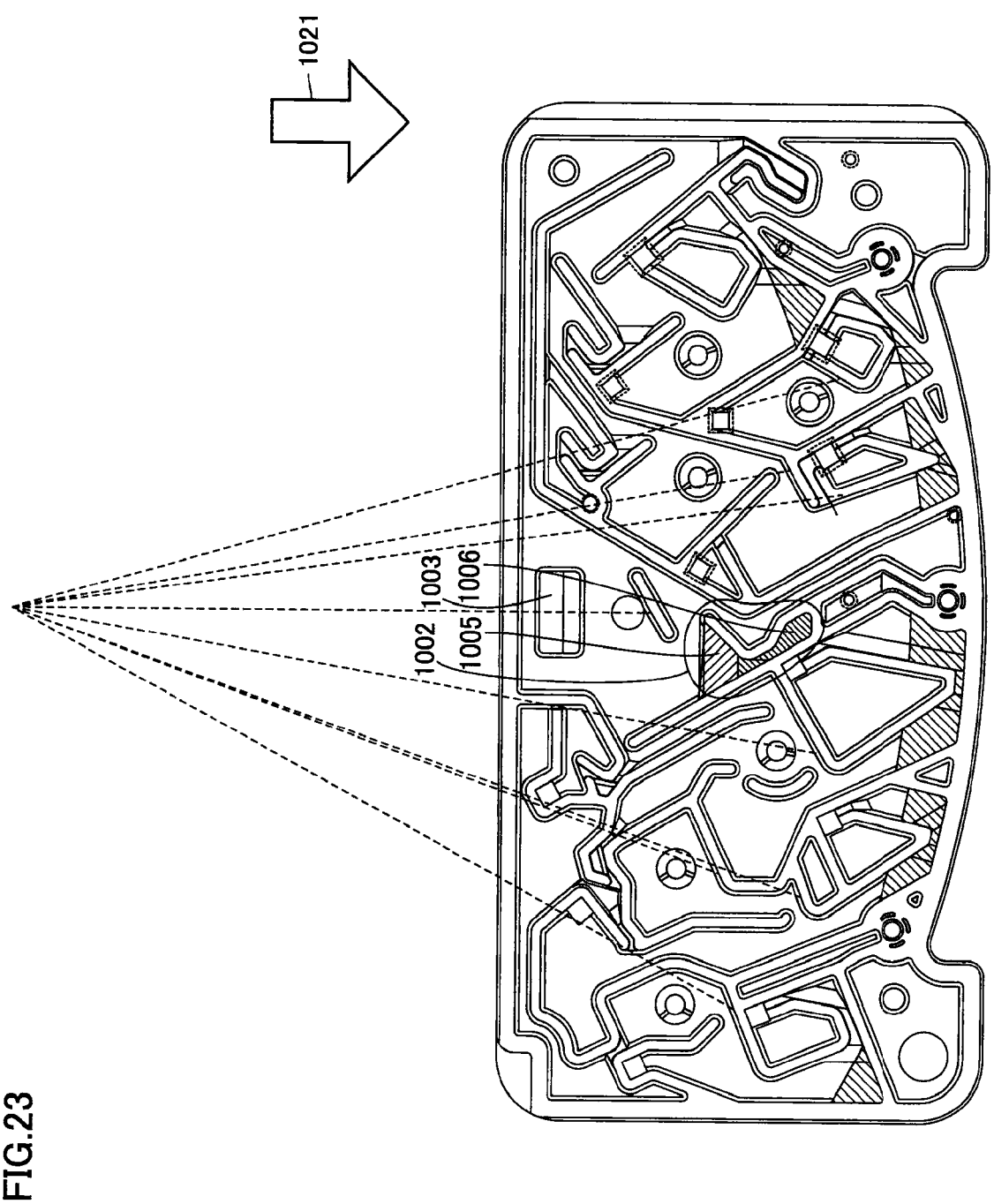
FIGS. 23, 24, 25 and 26 are schematic diagrams showing respective steps of an operation in the microchip shown in FIG. 20.
Figure 24:
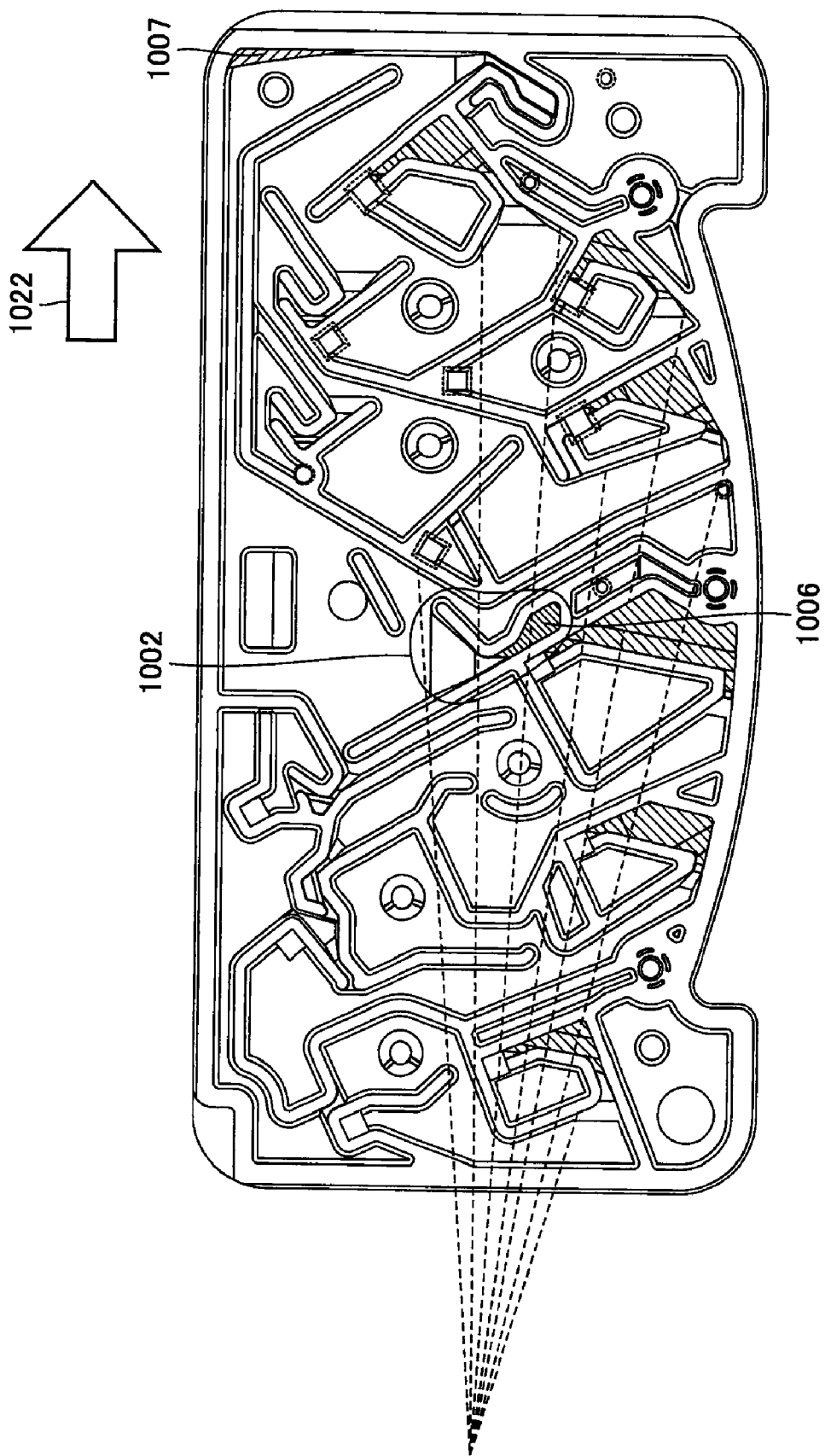
Figure 25:
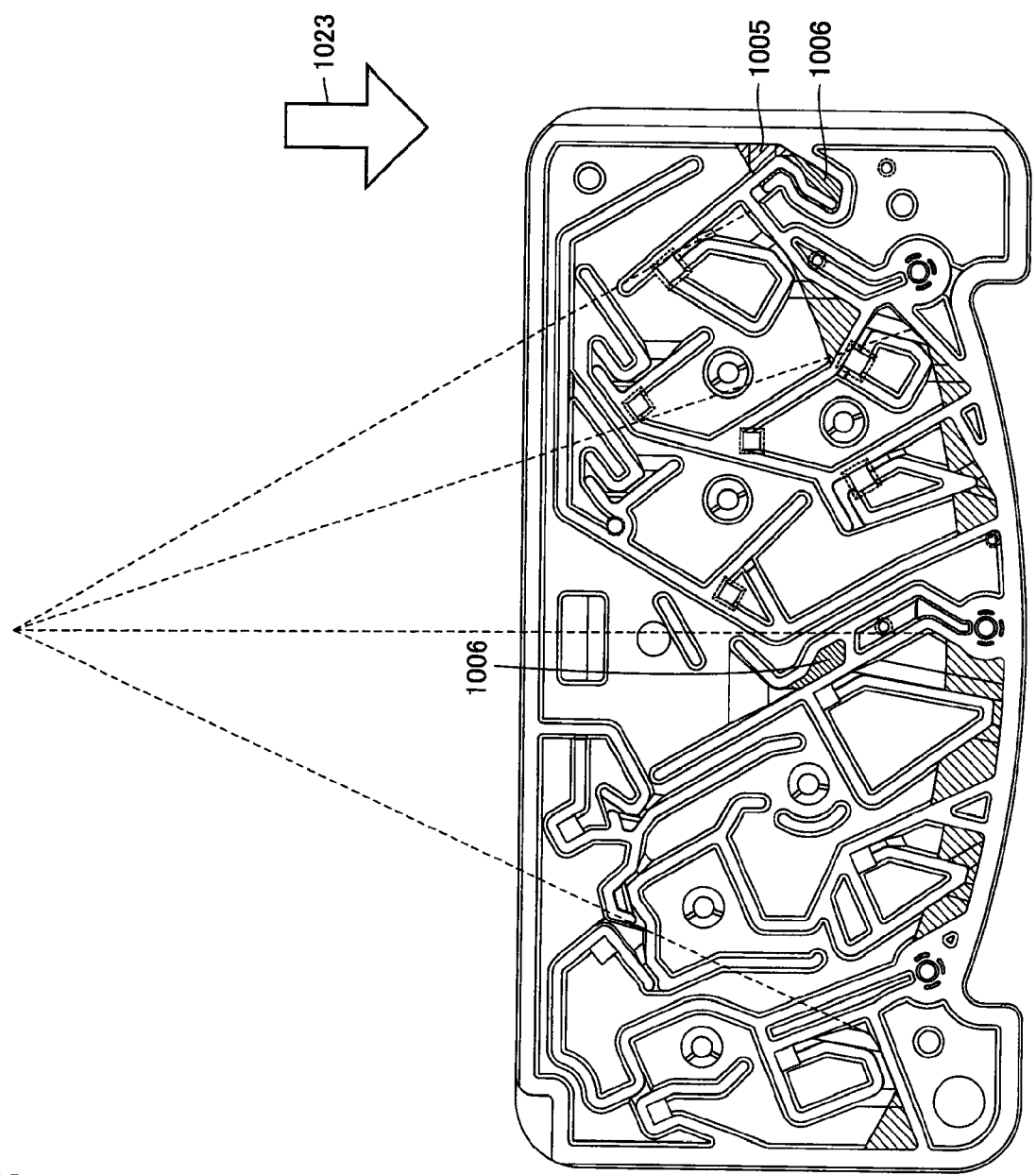
Figure 26:
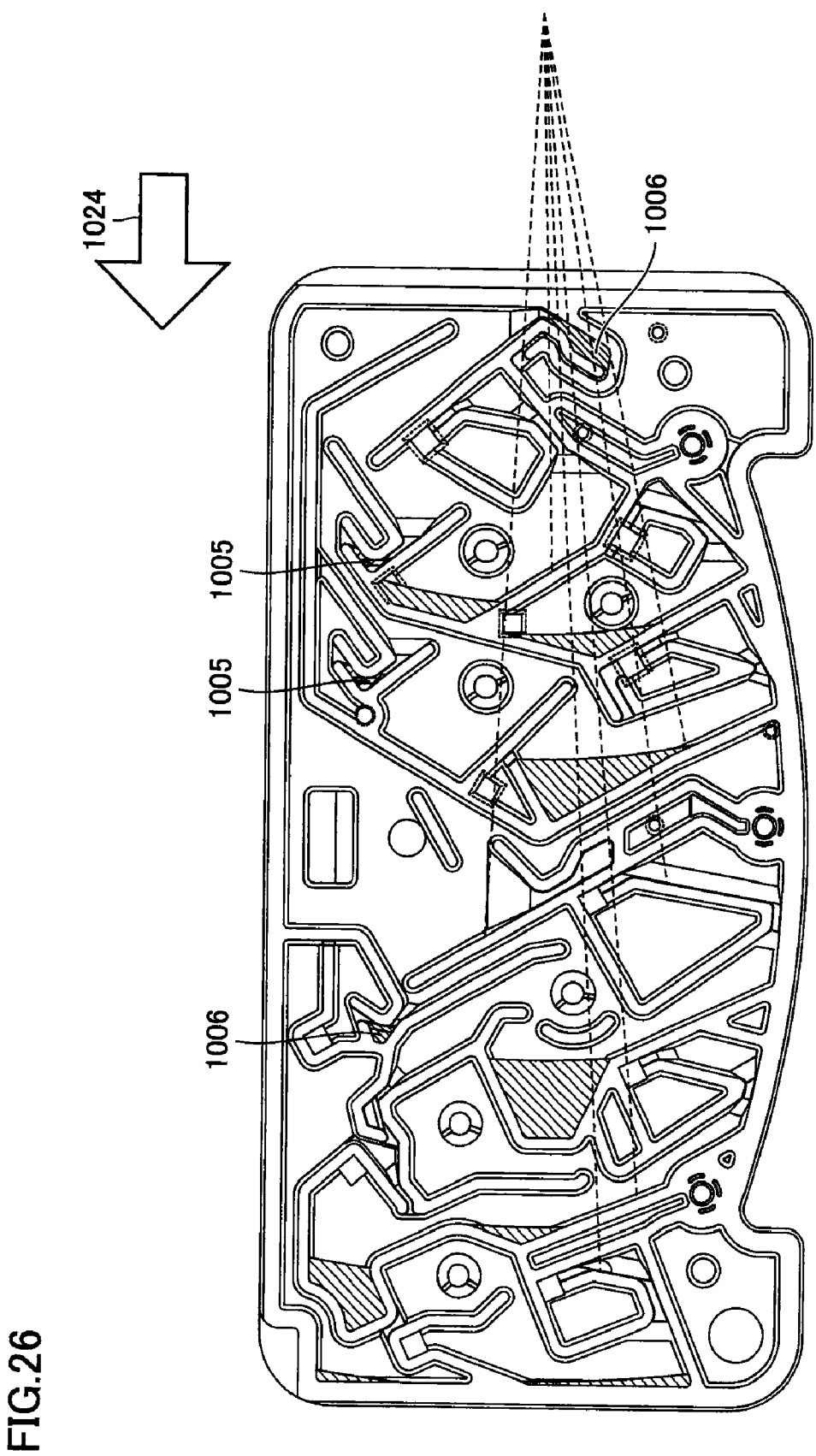

FIGS. 23, 24, 25 and 26 are schematic diagrams showing respective steps of an operation in microchip 1000 shown in FIG. 20. The following description is made with reference to FIGS. 23, 24, 25 and 26. Referring to FIGS. 25 and 26, an operation in centrifugation portion 1001 in this embodiment is described. It is assumed that white arrows in FIGS. 23, 24, 25 and 26 denote directions of centrifugal force received by the central portion of microchip 1000, and these directions are hereinafter described as leftward, rightward, upward and downward toward the drawings. Further, it is assumed that dotted lines in the drawings denote directions in which centrifugal force is applied in practice on various positions of microchip 1000.

This embodiment is described with reference to blood (total blood), blood plasma and a blood cell employed as the specimen, the first target component and the second target component respectively. However, the specimen is not particularly restricted in this embodiment, but properly applicable so far as the same is a specimen in which at least two types of solutions different in specific gravity are mixed with each other and that having the smallest specific gravity is to be employed among these.

First, the blood is introduced into the fluid circuit from specimen inlet 1003 as shown in FIG. 23, and the blood is introduced into centrifugation portion 1002 when applying centrifugal force to microchip 1000 in a downward direction 1021 toward FIG. 23. The centrifugal force is further applied to microchip 1000 in direction 1021, so that the blood is separated into a blood cell 1006 and blood plasma 1005.

Then, when applying centrifugal force to microchip 1000 in a rightward direction 1002 toward FIG. 24 as shown in FIG. 24, a mixed liquid 1007 containing partial blood cell 1006 and blood plasma 1005 moves to the upper right of microchip 1000 while only blood cell 1006 is held in centrifugation portion 1002.

Then, when applying centrifugal force to microchip 1000 in a downward direction 1023 toward FIG. 25 as shown in FIG. 25, mixed liquid 1007 is introduced into centrifugation portion 1001. The centrifugal force is further applied to microchip 1000 in direction 1023 so that the mixed liquid is separated into blood cell 1006 and blood plasma 1005. In this embodiment, mixed liquid 1007 is such a liquid that the content of blood plasma 1005 with respect to the whole is large as compared with the blood.

Then, centrifugal force is so applied in a leftward direction toward FIG. 26 as shown in FIG. 26 that only blood plasma 1005 flows out of centrifugation portion 1001 while blood cell 1006 and partial blood plasma (not shown), as the case may be, are held in centrifugation portion 1001. The microchip is so set that centrifugal force in a direction 1024 is applied to a portion around the opening in centrifugation portion 1001 at this time, as shown in FIG. 26. In this embodiment, the microchip has a form arranging blood plasma 1005 leftward beyond a perpendicular of a rotation center while arranging blood cell 1006 rightward beyond the perpendicular of the rotation center, whereby blood cell 1006 held in the storage portion of centrifugation portion 1001 hardly leaks out of the storage portion for such a reason that centrifugal force is applied to blood cell 1006 in the direction slightly separating from the storage port.

Figure 27C:
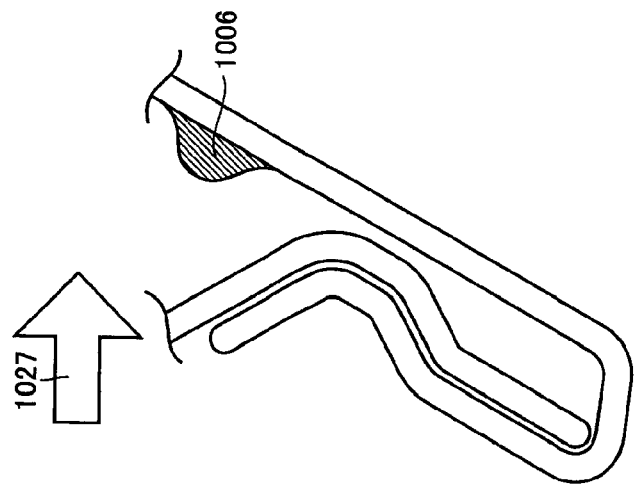
FIGS. 27A, 27B and 27C are schematic diagrams showing another operation of the centrifugation portion belonging to the microchip shown in FIG. 20.
Figure 27B:
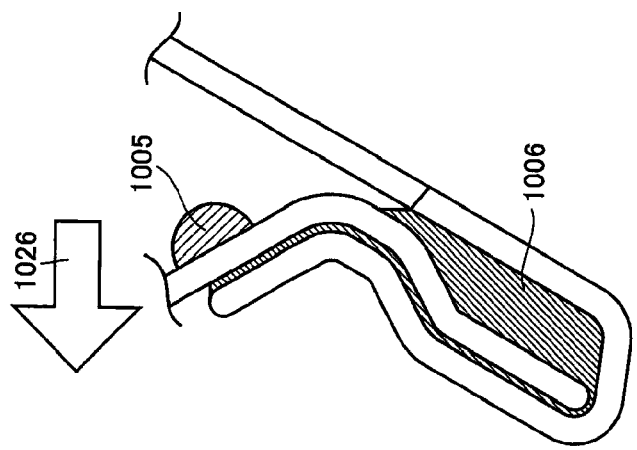
Figure 27A:
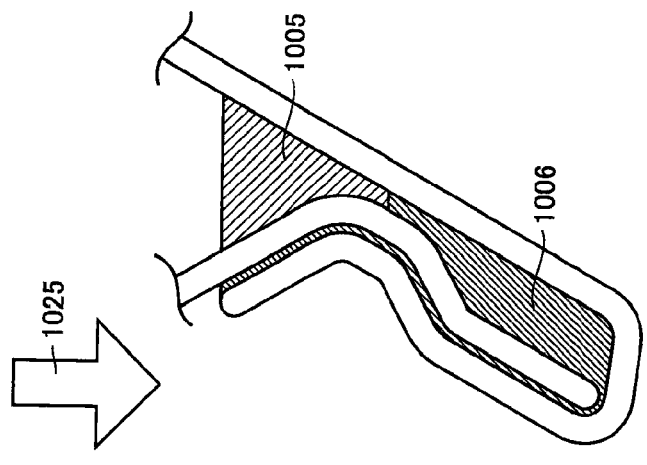

FIGS. 27A, 27B and 27C are schematic diagrams showing another operation of the centrifugation portion belonging to the microchip shown in FIG. 20.

The following description is made with reference to FIGS. 27A, 27B and 27C. As shown in FIG. 27A, centrifugal force is so applied in a downward direction 1025 toward FIG. 27A in centrifugation portion 1001 that the blood is separated into blood cell 1006 and blood plasma 1005. At this time, blood cell 1006 is held also in a space between the first wall and the second wall. At this time, centrifugal force can be applied to the microchip by setting a centrifugal apparatus under conditions of 3000 rpm and 120 seconds, for example.

As shown in FIG. 27B, centrifugal force is so applied to the microchip in a leftward direction 1026 toward FIG. 27B that only blood plasma 1005 flows out of centrifugation portion 1001. This operation is so designed that only blood cell 1006 is held in centrifugation portion 1001 by applying centrifugal force to the microchip in leftward direction 1026. At this time, the centrifugal force can be applied to the microchip by setting the centrifugal apparatus under conditions of 300 rpm and 10 seconds, for example.

As shown in FIG. 27C, only blood cell 1006 can be extracted from the direction of the third wall and utilized for analysis and measurement by applying centrifugal force to the microchip in a rightward direction 1027. At this time, the centrifugal force can be applied to the microchip by setting the centrifugal apparatus under conditions of 3000 rpm and 10 seconds, for example.

Thus, the centrifugation portion is so properly set that both of blood plasma 1005 and blood cell 1006 can be used for measurement of the microchip as the case may be.

Figure 28:
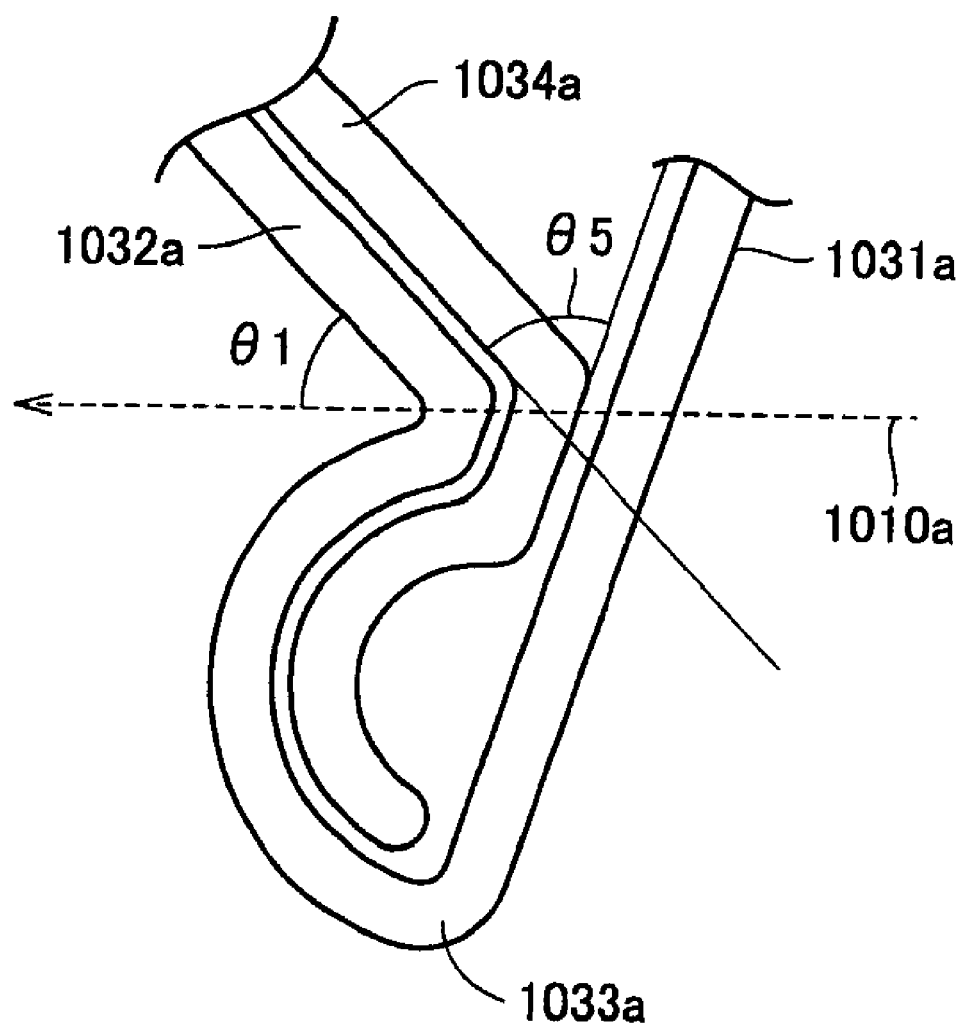
FIG. 28 is a top plan view showing another preferred example of the centrifugation portion in the microchip according to the sixth embodiment of the present invention.
Figure 29:
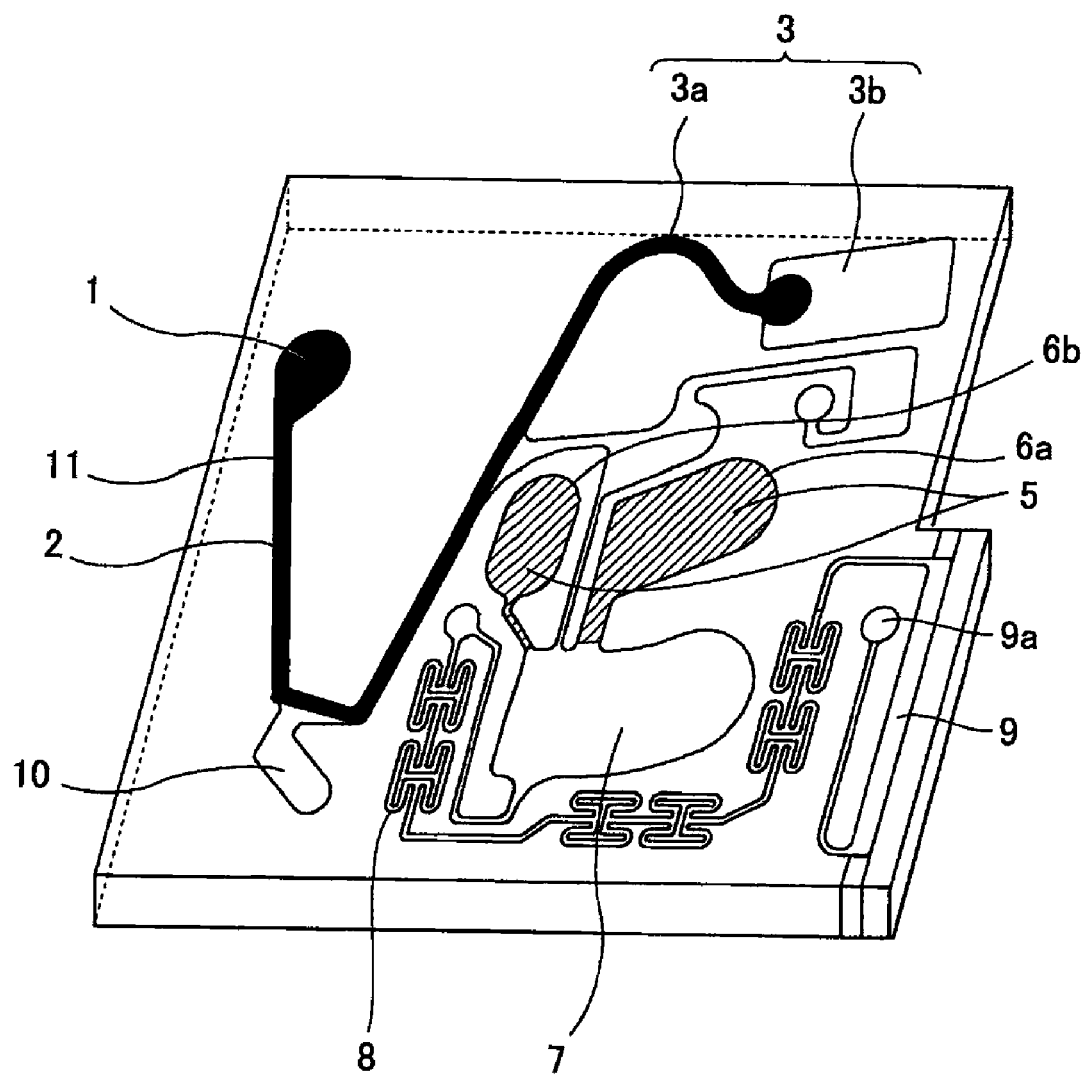
FIGS. 29, 30, 31, 32, 33 and 34 are schematic step diagrams showing an operating method of a microchip described in the pamphlet of International Patent Laying-Open No. 05/033666.
Figure 30:
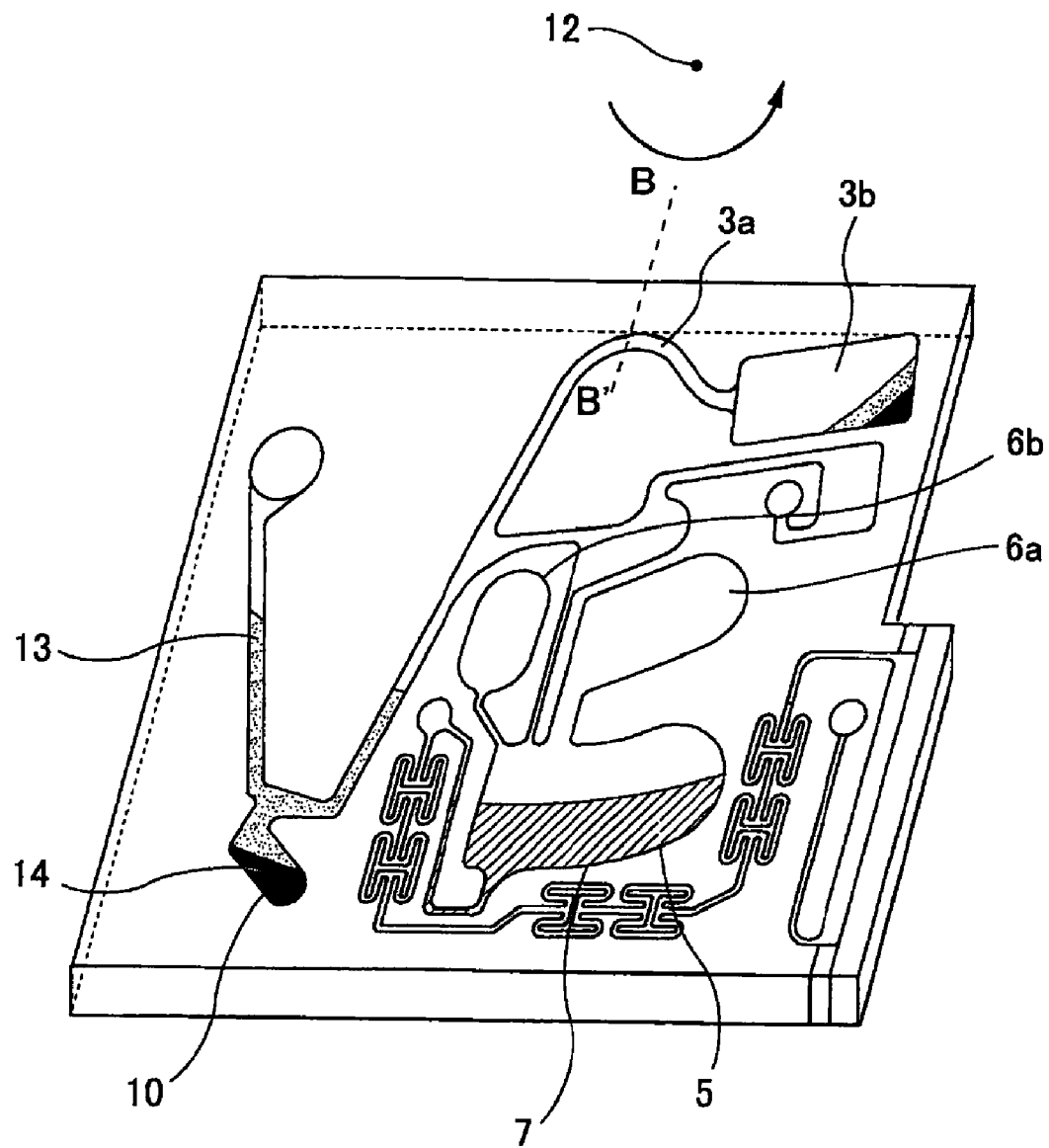
Figure 31:
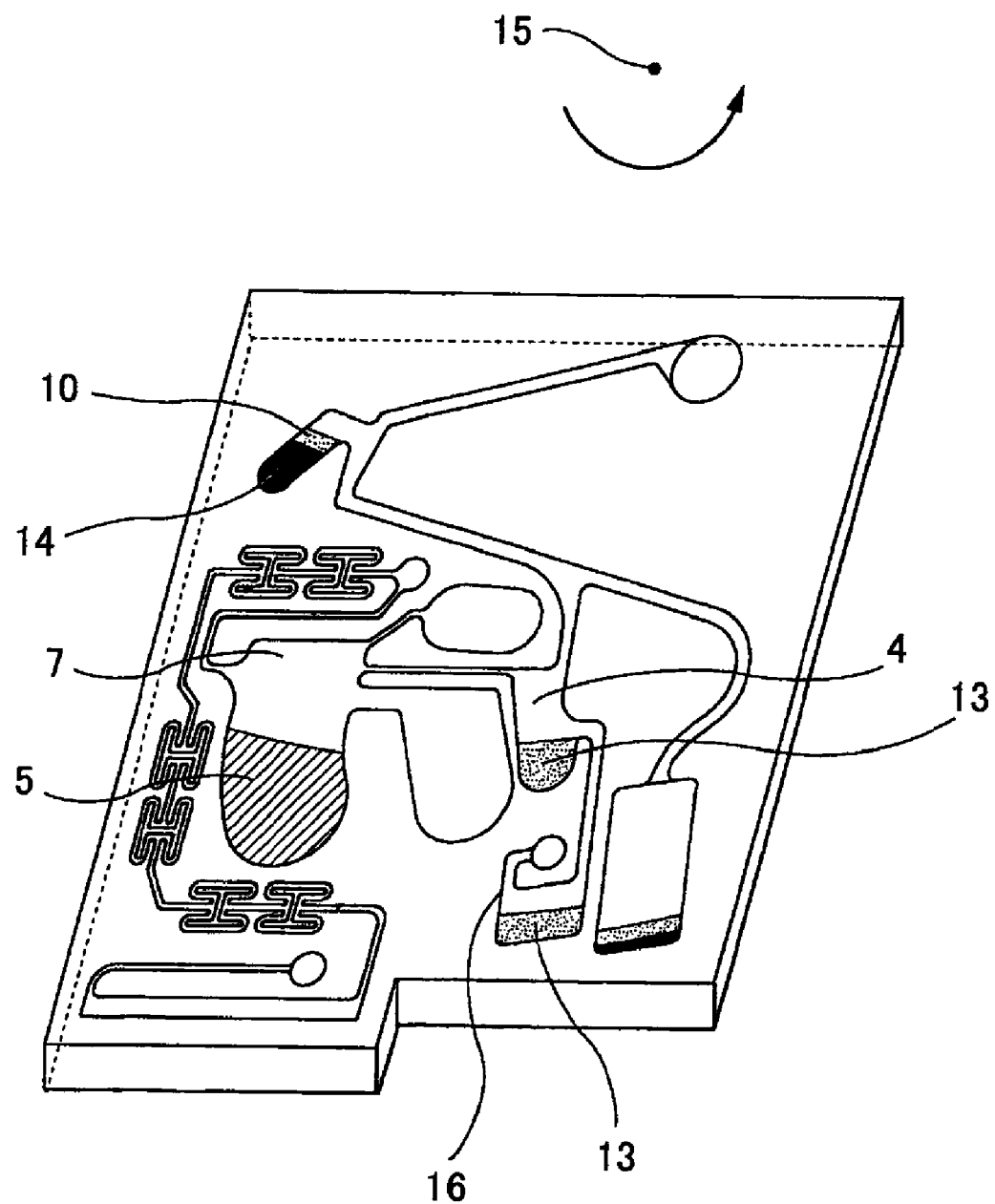
Figure 32:
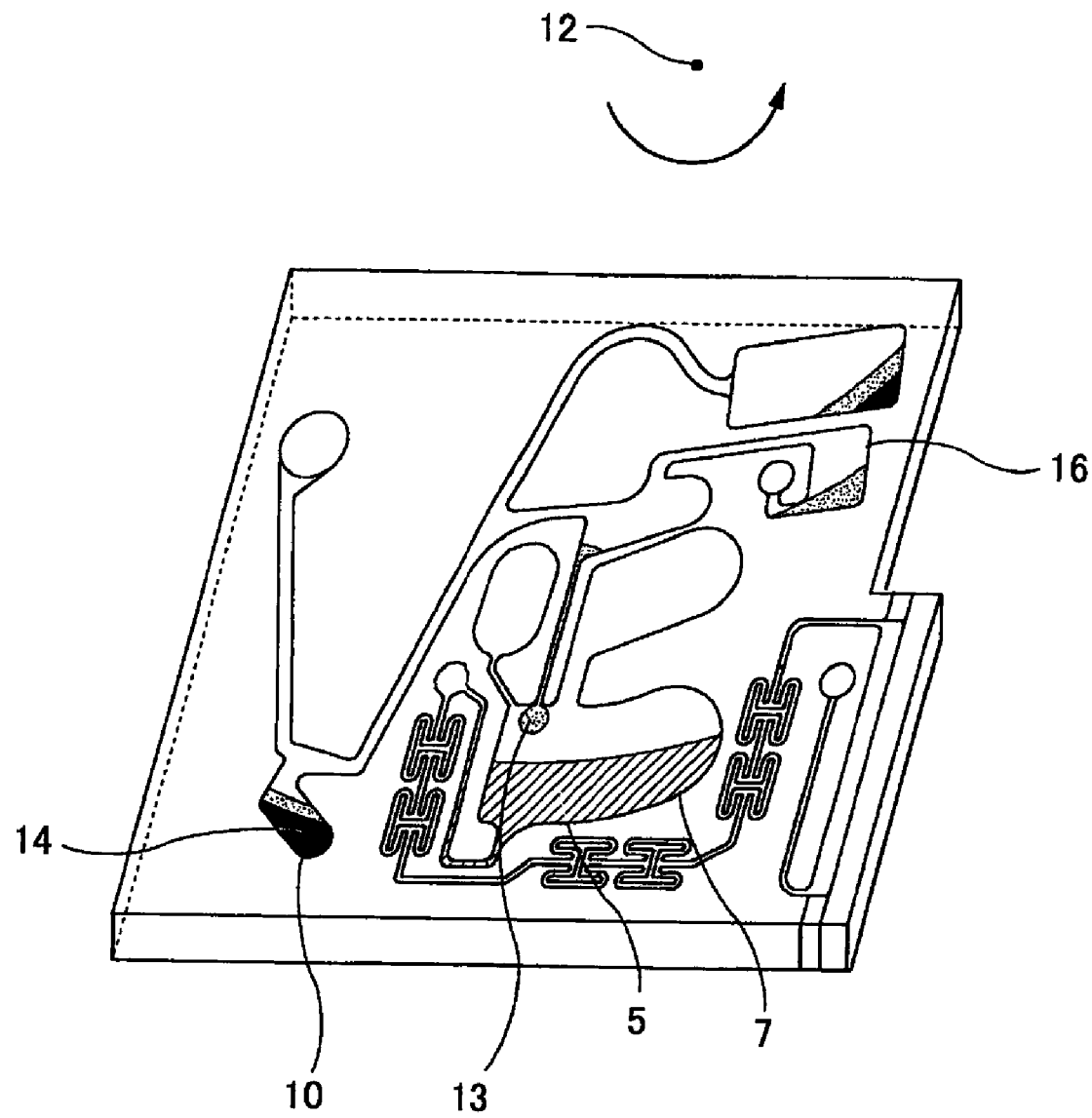
Figure 33:
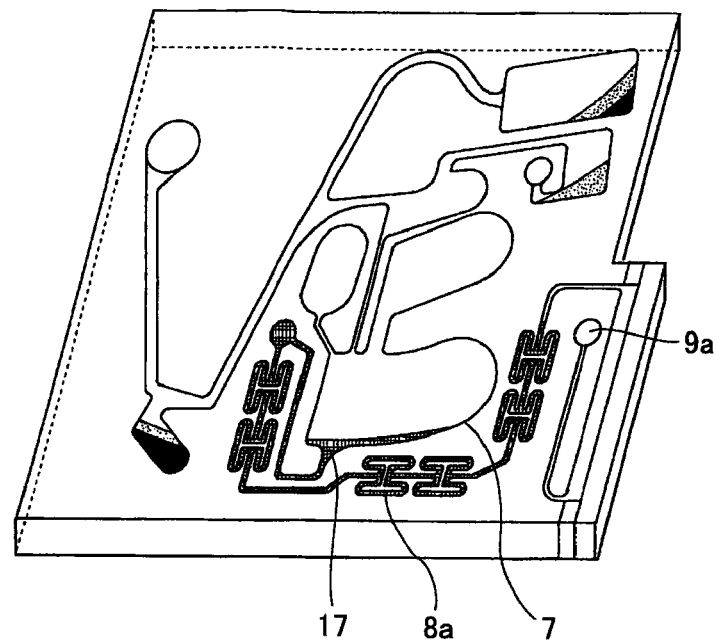
Figure 34:
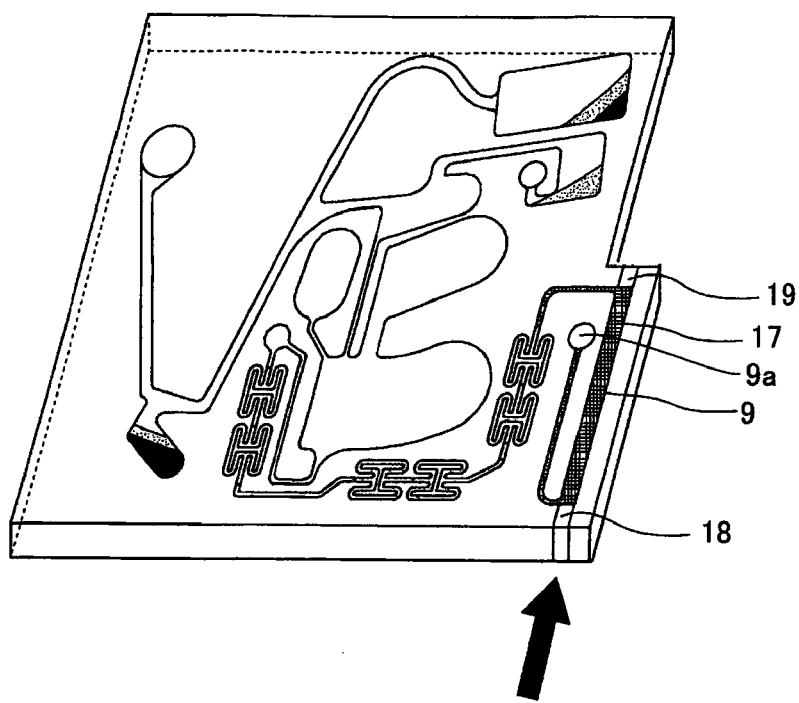

FIG. 28 is a top plan view showing another preferred example of the centrifugation portion in the microchip according to the present invention. The following description is made with reference to FIG. 28.

While the centrifugation portion shown in FIG. 28 has a structure and an operation substantially similar to those of the centrifugation portion shown in FIG. 20, an inner wall surface of a storage portion along which a second wall 1034a is arranged is bent in a substantially C-shaped manner. The inner wall surface is so bent in this manner that only a first target component can be smoothly moved from the centrifugation portion. An internal angle θ5 (where it is assumed that θ5 is an internal angle of not more than 90 degrees) formed by a third wall 1031a and second wall 1034a is preferably 30 to 90 degrees, particularly preferably 60 to 90 degrees. This is because introduction of a solution is easier when applying centrifugal force in a first direction and feeding of the first target component is simplified when applying centrifugal force in a second direction. Referring to FIG. 28, 1032a, 1033a and 1010a denote a first wall, a substantially U-shaped wall and a second direction respectively.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip comprising a first substrate bonded to a second substrate and including a groove on its surface, the microchip further comprising:
   a fluid circuit defined by said groove and a surface of said second substrate closer to said first substrate therein, wherein
   said fluid circuit includes a separation portion for separating a first component from a fluid containing at least said first component and a second component, said separation portion includes a substantially V-shaped region surrounded by points P1, P2, P3, P4, P5 and P6 arranged clockwise as viewed from the thickness direction of said first substrate, said substantially V-shaped region is a region formed by a flow channel wall W2 having a wall surface passing through the point P2 and the point P3, a flow channel wall W3 having a wall surface passing through the point P3 and the point P4, a flow channel wall W4 having a wall surface passing through the point P4 and the point P5, a flow channel wall W5 having a wall surface passing through the point PS and the point P6, and a flow channel wall W6 having a wall surface passing through the point P6 and the point P1, and an external angle formed by the wall surface of said flow channel wall W2 passing through the point P2 and the point P3 and the wall surface of the flow channel wall W3 passing through the point P3 and the point P4 and an internal angle formed by the wall surface of said flow channel wall W5 passing through the point P5 and the point P6 and the wall surface of the flow channel wall W6 passing through the point P6 and the point P1 are less than 180 degrees respectively.

2. The microchip according to claim 1, wherein a portion having no flow channel wall reaching said point P2 from said point P1 is an opening for introducing said fluid.

3. The microchip according to claim 2, wherein
the depth of the groove in said opening is smaller than the depth of the groove in a region B surrounded by said point P3, the point P4, the point P5 and the point P6, and
the groove bottom surface in a region forming a part of a region A surrounded by said point P1, the point P2, the point P3 and the point P6 and including a straight line passing through said point P3 and the point P6 has an is inclined structure changing from the depth of the groove in said opening to the depth of the groove in said region B.

4. The microchip according to claim 2, wherein
said fluid circuit further has a flow rate limiting portion for limiting the flow rate of said fluid introduced into said separation portion above said opening as viewed from the thickness direction of said first substrate, and
a groove constituting said flow rate limiting portion is constituted of a linearly extending flow channel wall W7 and a flow channel wall W8 formed to be opposed to said flow channel wall W7.

5. The microchip according to claim 4, wherein
the groove constituting said flow rate limiting portion is formed by a linear wall surface belonging to said flow channel wall W7 and another linear wall surface belonging to said flow channel wall W8, and
the linear wall surface belonging to said flow channel wall W7 and the linear wall surface belonging to said flow channel wall W8 are substantially parallel to each other.

6. The microchip according to claim 5, wherein
the distance from said point P1 to said point P2 is three to 10 times as large as the distance between the linear wall surface belonging to said flow channel wall W7 and the linear wall surface belonging to said flow channel wall W8.

7. The microchip according to claim 4, wherein said flow channel wall W7 extends to said point P2.

8. The microchip according to claim 7, wherein
an external angle formed by the linear wall surface belonging to said flow channel wall W7 and the wall surface of said flow channel wall W2 passing through the point P2 and the point P3 is larger than 180 degrees and smaller than 240 degrees.

9. A microchip comprising a first substrate bonded to a second substrate and including a groove on its surface, the microchip further comprising:
a fluid circuit defined by said groove and a surface of said second substrate closer to said first substrate therein, wherein
said fluid circuit includes a separation portion for separating a first component from a fluid, having an opening for introducing said fluid containing at least said first component and a second component, and a flow rate limiting portion arranged above said opening for limiting the flow rate of said fluid introduced into said separation portion,
said flow rate limiting portion in said first substrate is formed by a flow channel wall W7 having a linearly extending wall surface a and a flow channel wall W8 having a linearly extending wall surface b substantially parallel to said wall surface a,
an angle $\theta 4$ formed by a wall surface c, belonging to said flow channel wall W8, on a side of said opening and said wall surface a satisfies 90 degrees$<\theta 4<$180 degrees, and
the following expression (1) is satisfied assuming that L1 represents the distance between said wall surface a and said wall surface b, L2 represents the width of said opening and R represents the radius of curvature of a corner portion of said flow channel wall W8 formed by said wall surface b and said wall surface c:

$$2\times(L1+R)<L2 \tag{1}$$

* * * * *